US010131911B2

(12) United States Patent
Arhancet et al.

(10) Patent No.: US 10,131,911 B2
(45) Date of Patent: Nov. 20, 2018

(54) POST-TRANSCRIPTIONALLY CHEMICALLY MODIFIED DOUBLE STRAND RNAS

(71) Applicant: nanoSUR LLC, Miami, FL (US)

(72) Inventors: Juan P. Arhancet, Miami, FL (US); Sreevishnu Cheerla, Miami, FL (US); Graciela B. Arhancet, Miami, FL (US); David B. Rozema, Cross Plains, WI (US)

(73) Assignee: nanoSUR LLC, Miami, FL (US)

( * ) Notice: Subject to any disclaimer, the term of this patent is extended or adjusted under 35 U.S.C. 154(b) by 0 days.

(21) Appl. No.: 15/803,948

(22) Filed: Nov. 6, 2017

(65) Prior Publication Data

US 2018/0127753 A1 May 10, 2018

Related U.S. Application Data

(60) Provisional application No. 62/418,581, filed on Nov. 7, 2016, provisional application No. 62/446,722, filed on Jan. 16, 2017.

(51) Int. Cl.

| | |
|---|---|
| ***C12N 15/113*** | (2010.01) |
| ***A01N 57/16*** | (2006.01) |
| ***C12N 15/82*** | (2006.01) |

(52) U.S. Cl.

CPC ............ *C12N 15/113* (2013.01); *A01N 57/16* (2013.01); *C12N 15/8218* (2013.01); *C12N 2310/14* (2013.01); *C12N 2310/322* (2013.01); *C12N 2330/30* (2013.01)

(58) Field of Classification Search

CPC .................................................... C12N 15/113
USPC ........................................................ 536/23.1
See application file for complete search history.

(56) References Cited

U.S. PATENT DOCUMENTS

| | | | | |
|---|---|---|---|---|
| 6,867,290 | B2 | 3/2005 | Goldsborough | |
| 9,121,022 | B2 | 9/2015 | Sammons et al. | |
| 2014/0302593 | A1 | 10/2014 | Arhancet et al. | |
| 2016/0177299 | A1 | 6/2016 | Arhancet et al. | |
| 2016/0208221 | A1 | 7/2016 | Arhancet et al. | |
| 2016/0215290 | A1 | 7/2016 | Kogel | |
| 2017/0305956 | A1* | 10/2017 | Brown | C07H 21/04 |

OTHER PUBLICATIONS

Baum JA and Roberts JK "Progress towards RNAi-mediated insect pest management." Adv. Insect Physiol (2014) 47: 249-295.
Baum, J. "Rnai-mediated insect pest management: challenges and opportunities." XXVth International Congress of Entomology 2016, Orlando, Florida, U.S.A.
Bolognesi R et al. "Characterizing the mechanism of action of double-stranded RNA activity against western corn rootworm (Diabrotica virgifera virgifera LeConte)." PLoS One (2012) 7.10: e47534.
Chen X et al. "Poly-2'-DNP-RNAs with enhanced efficacy for inhibiting cancer cell growth." Oligonucleotides (2004) 14.2: 90-99.
Choi M-Y et al. "Phenotypic impacts of PBAN RNA interference in an ant, Solenopsis invicta, and a moth, Helicoverpa zea." Journal of Insect Physiology (2012) 58.8: 1159-1165.
Fire et al. "Potent and specific genetic interference by double-stranded RNA in Caenorhabditis elegans." Nature (1998) 391.6669: 806-811.
Gong L et al. "Silencing of Rieske iron—sulfur protein using chemically synthesised siRNA as a potential biopesticide against Plutella xylostella." Pest Management Science (2011) 67.5: 514-520.
Gong L et al. "Testing insecticidal activity of novel chemically synthesized siRNA against Plutella xylostella under laboratory and field conditions." PloS One (2013) 8.5: e62990.
Hauge et al. "Single tube, high throughput clonging of inverted repeat constructs for double stranded RNA expression" PLoS One (2009) 4(9): e7205.
Hemingway J et al. "The molecular basis of insecticide resistance in mosquitoes." Insect Biochemistry and Molecular Biology (2004) 34.7: 653-665.
Ivashuta S et al. "Environmental RNAi in herbivorous insects." RNA (2015) 21.5: 840-850.
Killini N et al. "Double-Stranded RNA Uptake through Topical Application, Mediates Silencing of Five CYP4 Genes and Suppresses Insecticide Resistance in Diaphorina citri" PLoS Pathog (2014) 9.10: e110536.
Koch A et al. "An RNAi-Based Control of Fusarium graminearum Infections Through Spraying of Long dsRNAs Involves a Plant Passage and Is Controlled by the Fungal Silencing Machinery." PLoS Pathog (2016) 12.10: e1005901.
Koch A et al. "Host-induced gene silencing of cytochrome P450 lanosterol C14α-demethylase—encoding genes confers strong resistance to *Fusarium* species." Proceedings of the National Academy of Sciences (2013) 110.48: 19324-19329.
Koch A et al. "The antimicrobial peptide thanatin reduces fungal infections in Arabidopsis." Journal of Phytopathology (2012) 160. 10: 606-610.
Krieg PA and Melton DA "In Vitro RNA Synthesis with SP6 RNA Polymerase" Methods in Enzymology (1987) 155: 397-415.
Ku SH et al. "Chemical and structural modifications of RNAi therapeutics." Advanced Drug Delivery Reviews (2015).
Merino EJ et al. "RNA structure analysis at single nucleotide resolution by selective 2'-hydroxyl acylation and primer extension (SHAPE)." Journal of the American Chemical Society (2005) 127.12: 4223-4231.
Micura R "Small interfering RNAs and their chemical synthesis." Angewandte Chemie International Edition (2002) 41.13: 2265-2269.
Nodin L et al. "RNA Shape chemistry with aromatic acylating reagents." Bioorganic & Medicinal Chemistry Letters (2015) 25.3: 566-570.
Song et al. "RNA secondary structural determinants of miRNA precursor processing in Arabidopsis" Current Biology (2010) 20, 37-41.

(Continued)

*Primary Examiner* — Jezia Riley
(74) *Attorney, Agent, or Firm* — Hamilton, Brook, Smith & Reynolds, P.C.

(57) ABSTRACT

Described are post transcriptionally chemically modified double strand RNAs (MdsRNAs) having more than 30 base pairs. The MdsRNAs inhibit gene expression in target organisms. Also described are methods of making and using MdsRNAs.

9 Claims, 2 Drawing Sheets

Specification includes a Sequence Listing.

(56) References Cited

OTHER PUBLICATIONS

Rycke ND et al. "Synthesis and Reactivity of Highly Nucleophilic Pyridines." Organic letters (2010) 13.3: 530-533.
Timmons L "Construction of plasmids for RNA interference and in vitro transcription of double-stranded RNA." C. elegans: Methods and Applications (2006): 109-117, chaper 8.
Tiwari S et al. "Insecticide resistance in field populations of Asian citrus psyllid in Florida." Pest Management Science (2011) 67.10: 1258-1268.
Tiwari S et al. "Biochemical basis of organophosphate and carbamate resistance in Asian citrus psyllid" J Econ Entomol (2012) 105: 540-548.
Wojcik DP et al. "Red imported tire ants: impact on biodiversity." American Entomologist-Lanham (2001) 47.1: 16-23.
Yates et al. Cell (2013) vol. 153 , Issue 3 , 516-519.
Zhang, B et al. "Cloning and Expression of Multiple Cytochrome P450 Genes: Induction by Fipronil in Workers of the Red Imported Fire Ant (*Solenopsis invicta* Buren)." PloS one 11.3 (2016): e0150915.
Gagniuc P et al. "Eukaryotic genomes may exhibit up to 10 generic classes of gene promoters." BMC genomics 13.1 (2012): 512.
Kuehner J et al. "Unravelling the means to an end: RNA polymerase II transcription termination." Nature reviews Molecular cell biology (2011) 12.5: 283-294.
Linderz T, et al. "A family of putative transcription termination factors shared amongst metazoans and plants." Current genetics 48.4 (2005): 265-269.
Platt T "Transcription termination and the regulation of gene expression." Annual review of biochemistry 55.1 (1986): 339-372.
Shahmuradov IA et al. "PlantProm: a database of plant promoter sequences." Nucleic acids research 31.1 (2003): 114-117.

* cited by examiner

BnsDMAP

EtsDMAP

MesDMAP

POST-TRANSCRIPTIONALLY CHEMICALLY MODIFIED DOUBLE STRAND RNAS

CROSS-REFERENCE TO RELATED APPLICATIONS

This application claims priority to U.S. provisional application Ser. No. 62/418,581, filed 7 Nov. 2016 and U.S. provisional application Ser. No. 62/446,722, filed 16 Jan. 2017, each of which is incorporated by reference in its entirety.

FIELD

Described are compositions of modified double strand RNA (MdsRNA) longer than about 30 base pairs (bp) having chemically modified nucleotides, such that the MdsRNAs are capable of inhibiting gene expression on target plants, animals (including insects), or fungi. Such compositions have application in crop protection.

BACKGROUND

RNA interference (RNAi) is a naturally occurring biological process by which double-stranded ribonucleic acid (dsRNA) silences (knocks down) target gene expression in a sequence specific manner. Cellular enzymes use dsRNA to target and cleave single stranded RNA (ssRNA), including messenger RNA (mRNA) and non-coding RNA. RNAi is known to occur in many eukaryotes, including plants, fungi, and animals, and offers great potential for selective and efficient regulation of gene expression.

The dsRNA has an antisense strand containing sequence complementary to a sequence in the mRNA or non-coding RNA and a sense strand substantially identical to the sequence in the mRNA or non-coding RNA. The sense and antisense sequences can be present on separate RNA strands or on a single strand. When present on a single strand, the complementary sequences are connected by a non-hybridizing hairpin or loop sequence.

RNAi-mediated gene suppression on targeted weeds, insects, and fungi affecting crops described in the prior art has been achieved using exogenously supplied unmodified dsRNA (UdsRNA) (U.S. Pat. No. 9,121,022; Ivashuta et al. 2015; US Publication No. 20160215290; Koch et al. 2016). It has been found, that when dsRNAs are used to induce RNAi in insects and are supplied in the insects' diet, 60 base pair (bp) or longer dsRNAs are sometimes required for efficient uptake and processing (Bolognesi et al. 2012).

Preparation of UdsRNA longer than about 30 base pairs (bp) has been achieved by in vitro transcription (Timmons 2006) and by fermentation (Fire et al. 1998). Commercially feasible large-scale methods needed for crop protection applications for preparation and purification of the UdsRNA has been described (US Publication No. 20160177299). However, UdsRNAs are sensitive to degradation by nucleases in the environment and the host, reducing efficacy of inhibition of gene expression (Baum 2016).

DsRNA degradation has been addressed in in vitro and in vivo research and for human therapeutics (Ku et al. 2015) by using chemical synthesis of small (<30 bp) interfering dsRNAs (siRNA) with nucleotides modified by chemical means. Preparation of siRNA with chemically modified nucleotides involves sequential protection-deprotection chemical reactions for each nucleotide added in the elongating single strand RNA (ssRNA) chain (Micura 2002). The complexity and expense of such processes are significantly increased for RNA molecules longer than about 30 bp which trigger RNAi (RNAi triggers). While chemically synthesized siRNAs targeting insects using nucleotides chemically modified at the 2'-OH position of the ribose have been also described (Gong et al. 2013), the cost and synthetic complexity of modified siRNAs is neither economically feasible or sufficiently scalable, for preparation of amounts larger than a few grams, or of chemically modified dsRNA longer than about 30 bp.

Post-transcriptional chemical modification of single strand RNA (ssRNA) has been used for analytical purposes, as described in U.S. Pat. No. 6,867,290. SsRNA chemically modified at the 2'-OH position was described as a template to produce UdsRNA in a subsequent step, thereby providing a means for amplification and subsequent detection of minute amounts of unmodified ssRNA. The ssRNA modification was carried out using dimethylsulfoxide (DMSO) as solvent with water present at 5% or less.

Post-transcriptional chemical modification of ssRNA for analytical purposes was also described by Merino (2005). Merino reacted ssRNA in aqueous media containing 10% DMSO with N-methylisatoic anhydride (NMIA) to produce the 2'-O-esters of N-methyl-anthranilic acid at single stranded nucleotides. Derivatization by this method was inefficient. Less than 15% of ssRNA chains in a reaction vessel were modified and those that were modified had, on average, a single 2'-O-ester of NMIA per ssRNA chain. Under these conditions, dsRNA reacted more than 80 times less efficiently, with less than 0.18% of nucleotides in a stem region being modified and only within one (1) nucleotide of the end of a stem (i.e. within one nucleotide of a single strand region) Similar results have been observed for reaction of RNA with other reactants (Nodin 2015). 1-methyl-7-nitroisatoic anhydride (1M7), benzoyl cyanide (BzCN), 2-methyl-3-furoic acid imidazolide (FAI), and 2-methylnicotinic acid imidazolide (NAI) have been used to post-transcriptionally produce 2'-ribose esters of RNA, but have a similarly low percentage of the modification, with modification primarily occurring at riboses of unpaired nucleotides or their immediately adjacent paired nucleotides.

RNAi provides a promising approach to reducing, managing, or controlling pests and weeds in agricultural and urban settings. However, current RNAi technology, using RNAi triggers consisting of UdsRNA or highly modified synthesized siRNA is cost prohibitive for use in agricultural or urban settings. Further, current siRNA production isn't sufficiently scalable. There remains a need for RNAi triggers for agricultural and urban applications that can be economically produced in large scale, stable enough to resist degradation until the point of use, active enough to elicit an effective pesticidal or herbicidal response, and selective enough be considered safe for mammals, humans in particular, and the environment.

SUMMARY

We describe post-transcriptionally chemically modified double strand RNAs (MdsRNAs) comprising: double strand RNAs (dsRNAs) having greater than 30 base pairs and having sense sequences greater than 30 nucleotides in length and antisense sequences greater than 30 nucleotides in length, wherein the sense sequences and antisense sequences are at least 85% complementary, and wherein at least 5% of the dsRNA nucleotides are post-transcriptionally chemically modified. In some embodiments, MdsRNAs have greater than 30, at least 40, at least 50, at least 60, at least 70 at least 80, at least 90, or at least 100 base pairs. In some embodiments, the sense and antisense sequences are independently greater than 30, at least 40, at least 50, at least 60 at least 70, at least 80, at least 90, or at least 100 nucleotides in length. Post-transcriptional chemical modification improves stability of long dsRNA in the environment and during ingestion by some host organisms. The chemical modifications are, however, susceptible to eventual degradation in the environment, thereby reducing negative environmental impact. In some embodiments, MdsRNAs, upon delivery or application to a host organism expressing a target gene, inhibit or knockdown expression of the target gene, through the biological process of RNA interference (RNAi) or other mechanisms. The described MdsRNAs can be economically produced in a readily scalable manner.

In some embodiments, a post-transcriptional chemical modification comprises a ribose 2'OH modification. In some embodiments, ribose 2'OH modifications independently comprises the structure represented by:

[Formula (I)]

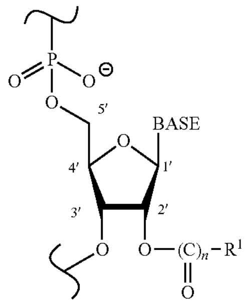

wherein n is 0 or 1, $R^1$ is or comprises a hydrocarbyl or substituted hydrocarbyl, and BASE comprises, independently, a nucleobase, such as, but not limited to: adenine, guanine, cytosine, or uracil (1', 2', 3', 4', and 5' indicate carbon atom positions in a ribose ring).

In some embodiments, $R^1$ can be alkyl, alkenyl, alkynyl, aryl, substituted alkyl, substituted alkenyl, substituted alkynyl, or substituted aryl. In some embodiments, $R^1$ can be a C1-C10 alkyl, C1-C10 alkenyl or C1-C10 alkynyl, wherein alkyl and alkenyl can be linear, branched or cyclic. In some embodiments, $R^1$ can be aryl, substituted aryl, C6-C14 aryl, or C6-C14 substituted aryl. In some embodiments, $R^1$ can be a herterocyclyl, substituted heterocyclyl, C5-C14 heterocyclyl, or substituted C5-C14 heterocyclyl. In some embodiments, $R^1$ can be styryl, C8-C16 substituted styryl, 2-aminophenyl, or substituted 2-aminophenyl. In some embodiments, n=1 and $R^1$ can be N-alkyl-2-aminophenyl or N-aryl-2-aminophenhyl wherein alkyl has the formula $—C_mH_{2m+1}$ (wherein m is an integer less than or equal to 12) and aryl is an aromatic moiety. In some embodiments, $R^1$ can be C2-C12 alkoxyalkyl, C2-C12 alkoxyalkenyl, C2-C12 alkylthioalkyl, alkylsulfonyl, C1-C10 alkylsulfonyl, C1-C10 haloalkyl, C1-C10 haloalkenyl or C1-C10 aminoalkyl. In some embodiments, n=0 and $R^1$ can be a silanyl, substituted silanyl, C1-C10 alkylsilanyl or C3-C12 trialkylsilanyl. In some embodiments, n=0 and $R^1$ can be $—(CH_2CH_2O)_pCH_3$, $—(CH_2CH_2O)_pH$ or $—(CH_2CH_2O)_pCOOR^4$, wherein p is an integer of greater than or equal to 2 and $R^4$ is H, alkyl, substituted alkyl, aryl, or substituted aryl.

In some embodiments, the number of ribose rings chemically substituted at the 2'-OH positions in the MdsRNAs ranges from 5% to 100% of the total number of ribose rings in the MdsRNAs. In some embodiments, the number of ribose rings chemically substituted at the 2'-OH positions in the MdsRNAs is greater than 5%, greater than 10%, greater than 20%, greater than 25%, greater than 30%, greater than 40%, greater than 50%, greater than 60%, greater than 70%, greater than 75%, greater than 80%, or greater than 90% of the total number of ribose rings in the MdsRNAs. The chemically modified nucleotides in the MdsRNA can be random. In other words, chemically modified nucleotides could be adjacent to each other or separated by 1, 2, 3, or more unmodified nucleotides.

Described are readily scalable methods for post-transcriptionally chemically modifying UdsRNAs having greater than 30 base pairs to produce MdsRNAs wherein at least 5% of the dsRNA nucleotides comprise Formula (I). In some embodiments, a UdsRNA post-transcriptional chemical modification process comprises:

(a) forming a mixture comprising an UdsRNA having greater than 30 base pairs in a solution comprising water and an aprotic solvent, (b) adding to the mixture an appropriate amount of:

i) an alkylating agent comprising $R^2—X$ [Formula (II)], where $R^2$ is $R^1$ and X is hydroxyl, halogen, or cyano, or ii) an acylating agent comprising $R^3—X$ [Formula (III)], where $R^3$ is $R^1—(CO)$ and X is H, ONa, chloride, cyanide, alkanoyloxy, or cyclic anhydride, (c) heating the mixture to between about 30° C. and about 95° C. for a period of time necessary for the alkylating agent or acylating agents to react with ribose 2' hydroxyls to form nucleotides comprising Formula (I), thereby forming MdsRNA, and (d) optionally isolating or purifying the MdsRNA comprising modified nucleotides having Formula (I).

In some embodiments, the chemical modification process comprises adding a catalyst during steps (b) and/or (c).

In some embodiments, $R^2$ can be hydrocarbyl or substituted hydrocarbyl, heterocyclyl, silanyl or substituted silanyl, methylsulfonyl. In some embodiments, $R^2$ can be alkyl, alkenyl, alkynyl, aryl, substituted alkyl, substituted alkenyl, substituted alkynyl, or substituted aryl. In some embodiments, $R^2$ can be C1-C10 alkyl, C1-C10 alkenyl, or C1-C10 alkynyl wherein alkyl and alkenyl can be linear, branched or cyclic. In some embodiments, $R^2$ can be aryl or C6-C14 substituted aryl. In some embodiments, $R^2$ can be C5-C14 heterocyclyl. In some embodiments, $R^2$ can be $(CH_2CH_2O)_pCOOR^4$, wherein p is an integer greater than or equal to 2 and $R^4$ is H, alkyl, substituted alkyl, aryl, or substituted aryl.

In some embodiments, $R^3$ can be alkanoyl, substituted alkanoyl, benzoyl, substituted benzoyl, cinnamoyl, substituted cinnalmoyl, anthranoyl, or substituted anthranoyl. In some embodiments, $R^3$ can be C1-C10 alkanoyl or substituted alkanoyl, aroyl or C6-C14 substituted aroyl, cinnamoyl or C8-C16 substituted cinnamoyl, or anthranoyl or substituted anthranoyl. In some embodiments, the cyclic anhydride of Formula (III) can be isatoic anhydride, N-alkylisatoic anhydride, or N-arylisatoic anhydride wherein alkyl has the formula $—C_mH_{2m+1}$ wherein m is an integer less than or equal to 12.

In some embodiments, the alkylating agent of Formula II can be fluoro-2,4-dinitrobenzene (FDNB). In some embodiments, the acylating agent of Formula III can be N-methylisatooic anhydride (NMIA) or benzoyl cyanide (BzCN).

In some embodiments, a MdsRNA contains sequence homology to a target gene expressed in an animal, fungus, or plant. In some embodiments the MdsRNA contains sequence homology to an expressed RNA. In some embodiments, the MdsRNA inhibits expression of the target gene.

In some embodiments, we describe methods for post-transcriptionally chemically modifying a double strand RNA to form a MdsRNA comprising, a) forming an unmodified dsRNA (UdsRNA) mixture comprising an unmodified double strand RNA having greater than 30 base pairs in a solution comprising water and an aprotic solvent,
b) heating said UdsRNA mixture to about between 30-95° C.,
c) heating a reactant to about 30-95° wherein the reactant is selected from the group consisting of:
  i) an alkylating agent comprising $R^2$—X [Formulae (II)], where $R^2$ is $R^1$ and X is hydroxyl, halogen, cyano, or
  ii) an acylating agent comprising $R^3$—X [Formulae (III)], where $R^3$ is $R^1$—(CO)— and X is OH, ONa, OK, chloride, cyanide, imidazolide, alkanoyloxy, or
d) adding the reactant to the UdsRNA mixture,
e) heating the combined UdsRNA mixture and reactant to about 30-95° C. for a period of time necessary for the reactant to chemically modify ribose 2' hydroxyls to form nucleotides comprising Formula (I), thereby forming the MdsRNA, and
f) optionally isolating or purifying the MdsRNA.

In some embodiments, a target gene is selected such that inhibiting expression of the target gene kills, inhibits growth or appetite of, or slows reproduction of an animal, fungus, or weed. Inhibiting expression of the target gene can control, kill, inhibit growth or appetite of, or slow reproduction of the animal, fungus, or weed. In some embodiments, the insect, fungus, or plant is of agricultural significance. In some embodiments, an agriculturally significant animal, fungus, or plant is an insect, fungus, or weed. An insect can be, but is not limited to: Coleopteran (such as a beetle), Lepidopteran (such as a butterfly or moth), Hymenopteran (such as sawflies, wasps, bees, and ants), Dipteran (such as a fly), or Hemipteran (such as a true bug). A fungus can be, but is not limited to: a Hypocrealesan. A weed is a plant considered undesirable in a particular situation or location. A weed can be, but is not limited to, Palmer Amaranth, Common Lambsquarters, Horseweed, Morning Glory, Waterhemp, Nutsedge, *Kochia*, Common Ragweed, Giant Ragweed, or Nightshade. In some embodiments, the described MdsRNAs can be used to control, kill, inhibit growth, appetite, or feeding of, or slow reproduction of an animal, fungus, or plant in an agricultural or urban setting.

In some embodiments, a plant target gene is selected such that inhibiting expression of the gene in the plant increases plant growth, viability, quality, or yield.

Described are methods for making MdsRNAs suitable for inhibiting expression of a target gene in an animal, fungus, or plant comprising:

a) identifying a target gene in a host animal, fungus, plant
b) making an expression vector for expressing dsRNAs having at least 30 base pairs wherein the dsRNAs comprise sequence homology to the target gene,
c) using the expression vector to produce UdsRNA transcripts,
d) post-transcriptionally modifying the transcripts to produce MdsRNAs, and
e) optionally purifying the MdsRNAs.

In some embodiments, the methods can be used in the large-scale manufacture of MdsRNAs. Large scale production (transcription) of UdsRNAs can be accomplished using methods available in the art, including, but not limited to: in vitro transcription (Krieg et al. 1987), fermentation in reactors using bacteria or yeasts expression systems (Fire et al. 1998), using plant expression systems, and/or coupling transcription of the desired polynucleotide with expression of self-assembling bacteriophage capsid proteins, such as those of bacteriophage Qf3 or MS2 (US20160208221 and US20140302593). The UdsRNAs can then be chemically modified as described. In some embodiments, UdsRNAs in Qf3 or MS2 virus-like particles can be chemically modified.

In some embodiments, we describe compositions containing the described MdsRNAs. In some embodiments, the MdsRNA-containing compositions are formulated for agricultural application. In some embodiments, MdsRNAs are combined with or present in a composition containing one or more agents selected from the group comprising: excipient, carrier, herbicide, fungicide, insecticide, fertilizer, solvent, surfactant, binder, filler, wetting agent, thickening agent, foam control agent, dispersant, disintegrant, pH regulating agent, chelating agent, preservative, and pigment. In some embodiments, the MdsRNAs comprise less than 50% by weight of the composition.

In some embodiments, we provide methods for treating, controlling, limiting, or reducing infestation (e.g., by insect, fungus, or weed infestation), the methods comprising applying a composition containing one or more of the described MdsRNAs to an area of infestation of potential infestation. The area of infestation or potential infestation can be an agricultural setting. Agricultural settings include, but are not limited to, fields, orchards, and livestock operations. Inhibiting expression of a target gene in the insect, fungus, or weed in an agricultural area can reduce crop damage or decreased yield caused by the insect, fungus, or plant compared with the damage or decreased yield as measured in the absence of treatment with MdsRNAs.

In some embodiments, we describe methods of reducing expression of a target gene in a plant, including, but not limited to, an agricultural crop plant, the methods comprising applying a composition containing one or more of the described MdsRNAs to the plant. The plant can be in a laboratory, greenhouse, nursery, field, orchard or other agricultural setting, or another natural setting.

In some embodiments, a composition containing a described MdsRNA is applied to a field, such as by spraying. In some embodiments, a composition containing a described MdsRNA is applied to a plant surface upon which an insect or fungus feeds. Once ingested, the described MdsRNA can be absorbed by cells lining the gut of the pest and processed generate effective RNAi triggers targeted against the host target gene transcripts to suppress expression of the target gene.

Figure 1:
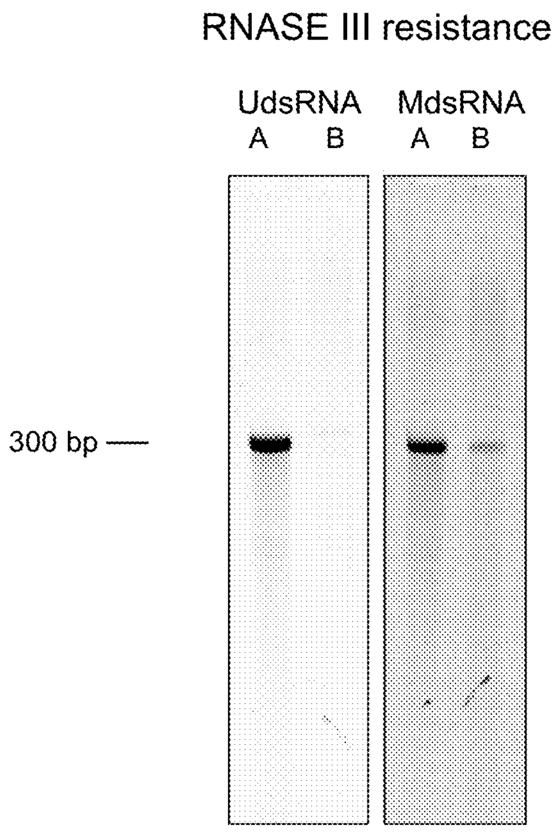
FIG. 1. Image showing increased resistant to digestion by RNase III of MdsRNAs compared to UdsRNA. UdsRNA was modified by BzCN to generate MdsRNA in which about 40% of the nucleotides were modified. UdsRNA and MdsRNA were then treated with RNase III. UdsRNA and MdsRNA samples before (lanes A) and after (lanes B) RNase III digestion were then electrophoresed and visualized by ethidium bromide staining.

A. 1,6-Dibenzyl-1,3a,6,8-tetraaza-1,2,3,4,5,6-hexahydrophenalene (BnsDMAP),

B. 1,6-Diethyl-1,3a,6,8-tetraaza-1,2,3,4,5,6-hexahydrophenalene (EtsDMAP), and

C. 1,6-Dimethyl-1,3a,6,8-tetraaza-1,2,3,4,5,6-hexahydrophenalene (MesDMAP).

DETAILED DESCRIPTION

We describe MdsRNAs having greater than 30, at least 40, at least 50, at least 70, at least 80, at least 90, or at least 100 base pairs wherein at least 5% of the ribose rings are post transcriptionally chemically modified at the 2'-OH position. We also describe compositions comprising MdsRNAs and methods of making and using MdsRNAs. The MdsRNAs are capable of inhibiting gene expression in a sequence specific manner, such as through RNA interference or antisense mechanisms, in agriculturally significant pests, such as insects, fungi, and/or plants. Also described are processes for post-transcriptional modification of unmodified double strand RNA (UdsRNA). We further describe methods of inhibiting or controlling pests in an agricultural or urban setting using compositions containing the MdsRNAs.

An MdsRNA comprises dsRNA having a sense strand and an antisense strand wherein the dsRNA comprises at least 30 base paired nucleotides (base pairs) and wherein at least 5% of the nucleotide riboses are post-transcriptionally modified.

In some embodiments, a MdsRNA is at least 40, at least 50, at least 70, at least 80, at least 90, or at least 100 base pairs in length. A MdsRNA sense strand contains a sense sequence and a MdsRNA antisense strand contains an antisense sequence. The antisense sequence is 100% (perfectly) complementary or at least 90% (substantially) complementary or at least 80% (partial) complementary to a nucleotide sequence present in a target gene transcribed mRNA or non-coding RNA (i.e., expressed RNA). The sense sequence is 100% (perfectly) complementary or at least 90% (substantially) complementary or at least 80% (partially) complementary the antisense sequence. A sense sequence may also be 100% identical, at least 90% identical, or at least 80% identical to a nucleotide sequence (target sequence) present in a target gene mRNA or non-coding RNA. The sense sequence and a corresponding antisense sequence are partially (at least 80%), substantially (90%), or fully (100%) complementary to each other. In some embodiments, the region of complementarity (antisense sequence) or identity (sense sequence) between the MdsRNA and a corresponding sequence in the target gene transcribed mRNA or non-coding RNA sequence is greater than 30, at least 40, at least 50, at least 60, at least 70, at least 80, at least 90, or at least 100 nucleotides in length. In some embodiments, the antisense sequence contains a contiguous sequence greater than 30, at least 40, at least 50, at least 60, at least 70, at least 80, at least 90, or at least 100 nucleotides in length that is 100% complementary or at least 80% complementary to a corresponding contiguous sequence in the target gene transcribed mRNA or non-coding RNA. MdsRNA sense and antisense sequences can be either the same length or they can be different lengths. Suitable sense and antisense sequences are identified using known methods readily available in the art.

In some embodiments, a MdsRNA sense strand is connected to the antisense strand. A sense strand can be connected to an antisense strand via a non-hybridizing hairpin or loop sequence. A loop sequence can be about 4 to 100 or more nucleotides in length. In some embodiments, a loop is 150 or more nucleotides in length (Hauge et al. 2009). In some embodiments, a MdsRNA further comprises one or more additional sequences including, but not limited to: promoter sequences, 5' sequences, 3' sequences, terminator sequences, and polyA sequences.

A promoter is a region (sequence) of DNA that initiates transcription of a gene. A promoter can be a bacterial promoter, archaea promoter, eukaryotic promoter, or a Pol I, Pol II, or Poll III promoter. In some embodiments, a bacterial promoter comprises the sequence 5'-TTGACA-3' about 35 bp upstream from the transcription start site and the sequence 5'-TATAAT-3' about 10 bp upstream from the transcription start site. Other promoters, suitable for use with different expression systems are well known in the art.

MdsRNA

In some embodiments, more than 5% of the base-paired nucleotides of a MdsRNA are post-transcriptionally chemically modified at ribose 2'-OH positions. In some embodiments, the nucleotides contain substitutions at ribose 2'-OH positions. In some embodiments, the described MdsRNAs contain nucleotides chemically substituted at the backbone ribose 2'-OH position wherein the chemically substituted nucleotides independently comprise Formula (I):

[Formula (I)]

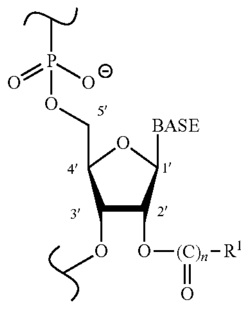

wherein n is 0 or 1, $R^1$ is or comprises a hydrocarbyl or substituted hydrocarbyl, and BASE comprises, independently, a nucleobase, such as, but not limited to: adenine, guanine, cytosine, or uracil (1', 2', 3', 4', and 5' indicate carbon atom positions in a ribose ring).

In some embodiments, $R^1$ can be alkyl, substituted alkyl, alkenyl, substituted alkenyl, alkynyl, substituted alkynyl, aryl, or substituted aryl. In some embodiments, $R^1$ can be C1-C10 alkyl, C1-C10 alkenyl, or C1-C10 alkynyl wherein alkyl and alkenyl can be linear, branched or cyclic. In some embodiments, $R^1$ can be methyl, ethyl, propyl, isopropyl, butyl, isobutyl, tert-butyl, pentyl, hexyl, cyclohexyl, heptyl, octyl, nonyl, decyl, vinyl, allyl, ethynyl, benzyl, cinnamyl, or the like. In some embodiments, $R^1$ can be C6-C14 aryl or C6-C14 substituted aryl. In some embodiments, $R^1$ can be heterocyclyl or C5-C14 heterocyclyl. In some embodiments, n=0 and $R^1$ can be phenyl, mono or disubstituted phenyl wherein the substituents are selected from C1-C10 alkyl, C1-C10 alkenyl, C1-C6 alkoxy, halogen, nitro, methylsulfonyl, and trifluoromethyl. In some embodiments, n=0 and $R^1$ can be 2-nitrophenyl, 4-nitrophenyl, 2,4-dinitrophenyl, 2-trifluromethylphenyl or 4-triflouromethylphenyl. In some embodiments, $R^1$ can be, styryl, or C8-C16 substituted styryl. In some embodiment, n=1 and R1 is hydrogen. In some embodiments, n=1 and $R^1$ can be phenyl, mono or disubstituted phenyl 2-aminophenyl, or mono or disubstituted 2-aminophenyl, wherein the substituents are selected from C1-C10 alkyl, C1-C10 alkenyl, C1-C6 alkoxy, halogen, nitro, methylsulfonyl, and trifluoromethyl. In some embodiments, n=1 and $R^1$ can be N-alkyl-2-aminophenyl or N-aryl-2-aminophenyl wherein alkyl has the formula $-C_mH_{2m+1}$ (wherein m is an integer less than or equal to 12) and aryl is an aromatic moiety. In some embodiments, n=1 and $R^1$ can be 2-amino-3-methyl-phenyl, 2-amino-5-chlorophenyl, 2-methyl-5-chlorophenyl, N-methyla-2-minophenyl, N-ethyl-2-aminophenyl, N-propyl-2-aminophenyl, N-butyl2-aminophenyl, N-pentyl-2-aminophenyl, N-methyl-2-amino-4-nitrophenyl, 2-methyl-3-furyl, 2-methylnicotyl or N-trifluoromethyl-2-aminophenyl. In some embodiments, n=0 and $R^1$ can be a silanyl, substituted silanyl, C1-C10 alkylsilanyl or C3-C12 trialkylsilanyl. In some embodiments, $R^1$ can be C2-C12 alkoxyalkyl, C2-C12 alkoxyalkenyl, C2-C12 alkylthioalkyl, alkylsulfonyl, C1-C10 alkylsulfonyl, C1-C10 haloalkyl, C1-C10 haloalkenyl or C1-C10 aminoalkyl. C1-C10 includes C1, C2, C3, C4, C5, C6, C7, C8, C9, and C10. Similarly, C2-C12 includes C2, C3, C4, C5, C6, C7, C8, C9, C10, C11, and C12. Likewise, C5-C14, C6-C14, C8-C16, C3-C12 includes each individual possible formula with the given range.

In some embodiments, n=0 and $R^1$ can be $-(CH_2CH_2O)_pCH_3$, $-(CH_2CH_2O)_pH$ or $-(CH_2CH_2O)_pCOOR^4$, wherein p is an integer greater than or equal to 2 and $R^4$ is H, alkyl, substituted alkyl, aryl, or substituted aryl. In some embodiments, p may range from 2 to 8. In some embodiments, $R^1$ can be $-(CH_2CH_2O)_8COOH$, $-CH_2CH_2OH$, $-(CH_2CH_2O)_4OH$, $-(CH_2CH_2O)_6OH$, $-(CH_2CH_2O)_8OH$, $-(CH_2CH_2O)_8COOMe$, $-(CH_2CH_2O)_4OMe$, $-(CH_2CH_2O)_6OMe$, $-(CH_2CH_2O)_8OMe$, $-CH_2OCH_3$, $-CH_2OCH_2CH_3$, or $-CH_2OCH_2CH_2OCH_3$.

In some embodiments, greater than 10%, greater than 20%, greater than 25%, greater than 30%, greater than 40%, greater than 50%, greater than 60%, greater than 70%, greater than 75%, greater than 80%, or greater than 90% of the ribose rings of a MdsRNA are substituted at the 2'-OH position. In some embodiments, 5-95%, 10-95%, 20-95%, 30-95%, 40-95%, 50-95%, 60-95%, 70-95%, 80-95%, 90-95%, 10-90%, 10-80%, 10-70%, 10-60%, 10-50%, 10-40%, 0-30%, or 10-25% of the ribose rings of a MdsRNA are substituted at the 2'-OH position.

In some embodiments, we describe MdsRNA constructs having a hydrophobic moiety containing chemical modification at one or more 2'-OH groups of the ribose rings in the dsRNA. The hydrophobic moieties increase the lipophilic character of the MdsRNAs resulting in an increase in their solubility in organic solvents and a decrease of their solubility in water. We have observed MdsRNAs containing 40% of the ribose rings chemically modified with benzoyl groups that are 30% less soluble in water than the corresponding UdsRNA. The increase in hydrophobicity may increase or enhance diffusion of the MdsRNA across biological membranes. Increased diffusion may improve target gene knockdown in the pest host at lower concentrations, thus reducing overall application costs.

In some embodiments, the calculated octanol/water partition coefficient (Kow) or HLB for the chemically modified dsRNA construct of Formula I is increased. Some MdsRNAs containing 40% of the ribose rings chemically modified with benzoyl groups had a greater than 15-fold increase in Kow compared to the corresponding UdsRNAs. Some MdsRNAs containing 40% of the ribose rings chemically modified with N-methylanthranil groups had a greater than 30-fold increase in Kow as compared to the corresponding UdsRNAs. The expected diffusion rate of the chemically modified dsRNA across biological membranes is higher. Higher diffusion is expected to lead to increase efficacy and of the MdsRNAs in inhibiting gene expression.

In some embodiments, the described MdsRNAs are more stable that their corresponding unmodified dsRNAs. Increased stability may reduce degradation of the MdsRNAs by host or environmental ribonucleases thus improving delivery and/or effectiveness.

In some embodiments, the described MdsRNA constructs have improved stability against degradation by double-stranded ribonucleases.

In some embodiments, the described MdsRNAs inhibit or knockdown target gene expression in a host organism. Inhibiting target gene expression can lead to decreased survival of the host organism. In some embodiments, inhibiting target gene expression can lead to improved growth, vigor, disease resitance, viability, drought tolerance, etc. of a host organism. In some embodiments, ingestion of MdsRNAs by a host leads to inhibition of target gene expression. Without being bound by theory, it is believed that ingested MdsRNAs may be processed by host cellular machiney into RNAi triggers which then inhibit gene express through RNA interference.

A person skilled in the art will understand that the teachings of the present invention could be applied to improve the stability of ssRNA useful in the preparation of aptamers, antisense, mRNA, and other long RNAs. A person skilled in the art will understand that the teachings of the present invention could be applied to improve the stability of RNA useful in the preparation of human or animal antiparasitic active ingredients indicated for the treatment of parasitic diseases, such as those caused by helminths, amoeba, ectoparasites, parasitic fungi, or protozoa, among others.

Post-Transcription Modification of UdsRNAs

We describe reacting UdsRNAs with suitable chemical reactants under suitable ranges of reaction conditions such that the chemical reactants react with enough hydroxyls in the 2'-OH positions of the riboses to produce the described MdsRNAs. The described preparations provide improved efficacy and are scalable. They can be performed in large enough volumes to be economically manufactured for agricultural and/or urban uses.

In some embodiments, post-transcriptional modification of UdsRNA to form MdsRNA comprising Formula (I) comprises:

(a) contacting the desired UdsRNA with a solvent mixture containing water and an aprotic solvent at a temperature between about 30° C. and about 80° C., (b) optionally contacting the UdsRNA solvent mixture with a catalyst, (c) contacting the mixture with a chemical reactant selected from:

(i) an alkylating agent comprising $R^2$—X [Formula (II)], or (ii) an acylating agent comprising $R^3$—X [Formula (III)], and (c) optionally contacting the UdsRNA solvent mixture with one or more catalysts, (d) heating to between about 30° C. and about 95° C. for a period of time necessary for the reactants to modify the UdsRNA to the desired extent thereby forming the MdsRNA.

Suitable aprotic solvents include, but are not limited to: DMSO, DMF, dimethylacetamide, THF, dioxane, acetonitrile, and urea. The percentage of aprotic solvent in the solvent mixture can be 40% to 95%, about 40%, about 45%, about 50%, about 55%, about 60%, about 65%, about 70%, about 75%, about 80%, about 85%, about 90%, or about 95%. The temperature of the solvent mixture varies between about 30° C. to about 80° C., or between about 50° C. to about 70° C., or between about 60° C. to about 70° C.

Suitable catalysts include, but are not limited to: DMAP (dimethylaminopyridine), 1,6-Dibenzyl-1,3a,6,8-tetraaza-1,2,3,4,5,6-hexahydrophenalene (BnsDMAP), 1,6-Diethyl-1,3a,6,8-tetraaza-1,2,3,4,5,6-hexahydrophenalene (EtsDMAP), 1,6-Dimethyl-1,3a,6,8-tetraaza-1,2,3,4,5,6-hexahydrophenalene (MesDMAP (Rycke et al. 2010)), amidines, isothioureas, guanidines, sodium carbonate, sodium bicarbonate, potassium carbonate, potassium bicarbonate, N,N'-dicyclohexylcarbodiimide (DCC), N-(3-dimethylaminopropyl)-N-ethylcarbodiimide hydrochloride (EDC), 1-hydroxy-benzotriazole (HOBt), and 1-hydroxy-7-azabentriazole (HOAt).

In some embodiments, $R^2$ of Formula (II) is $R^1$. In some embodiments, $R^2$ of Formula (II) can be, but is not limited to, alkyl, alkenyl, alkynyl, aryl, substituted alkyl, substituted alkenyl, substituted alkynyl, substituted aryl, C1-C10 alkyl, C1-C10 alkenyl, C1-C10 alkynyl, aryl, substituted C6-C14 aryl, C5-C14 heterocyclyl, or $(CH_2CH_2O)_pCOOR^4$ wherein p is an integer greater than or equal to 2 and $R^4$ is H, alkyl, substituted alkyl, aryl, or substituted aryl. Alkyl and alkenyl can be linear, branched or cyclic. In some embodiments, X of Formula (II) can be, but is not limited to, hydroxyl, halogen, or cyano.

In some embodiments, suitable alkylating agents of Formula (II) include, but are not limited to: ethyl chloride, propyl chloride, butyl chloride, benzyl chloride, 1-fluoro-2-nitrobenzene, 1-fluoro-4-nitrobenzene, 1-fluoro-2,4-dinitrobenzene, chloro-2,4-dinitrobenzene, fluoro-2-triflurommethylphenyl, fluoro-4-triflouromethylphenyl, ethyl alcohol, n-butyl bromide, octane nitrile, 4-bromo anisole, cinnamyl alcohol, and trimehylsilyl chloride.

In some embodiments, $R^3$ of Formula (III) is $R^1$—(CO). In some embodiments, $R^3$ of Formula (III) can be, but is not limited to, C1-C10 alkanoyl, substituted alkanoyl, benzoyl, aroyl, C6-C14 substituted aroyl, cinnamoyl, C8-C16 substituted cinnamoyl, anthranoyl, or substituted anthranoyl. In some embodiments, X of Formula (III) can be, but is not limited to, H, ONa, chloride, cyanide, alkanoyloxy, or cyclic anhydrides. Suitable anhydrides include, but are not limited to, isatoic anhydride, substituted isatoic anhydride, N-alkylisatoic anhydride, and N-arylisatoic anhydride wherein alkyl has the formula $—C_mH_{2m}+1$ and wherein m is an integer greater than or equal to 5 and aryl is an aromatic moiety.

In some embodiments, suitable acylating agents of Formula (III) include, but are not limited to, formyl chloride, acetyl chloride, butanoyl chloride, pivaloyl chloride, benzoyl chloride, benzoyl cyanide, acetic anhydride, propionic anhydride, butyric anhydride, valeric anhydride, N-methylisatoic anhydride (NMIA), N-ethylisatoic anhydride, N-propylisatoic anhydride, N-butylisatoic anhydride, N-pentylisatoic anhydride, 1-methyl-7-nitroisatoic anhydride, N-trifluoromethylisatoicanhydride, 3-methylisatoic anhydride, 5-chloroisatoic anhydride, 5-chloroisatoic anhydride, 2-methyl-3-furoic acid imidazolide, and 2-methylnicotinic acid imidazolide.

In some embodiments, a mole ratio of UdsRNA to alkylating or acylating agent ranges from about 1:3 to about 1:300. In some embodiments, a mole ratio of UdsRNA to alkylating or acylating agent ranges from about 1:3 to about 1:10, about 1:10 to about 1:50, about 1:50 to about 1:100, or about 1:100 to about 1:200.

In some embodiments, a UdsRNA is reacted with NMIA in a solvent mixture comprising between 15% an 90% dimethyl sulfoxide at a temperature range between 40° C. and 70° C. for about 30 min.

In some embodiments, a UdsRNA is reacted with BzCN in a solvent mixture comprising between 15% an 90% dimethyl sulfoxide at a temperature range between 40° C. and 70° C. for about 30 min.

In some embodiments, a UdsRNA is reacted with FDNB in a solvent mixture comprising between 15% an 90% dimethyl sulfoxide at a temperature range between 40° C. and 70° C. for about 30 min.

In some embodiments, a UdsRNA is reacted with BzCN in a solvent mixture comprising between 15% an 90% dimethyl sulfoxide at a temperature range between 40° C. and 70° C. for about 30 min.

In some embodiments, a catalyst is added to the UdsRNA, which is then reacted with NMIA, BzCN, or FDNB in a solvent mixture comprising between 15% an 90% dimethyl sulfoxide at a temperature range between 40° C. and 70° C. for about 30 min.

In some embodiments, a catalyst is added after having added NMIA, BzCN, or FDNB to a UdsRNA in a solvent mixture comprising between 15% an 90% dimethyl sulfoxide at a temperature range between 40° C. and 70° C. for about 30 min.

In some embodiments, a DMAP is added after having added NMIA or BzCN, to a UdsRNA in a solvent mixture comprising between 15% an 90% dimethyl sulfoxide at a temperature range between 40° C. and 70° C. for about 30 min.

In some embodiments, a potassium carbonate is added after having added FDNB to a UdsRNA in a solvent mixture comprising between 15% an 90% dimethyl sulfoxide at a temperature range between 40° C. and 70° C. for about 30 min.

In some embodiments, a mixture after reaction containing MdsRNAs is rapidly cooled to about 25° C. and water or another suitable solvent is rapidly added afterwards.

In some embodiments, a mixture after reaction containing MdsRNAs is gradually cooled to about 25° C. over a period of time longer than 30 minutes and water or another suitable solvent is added afterwards over a period of time longer than 30 min.

In some embodiments, chemically derivatized RNA molecules constituting MdsRNAs are isolated and purified. MdsRNA can be optionally isolated purified by precipitation, extraction, extraction with a partially miscible solvent, ultrafiltration adsorption, other methods known in the art, or a combination thereof.

In some embodiments, a mixture at about 25° C. containing MdsRNA after dilution with water is further cooled to about 4° C. and an insoluble fraction containing MdsRNA is optionally recovered by filtration, decantation, extraction with a partially miscible solvent, centrifugation, ultrafiltration, or a combination thereof.

In some embodiments, a mixture at about 25° C. containing MdsRNA after dilution with ethanol, methanol or a mixture of alcohols is further cooled to about 20° C. and an insoluble fraction containing MdsRNA is optionally recovered by filtration, decantation, extraction with a partially miscible solvent, centrifugation, ultrafiltration, or a combination thereof.

The methods described herein here can be modified to target different genes in different hosts by modifying the sequences from those described in the examples to reflect the sequences of the targeted genes in the targeted host organisms. Thus, examples described provide those skilled in the art with a tool for obtaining the best RNAi effect for suppressing a particular gene in any given host cell and a means for producing large quantities of such RNAi triggers.

MdsRNAs Suitable for Inhibition of Genes in Host Organisms

We describe methods of forming MdsRNAs suitable for inhibition of expression of a target gene in a host organism comprising:

a) identifying a target gene expressing a mRNA or a non-coding RNA in the host organism,
b) making an expression vector for expressing a UdsRNAs having a sequence complementary to a sequence in the expressed RNA,
c) producing UdsRNA transcripts,
d) post-transcriptionally modifying the transcripts to produce MdsRNAs, and
e) optionally purifying the MdsRNAs.

In some embodiments, we describe methods of producing a composition for inhibiting expression of a target gene in a host comprising:

a) selecting the target gene wherein the target gene expresses an RNA in the host,
b) producing dsRNA transcripts encoding at least a portion of the sequence of the expressed RNA,
c) post-transcriptionally chemically modifying the dsRNA transcripts to form MdsRNAs capable of inhibiting expression of the target gene, and
d) optionally purifying the MdsRNAs.

In some embodiments, the host organism can be an agricultural pest. An agricultural pest can be, but is not limited to, an animal, fungus, or plant that has or has the potential to have a negative impact on an agricultural product, on production of the agricultural product, or on an animal or human population. An agricultural pest can be, but is not limited to, an insect, fungus, or weed. A negative impact can be a reduction of crop yield or product yield or transmission or spread of disease, or lower quality fruit or vegetables.

In some embodiments, the target gene is a gene necessary for growth or reproduction of the agricultural pest. Examples of such essential genes include, but are not limited to, genes involved in controlling molting or other larval development events, actin or other cellular structural components, as well as virtually any gene essential to viability of the target pest.

In some embodiments, an expression vector is used to generate an RNA transcript. Expression vectors for expressing UdsRNAs are well known in the art. An expression vector can express an RNA having a sense sequence, and antisense sequence, or both a sense sequence and antisense sequence. Expression vectors for expressing sense sequences are frequently paired with expression vectors for expressing complementary or corresponding antisense sequences. In some embodiments, sense and antisense vectors can be transcribed separately and the RNA transcripts subsequently combined under conditions that allow base pairing of the sense and antisense sequences. Expression vectors for expressing both sense and antisense sequences can express separate transcripts containing the sense and antisense sequences. In some embodiments, expression vectors for expressing both sense and antisense sequences can express both the sense and antisense sequences on a single transcript. Transcripts containing both sense and antisense sequences contain hairpin or loop sequences.

In addition to the sense and antisense sequences, expression vectors typically contain promotor sequences and terminator sequences. Expression vectors can also contain additional transcribed 5' and 3' sequences. Expression vectors can also contain sequences that aren't transcribed into the desired RNA, but are used to assist in cloning (e.g., multiple cloning site), or facilitate replication (e.g., origin of replication), selection (ampicillin resistance) or phage packaging.

In some embodiments, the sense sequence is designed to be less the 100% complementary to the antisense sequence. The sense strand can have insertions, deletions, mismatches, or a combination of insertions, deletions, or mismatches. In some embodiments, a sense sequence contains an additional nucleotide (insertion) every 5-33 nucleotides. In some embodiments, a sense sequence contains an additional dinucleotide (insertion) every 5-33 nucleotides. In some embodiments, a sense sequence contains a deleted nucleotide (deletion) every 5-33 nucleotides. In some embodiments, a sense sequence contains a mismatch mutation every 5-33 nucleotides.

In some embodiments, DNA sequences for use in producing UdsRNAs are described. The described DNA sequences encode different antisense sequences based on different host animal, fungus, or plant expressed target genes. UdsRNA produced from the DNA sequences are modified to form MdsRNAs. The MdsRNAs can then be purified and fed or applied to host animals, fungi, or plants resulting in decreased expression of the target gene in the host.

DNA sequences for producing UdsRNAs encoding antisense sequences having complementarity to other target genes are readily produced using knowledge and techniques available in the art.

Post transcription modification of the UdsRNA, and purification of the MdsRNA is as described above.

Formation of UdsRNA for modification and use as described can be done by any means typical in the art. Exemplary methods of producing RNA transcriptions include, but are not limited to, in vitro transcription (Timmons 2006), fermentation using expression in archaea, bacteria, yeast, plant, or mammalian cells (Fire et al. 1998), and/or coupling transcription of the desired polynucleotide with expression of self-assembling bacteriophage capsid proteins, such as those of bacteriophage Qβ or MS2 (US20160208221 and US20140302593). Commercially feasible large-scale methods needed for crop protection applications for preparation and purification of the UdsRNA has been described (US Publication No. 20160177299). The UdsRNAs can then be chemically modified as described.

In some embodiments, the methods can be used in the large-scale manufacture of MdsRNAs. In some embodiments, large-scale manufacture means in amounts exceeding 1 gram. In some embodiments, large-scale manufacture means in amounts exceeding 1 kilogram. In some embodiments, large-scale manufacture means in amounts exceeding 100 kilograms. In some embodiments, large-scale manufacture means in amounts exceeding 1 metric ton.

Agricultural/Agrochemical Compositions

In some embodiments, we describe compositions containing the described MdsRNAs. In some embodiments, the MdsRNA-containing compositions are formulated for agricultural application (agrochemical compositions).

As used herein, an agrochemical composition comprises an effective amount of at least one MdsRNA and optionally one or more acceptable carriers or excipients. Carriers and excipients are substances other than the MdsRNA that have been appropriately evaluated for safety and are intentionally included in a composition. Excipients may act to a) aid in processing of the MdsRNA during manufacture, b) protect, support or enhance stability, or bioavailability of the MdsRNA, c) assist in product identification, and/or d) enhance any other attribute of the overall safety, effectiveness, of delivery of the MdsRNA during storage or use. An acceptable carrier or excipient may or may not be an inert substance. As used herein, “effective amount,” refers to that amount of a MdsRNA to produce the intended result.

Carrier and excipients include, but are not limited to: absorption enhancers, anti-adherents, anti-foaming agents, anti-oxidants, binders, binders, buffering agents (pH regulating agents), chelating agents, coating agents, colors, delivery enhancers, dextran, dextrose, diluents, disintegrants, dispersants, emulsifiers, extenders, fillers, foam control agents, glidants, humectants, lubricants, oils, pigments, polymers, preservatives, saline, salts, solvents, sugars, surfactants, suspending agents, sustained release matrices, sweeteners, thickening agents, tonicity agents, vehicles, water-repelling agents, and wetting agents.

In some embodiments, an agrochemical composition comprises one or more agents selected from the group comprising: herbicide, fungicide, insecticide, and fertilizer.

The described MdsRNAs and compositions containing MdsRNAs can be processed in a number of different ways known to those skilled in the art to facilitate application of such material onto plants or into baits and for use in the field or in urban environments. The described MdsRNAs and compositions comprising MdsRNAs disclosed herein can be packaged or included in a kit, container, pack, or dispenser.

In some embodiments, an agrochemical composition contains two or more different MdsRNAs. The MdsRNAs may have different antisense sequences complementary to the same target gene, different antisense sequences complementary to different target genes in the same or different hosts, different or similar lengths, and different or similar post transcriptional modification.

In some embodiments, an agrochemical composition is an emulsifiable agricultural concentrate. In some embodiments, an emulsifiable agricultural concentrate further contains a least one agent that can be, but is not limited to; carrier, excipient, herbicide, fungicide, insecticide, fertilizer, or combinations thereof.

In some embodiments, an agrochemical composition contains one or more herbicides. Non-limiting examples of suitable herbicides include, but are not limited to, imidazolinone, acetochlor, acifluorfen, aclonifen, acrolein, AKH-7088, alachlor, alloxydim, ametryn, amidosulfuron, amitrole, ammonium sulfamate, anilofos, asulam, atrazine, azafenidin, azimsulfuron, BAS 620H, BAS 654 00H, BAY FOE 5043, benazolin, benfluralin, benfuresate, bensulfuron-methyl, bensulide, bentazone, benzofenap, bifenox, bilanafos, bispyribac-sodium, bromacil, bromobutide, bromofenoxim, bromoxynil, butachlor, butamifos, butralin, butroxydim, butylate, cafenstrole, carbetamide, carfentrazone-ethyl, chlormethoxyfen, chloramben, chlorbromuron, chloridazon, chlorimuron-ethyl, chloroacetic acid, chlorotoluron, chlorpropham, chlorsulfuron, chlorthal-dimethyl, chlorthiamid, cinmethylin, cinosulfuron, clethodim, clodinafop-propargyl, clomazone, clomeprop, clopyralid, cloransulam-methyl, cyanazine, cycloate, cyclosulfamuron, cycloxydim, cyhalofop-butyl, 2,4-D, daimuron, dalapon, dazomet, 2,4DB, desmedipham, desmetryn, dicamba, dichlobenil, dichlorprop, dichlorprop-P, diclofop-methyl, difenzoquat metilsulfate, diflufenican, dimefuron, dimepiperate, dimethachlor, dimethametryn, dimethenamid, dimethipin, dimethylarsinic acid, dinitramine, dinocap, dinoterb, diphenamid, diquat dibromide, dithiopyr, diuron, DNOC, EPTC, esprocarb, ethalfluralin, ethametsulfuron-methyl, ethofumesate, ethoxysulfuron, etobenzanid, fenoxaprop-P-ethyl, fenuron, ferrous sulfate, flamprop-M, flazasulfuron, fluazifop-butyl, fluazifop-P-butyl, fluchloralin, flumetsulam, flumiclorac-pentyl, flumioxazin, fluometuron, fluoroglycofen-ethyl, flupoxam, flupropanate, flupyrsulfuron-methyl-sodium, flurenol, fluridone, flurochloridone, fluroxypyr, flurtamone, fluthiacet-methyl, fomesafen, fosamine, glufosinate-ammonium, glyphosate, glyphosinate, halosulfuron-methyl, haloxyfop, HC-252, hexazinone, imazamethabenz-methyl, imazamox, imazapyr, imazaquin, imazethapyr, imazosuluron, imidazilinone, indanofan, ioxynil, isoproturon, isouron, isoxaben, isoxaflutole, lactofen, lenacil, linuron, MCPA, MCPA-thioethyl, MCPB, mecoprop, mecoprop-P, mefenacet, metamitron, metazachlor, methabenzthiazuron, methylarsonic acid, methyldymron, methyl isothiocyanate, metobenzuron, metobromuron, metolachlor, metosulam, metoxuron, metribuzin, metsulfuron-methyl, molinate, monolinuron, naproanilide, napropamide, naptalam, neburon, nicosulfuron, nonanoic acid, norflurazon, oleic acid (fatty acids), orbencarb, oryzalin, oxadiargyl, oxadiazon, oxasulfuron, oxyfluorfen, paraquat dichloride, pebulate, pendimethalin, pentachlorophenol, pentanochlor, pentoxazone, petroleum oils, phenmedipham, picloram, piperophos, pretilachlor, primisulfuron-methyl, prodiamine, prometon, prometryn, propachlor, propanil, propaquizafop, propazine, propham, propisochlor, propyzamide, prosulfocarb, prosulfuron, pyraflufen-ethyl, pyrazolynate, pyrazosulfuron-ethyl, pyrazoxyfen, pyributicarb, pyridate, pyriminobac-methyl, pyrithiobac-sodium, quinclorac, quinmerac, quinoclamine, quizalofop, quizalofop-P, rimsulfuron, sethoxydim, siduron, simazine, simetryn, sodium chlorate, STS system (sulfonylurea), sulcotrione, sulfentrazone, sulfometuron-methyl, sulfosulfuron, sulfuric acid, tar oils, 2,3,6-TBA, TCA-sodium, tebutam, tebuthiuron, terbacil, terbumeton, terbuthylazine, terbutryn, thenylchlor, thiazopyr, thifensulfuron-methyl, thiobencarb, tiocarbazil, tralkoxydim, tri-allate, triasulfuron, triaziflam, tribenuron-methyl, triclopyr, trietazine, trifluralin, triflusulfuron-methyl, vernolate, and combinations thereof.

In some embodiments, an agrochemical composition contains one or more fungicides. Suitable fungicides include, but are not limited to, carbamate fungicides such as 3,3'-ethylenebis(tetrahydro-4,6-dimethyl-2H-1,3,5-thiadiazine-2-thione), zinc or manganese ethylenebis(dithiocarbamate), bis(dimethyldithiocarbamoyl)disulfide, zinc propylene-bis-(dithiocarbamate), bis(dimethyldithiocarbamoyl)ethylenediamine, nickel dimethyl-dithiocarbamate, methyl 1-(butylcarbamoyl)-2-benzimidazolecarbamate, 1,2-bis(3-methoxycarbonyl-2-thioureido)benzene, 1-isopropylcarbamoyl-3-(3,5-dichlorophenyl)-hydantoin, potassium N-hydroxymethyl-N-methyldithiocarbamate, and 5-methyl-10-butoxycarbonylamino-10,11-dehydrodibenzo (b,f)azepine; pyridine fungicides such as zinc bis(1-hydroxy-2(1H)pyridinethionate) and 2-pyridinethiol-1-oxide sodium salt; phosphorus fungicides such as O,O-diisopropyl S-benzylphosphorothioate and O-ethyl S,S-diphenyldithiophosphate; phthalimide fungicides such as N-(2,6-diethylphenyl)phthalimide and N-(2,6-diethylphenyl)-4-methylphthalimide; dicarboxyimide fungicides such as N-trichloromethylthio-4-cyclohexene-1,2-dicarboxyimide and N-tetrachloroethylthio-4-cyclohexene-1,2-dicarboxyimide; oxathine fungicides such as 5,6-dihydro-2-methyl-1, 4-oxathine-3-carboxanilido-4,4-dioxide and 5,6-dihydro-2-methyl-1,4-oxathine-3-carboxanilide; naphthoquinone fungicides such as 2,3-dichloro-1,4-naphthoquinone, 2-oxy-3-chloro-1,4-naphthoquinone copper sulfate; pentachloronitrobenzene; 1,4-dichloro-2,5-dimethoxybenzene; 5-methyl-s-triazol (3,4-b)benzthiazole; 2-(thiocyanomethylthio) benzothiazole; 3-hydroxy-5-methylisooxazole; N-2,3-dichlorophenyltetrachlorophthalamic acid; 5-ethoxy-3-trichloromethyl-1-2,4-thiadiazole; 2,4-dichloro-6-(O-chloroanilino)-1,3,5-triazine; 2,3-dicyano-1,4-dithio-anthraquinone; copper 8-quinolinate, polyoxine; validamycin; cycloheximide; iron methanearsonate; diisopropyl-1,3-dithiolane-2-iridene malonate; 3-allyloxy-1,2-benzoisothiazol-1,1-dioxide; kasugamycin; Blasticidin S; 4,5,6,7-tetra-chlorophthalide; 3-(3,5-dichlorophenyl)-5-ethenyl-5-methyloxazolizine-2,4-dione; N-(3,5-dichlorophenyl)-1,2-dimethylcyclopropane-1,2-dicarboxyimide; S-n-butyl-5'-para-t-butylbenzyl-N-3-pyridyldithiocarbonylimidate; 4-chlorophenoxy-3,3-dimethyl-1-(1H,1,3,4-triazol-1-yl)-2-butanone; methyl-D,L-N-(2,6-dimethylphenyl)-N-(2'-methoxyacetyl)alaninate; N-propyl-N-[2-(2,4,6-trichlorophenoxy)ethyl]phosphor-1-carboxamide; N-(3,5-dichlorophenyl)-succinimide; tetrachloroisophthalonitrile; 2-dimethyl amino-4-methyl-5-n-butyl-6-hydroxypyrimidine; 2,6-dichloro-4-nitroaniline; 3-methyl-4-chlorobenzthiazol-2-one; 1,2,5,6-tetrahydro-4H-pyrrolo[3,2,1-I,j]phosphor-2-one; 3'-isopropoxy-2-methyl-benzanilide; 1-[2-(2,4-dichlorophenyl)-4-ethyl-1,3-dioxorane-2-ylmethyl]-1H,1,2,4-triazol; 1,2-benzisothiazoline-3-one; basic copper chloride; basic copper sulfate; N'-dichlorofluoromethylthio-N,N-dimethyl-N-phenylsulfamide; ethyl-N-(3-dimethyl amino-propyl)thiocarbamate hydrochloride; piomycin; S,S-6-methylquinoxaline-2,3-diyldithio-carbonate; complex of zinc and manneb; di-zinc bis(dimethyl dithiocarbamate) ethylenebis (dithiocarbamate) and glyphosate; chlorothalonil-based fungicides, strobilurin-based fungicides such as azoxystrobin, pyraclostrobin, and trifloxystrobin; and triazole-based fungicide such as myclobutanil, propiconazole, tebuconazol, tetraconazole, and combinations thereof.

In some embodiments, an agrochemical composition contains one or more insecticides. Suitable insecticides include, but are not limited to, phosphoric insecticides such as O,O-diethyl O-(2-isopropyl-4-methyl-6-pyrimidinyl)phosphorothioate, O,O-dimethyl S-2-[(ethylthio)ethyl]phosphorodithioate, O,O-dimethyl O-(3-methyl-4-nitrophenyl)-thiophosphate, O,O-dimethyl S—(N-methylcarbamoylmethyl)-phosphorodithioate, O,O-dimethyl S—(N-methyl-N-formylcarbamoylmethyl) phosphorodithioate, O,O-dimethyl S-2-[(ethylthio)ethyl] phosphorodithioate, O,O-diethyl S-2-[(ethylthio)ethyl] phosphorodithioate, O,O-dimethyl-1-hydroxy-2,2,2-trichloroethylphophonate, O,O-diethyl-O-(5-phenyl-3-isooxazolyl)phosphorothioate, O,O-dimethyl O-(2,5-dichloro-4-bromophenyl) phosphorothioate, O,O-dimethyl O-(3-methyl-4-methylmercaptophenyl)-thiophosphate, O-ethyl O-p-cyanophenyl phenyl-phosphorothioate, O,O-dimethyl-S-(1,2-dicarboethoxyethyl)phosphorodithioate, 2-chloro-(2,4,5-trichlorophenyl)vinyldimethyl phosphate, 2-chloro-1-(2,4-dichlorophenyl)-vinyldimethyl phosphate, O,O-dimethyl O-p-cyanophenyl phosphorothioate, 2,2-dichlorovinyl dimethyl phosphate, O,O-diethyl O-2,4-dichlorophenyl phosphorothioate, ethyl mercaptophenylacetate O,O-dimethyl phosphoro-dithioate, S-[(6-chloro-2-oxo-3-benzooxazolinyl)methyl] O,O-diethyl phosphorodithioate, 2-chloro-1-(2,4-dichlorophenyl)vinyl diethylphosphate, O,O-diethyl O-(3-oxo-2-phenyl-2H-pyridazine-6-yl) phosphorothioate, O,O-dimethyl S-(1-methyl-2-ethylsulfinyl)-ethyl phosphorothiolate, O,O-dimethyl S-phthalimidomethyl phosphorodithioate, O,O-diethyl S—(N-ethoxycarbonyl-N-methylcarbamoylmethyl)phosphorodithioate, O,O-dimethyl S-[2-methoxy-1,3,4-thiadiazol-5-(4H)-I-(4)-methyl] dithiophosphate, 2-methoxy-4H-1,3,2-benzooxaphosphorine 2-sulfide, O,O-diethyl O-(3,5,6-trichloro-2-pyridyl)phosphorothiate, O-ethyl O-2,4-dichlorophenyl thionobenzene phosphonate, S-[4,6-diamino-s-triazine-2-yl-methyl] O,O-dimethyl phosphorodithioate, O-ethyl O-p-nitrophenyl phenyl phosphorothioate, O,S-dimethyl N-acetyl phosphoroamidothioate, 2-diethylamino-6-methylpyrimidine-4-yl-diethylphosphorothionate, 2-diethylamino-6-methylpyrimidine-4-yl-dimethylphosphorothionate, O,O-diethyl O—N-(methylsulfinyl) phenyl phosphorothioate, O-ethyl S-propyl O-2,4-dichlorophenyl phosphorodithioate and cis-3-(dimethoxyphosphinoxy)N-methyl-cis-crotone amide; carbamate insecticides such as 1-naphthyl N-methylcarbamate, S-methyl N-[methylcarbamoyloxy]thioacetoimidate, m-tolyl methylcarbamate, 3,4-xylyl methylcarbamate, 3,5-xylyl methylcarbamate, 2-sec-butyl phenyl N-methylcarbamate, 2,3-dihydro-2,2-dimethyl-7-benzofuranylmethyl-carbamate, 2-isopropoxyphenyl N-methylcarbamate, 1,3-bis(carbamoylthio)-2-(N,N-dimethylamino) propane hydrochloride and 2-diethylamino-6-methylpyrimidine-4-yl-dimethylcarbamate; and other insecticides such as N,N-dimethyl N'-(2-methyl-4-chlorophenyl)formamidine hydrochloride, nicotine sulfate, milbemycin, 6-methyl-2,3-quinoxalinedithiocyclic S,S-dithiocarbonate, 2,4-dinitro-6-sec-butylphenyl dimethyl-acrylate, 1,1-bis(p-chlorophenyl) 2,2,2-trichloroethanol, 2-(p-tert-butylphenoxy)isopropyl-2'-chloroethylsulfite, azoxybenzene, di-(p-chlorophenyl)-cyclopropyl carbinol, di[tri(2,2-dimethyl-2-phenylethyl)tin]oxide, 1-(4-chlorophenyl)-3-(2,6-difluorobenzoyl) urea, S-tricyclohexyltin O,O-diisopropyl-phosphorodithioate, and combinations thereof.

In some embodiments, an agrochemical composition contains one or more fertilizers. A variety of fertilizers are suitable for inclusion in the compositions. The fertilizer can be a single nutrient fertilizer (N, P, or K), binary fertilizer (e.g., NP, NK, or PK), a NPK fertilizer, or a multinutrient fertilizer (e.g., may provide one or more of calcium, magnesium, sulfur, copper, iron, manganese, molybdenum, zinc, boron, silicon, cobalt, or vanadium). The fertilizer can be of natural origin or synthetic origin. The fertilizer can be liquid or solid, and may provide slow or controlled release.

In some embodiments, the MdsRNAs comprise less than 50% by weight of a composition. In some embodiments, the amount of MdsRNA in an agriculture composition is less than 5% by weight of the composition. In some embodiments, the MdsRNA is present in the composition in an amount less than about 1% by weight, less than about 0.9% by weight, less than about 0.8% by weight, less than about 0.7% by weight, less than about 0.6% by weight, less than about 0.5% by weight, less than about 0.4% by weight, less than about 0.3% by weight, less than about 0.2% by weight, less than about 0.1% by weight, less than about 0.05% by weight, less than about 0.01% by weight, or less than about 0.001% by weight of the composition.

In some embodiments, the agrochemical composition is formulated as a liquid. Liquid formulations can be prepared by mixing the MdsRNA and other agents in a liquid until dissolution of all the components is achieved in the weight percentages described below. The liquid can be an aqueous, ionic, or organic liquid. Suitable liquids include, but are not limited to, water, alcohols (e.g. methanol and ethanol), ketones (e.g. acetone, methyl ethyl ketone and cyclohexanone), aromatic hydrocarbons (e.g. benzene, toluene, xylene, ethylbenzene and methylnaphthalene), aliphatic hydrocarbons (e.g. hexane and kerosene), esters (e.g. ethyl acetate and butyl acetate), nitriles (e.g. acetonitrile and isobutyronitrile), ethers (e.g. dioxane and diisopropyl ether), acid amides (e.g. dimethylformamide and dimethylacetamide), and halogenated hydrocarbons (e.g. dichloroethane, trichloroethylene and carbon tetrachloride).

In some embodiments, the liquid formulation is an aqueous formulation. In some embodiments, an aqueous formulation contains only water, the MdsRNA and other agents. In some embodiments, additional compounds, solvents, or adjuvants are provided with the aqueous formulation.

In some embodiments, the agrochemical composition is formulated as a powder or dust. The powder or dust can be granulated to be suitable for applying the powder or dust directly to a crop (i.e., by dusting the crop), or it can be granulated for eventual dissolution in a solvent such as water. In some embodiments, the composition is a lyophilisate. Typically, the MdsRNA and the other agents are lyophilized together. In some embodiments, one or more MdsRNAs and the other agents can be lyophilized separately.

A variety of suitable solid and gaseous carriers can be utilized in the compositions. Suitable solid carriers include, but are not limited to, fine powders or granules of clays (e.g. kaolin clay, diatomaceous earth, synthetic hydrated silicon dioxide, attapulgite clay, bentonite and acid clay), talcs, bulking agents, inorganic minerals (e.g., sericite, powdered quartz, powdered sulfur, activated carbon, calcium carbonate and hydrated silica), and salts for chemical fertilizers (e.g. ammonium sulfate, ammonium phosphate, ammonium nitrate, urea and ammonium chloride). Suitable gaseous carriers include, for example, butane gas, carbon dioxide, and fluorocarbon gas.

In some embodiments, an agrochemical composition includes a dispersant. Examples of dispersants include, but are not limited to, methyl cellulose, polyvinyl alcohol, sodium lignin sulfonates, polymeric alkyl naphthalene sulfonates, sodium naphthalene sulfonate, polymethylene bisnaphthalene sulfonate, neutralized polyoxyethylated derivatives, and ring-substituted alkyl phenol phosphates. Stabilizers may also be used to produce stable emulsions. Exemplary stabilizers include, but are not limited to magnesium, aluminum silicate, and xanthan gum.

In some embodiments, an agrochemical composition is formulated as a spray in the form of an aerosol. When formulated as an aerosol spray, the composition is generally charged in a container under pressure together with a propellant. Examples of suitable propellants include fluorotrichloromethane and dichlorodifluoromethane.

In some embodiments, an agrochemical composition includes a seed. In some embodiments, an agrochemical composition comprises an antifungal MdsRNA and a seed. In some embodiments, an agrochemical composition comprises a MdsRNA, a seed, and further comprises a fungicide.

In some embodiments, the amount of the MdsRNA in a fungicidal composition (agrochemical composition containing a fungicide) is less than about 5% by weight, less than about 1% by weight, less than about 0.9% by weight, less than about 0.8% by weight, less than about 0.7% by weight, less than about 0.6% by weight, less than about 0.5% by weight, less than about 0.4% by weight, less than about 0.3% by weight, less than about 0.2% by weight, less than about 0.1% by weight, less than about 0.05% by weight, less than about 0.01% by weight, or less than about 0.001% by weight of the fungicidal composition. The weight of the fungicidal composition does not include the weight of the seed.

In some embodiments, the fungicidal composition is present inside the seed coat, or internal to the seed. In some embodiments, the fungicidal composition is formed over the seed such that it covers the exterior of the seed, either fully or partially. Methods for coating a seed include those known in the art.

Methods for Controlling Agricultural Pests

In some embodiments, MdsRNAs or compositions containing MdsRNAs are used to control agricultural pests or treat agricultural pest infestation. The MdsRNAs can be administered to the pest, to an area occupied by the pest, or to a food source of the pest.

In some embodiments, methods are provided for treating for or controlling pests. In some embodiments, the pest is an animal, fungus, or weed. The methods comprise applying a composition comprising one or more described MdsRNAs to an area to be treated. In some embodiments, the MdsRNA is present in the composition in an amount of less than 5% by weight. In some embodiments, the composition is applied directly to a surface. In some embodiments, the surface is a plant surface upon which the targeted animal or fungal pest feeds.

In some embodiments, the gene expression level and/or mRNA level of a target gene in a target host is reduced by at least about 5%, 10%, 20%, 30%, 40%, 50%, 60%, 70%, 80%, or 90%, following application of MdsRNAs or MdsRNA-containing composition. In some embodiments, mortality of the agricultural pest in increased at least 5%, 10%, 20%, 30%, 40%, 50%, 60%, 70%, 80%, or 90% following application of MdsRNAs or MdsRNA-containing composition.

As used herein, controlling a pest means to reduce crop damage or decreased yield caused by the pest, or to increase morbidity, inhibit growth or appetite or feeding of, or slow reproduction of the pest compared with the damage, decreased yield morbidity, growth, appetite, feeding, or reproduction as measured in the absence of treatment with MdsRNAs.

Crop Application

In some embodiments, we describe methods of reducing expression of a target gene in a target plant other than a weed, the methods comprising applying a composition containing one or more of the described MdsRNAs to the plant. In some embodiments, the plant is a crop plant. A crop plant is a plant a plant that can be grown and harvested for profit or subsistence. A crop plant can be, but is not limited to, a food plant, horticultural plant, florticulture plant, or inductrial plant. In some embodiments, the plant is a cultivated plant. The plant can be in a laboratory, greenhouse, nursery, field, orchard or other agricultural setting, garden, or another natural or urban setting. In some embodiments, a target plant is a plant considered desirable in a particular situation or location.

Insect Infestation

In some embodiments the animal is an insect. In some embodiments, the insect is a Coleopteran. A Coleopteran can be, but are not limited to, bark beetle, elm leaf beetle, Asian longhorn beetle, death watch beetle, mountain pine beetle, coconut hispine beetle or the Colorado potato beetle. In some embodiments, the insect is a Lepidopteran. A Lepidopteran can be, but is not limited to, army worm, corn ear worm, cabbage butterfly, orcotton boll worm. In some embodiments, the insect is a Hymenopteran. A Hymenopteran can be, but is not limited to, fire ant, argentine ant, carpenter ant, leafcutter ant, army ant, wheat stem sawfly, larch sawfly, spruce sawfly, or bed bug. In some embodiments, the insect is a Dipteran. A Dipteran can be, but is limited to, fly, mosquito, gnat, or leafminer. In some embodiments, the insect is a Hemipteran. A Hemipteran can be, but is not limited to, aphid, hopper, bug, whiteflies, mealybug, or flea. In some embodiments, the insect is a Western corn root worm.

In some embodiments, the insect is an insect having resistance to one or more conventional known insecticides. In some embodiments, the insect, such as a Red imported fire ant has the potential to have a negative impact on biodiversity (Wojcik et al. 2001 and/or resistance to insecticides (Zhang et al. 2016). In some embodiments, the insect, such as a mosquito, has the potential to impact human health as a vector for disease, such as, but not limited to: Malaria, Dengue, Zika and Chikungunya (Hemingway et al. 2004). In some embodiments, the insect, such as Asian citrus psyllid, is a vector of the citrus greening disease (Tiwari et al. 2011).

Coleopteran, Lepidopteran, Hymenopteran, Dipteran, and Hemipteran insect pests are known to be susceptible to RNAi introduced either by direct injection or by feeding on plant matter treated with siRNA precursors. Field application of naked RNAs is generally impractical due to the sensitivity of RNA to environmental specific and non-specific degradation (Baum 2016). Furthermore, RNA is highly susceptible to degradation during the course of feeding and in transit through the insect gut. For example, in general, the Lepidoptera seem to degrade RNA much more aggressively than the Coleoptera, which may account for their relatively poor susceptibility to RNAi mediated control methods. The stability of the described MdsRNAs serves to protect the MdsRNA from host nucleases before delivery to the RNAi pathway, and limits non-specific environmental degradation. The described MdsRNAs are nevertheless sufficiently biodegradable to be considered environmentally safe.

A composition comprising one or more MdsRNAs can be applied to a plant prior to infection to prevent an insect infection. The composition may also be applied after the appearance of signs of infection to treat an insect infection. The composition can be applied by a variety of methods depending on the plant part to be treated. By way of example, the composition can be applied to a plant seed prior to planting to prevent insect infection of the seed. The composition can be applied to the soil at the time of planting or just before planting to prevent insect infestation of the newly planted seed (i.e., as a pre-emergent). In some embodiments, the composition can be applied to a plant after its germination or to the foliage of the plant after emergence to either treat or prevent insect infestation (i.e., as a post-emergent). In an exemplary embodiment, the application occurs during the stages of germination, seedling growth, vegetative growth, and reproductive growth. In some embodiments, application occurs during vegetative and reproductive growth stages.

Applying the composition to a pre-emergent seed may involve various seed coating techniques such as film coating, pelleting, encapsulation, drum coating, and fluidized bed coating. Applying to a post-emergent plant may involve spraying or crop dusting techniques.

An effective amount of the composition can be applied to a plant or seed by several methods generally known in the art. As will be appreciated by a skilled artisan, the amount of composition comprising an "an effective amount" can and will vary depending upon the plant and its stage of production, the fungal target, and environmental conditions. Generally speaking, for a typical application, the plant or its progeny is treated with an amount of the composition sufficient to provide a concentration of active ingredients from about 0.01 mg/kg to about 10% by weight. It is envisioned that the method may involve more than one application of the composition to the plant or its progeny. For example, the number of applications may range from about 1 to about 5 or more. The applications, as detailed herein, can be applied at the same or different stages of the plant's life cycle.

Fungal Infection

In some embodiments, the MdsRNAs are used to treat or prevent fungal infection. In some embodiments, the fungus can be, but is not limited to, a *Venturia, Podosphaera, Erysiphe, Monolinia, Mycosphaerella, Uncinula; Basidiomycete, Hemileia, Rhizoctonia, Puccinia, Fungi imperfecti, Botrytis, Helminthosporium, Rhynchosporium, Fusarium, Septoria, Cercospora, Alternaria, Pyricularia, Pseudocercosporella, Oomycete fungi, Phytophthora, Peronospora, Bremia, Pythium, Plasmopara, Phakopsora Pachyrhizi, P. meibomiae, Scleropthora macrospora, Sclerophthora rayissiae, Sclerospora graminicola, Peronosclerospora sorghi, Peronosclerospora philippinensis, Peronosclerospora sacchari Peronosclerospora maydis, Physopella zeae, Cercospora zeae-maydis, Colletotrichum graminicola, Hypocreale, Gibberella zeae, Exserohilum turcicum, Kabatiellu zeae, Bipolaris maydis, Gibberella avenacea, Fusarium culmorum, Fusarium oxysporum, Fusarium sporotrichioides*, or *Fusarium graminearum*. In some embodiments, treatment of *Fusarium graminearum* can reduce the production of mycotoxins, the risk of emergence of resistance to fungicides based on demethylation inhibitors (DMI), orcarcinogenicity concerns about conventional DMI like Tebuconazole.

In some embodiments, the described agrochemical compositions can be applied to a plant prior to infection to prevent a fungal infection. In some embodiments, the described agrochemical compositions can be applied to a plant after the appearance of signs of infection to treat a fungal infection. The composition can be applied by a variety of methods depending on the plant part to be treated. By way of example, the composition can be applied to a plant seed prior to planting to prevent fungal infection of the seed. The composition can be applied to the soil at the time of planting or just before planting to prevent microbial infestation of the newly planted seed (i.e., as a pre-emergent). In some embodiments, the composition can be applied to a plant after its germination or to the foliage of the plant after emergence to either treat or prevent microbial infestation (i.e., as a post emergent). In an exemplary embodiment, the application occurs during the stages of germination, seedling growth, vegetative growth, and reproductive growth. More typically, applications occur during vegetative and reproductive growth stages.

Applying the composition to a pre-emergent seed may involve various seed coating techniques such as film coating, pelleting, encapsulation, drum coating, and fluidized bed coating. Applying to a post-emergent plant may involve spraying or crop dusting techniques.

An effective amount of the composition can be applied to a plant or seed by several methods generally known in the art. As will be appreciated by a skilled artisan, the amount of composition comprising an "an effective amount" can and will vary depending upon the plant and its stage of production, the fungal target, and environmental conditions. Generally speaking, for a typical application, the plant or its progeny is treated with an amount of the composition sufficient to provide a concentration of active ingredients from about 0.01 mg/kg to about 10% by weight. It is envisioned that the method may involve more than one application of the composition to the plant or its progeny. For example, the number of applications may range from about 1 to about 5 or more. The applications, as detailed herein, can be made at the same or different stages of the plant's life cycle.

Definitions

As used herein, a "modified nucleotide" is a nucleotide other than a ribonucleotide (2'-hydroxyl nucleotide). In some embodiments, at least 2%, at least 5%, at least 10%, at least 20%, at least 30%, at least 40%, at least 50%, at least 60%, at least 60%, at least 70%, at least 80%, or at least 90% of the nucleotides in a MdsRNA are post-synthetically modified. Modified nucleotides include, but are not limited to, nucleotides having a ribose 2'-OH substitution.

A transcribed RNA is an RNA molecule which has been transcribed from a DNA sequence or vector by a cell free transcription system, an archaea, bacterial, or eukaryotic cell, or an archaea, bacterial, or eukaryotic cell extract.

An unmodified dsRNA is an RNA molecule that has not been chemically modified.

By inhibiting, down-regulating, or knocking down gene expression, it is meant that the expression of the gene, as measured by the level of RNA transcribed from the gene or the level of polypeptide, protein or protein subunit translated from the RNA, is reduced below that observed in the absence of the MdsRNA. In some embodiments, inhibition, down-regulation, or knockdown of gene expression, with a MdsRNA is below the level observed in the presence of a control inactive nucleic acid, or a nucleic acid with scrambled sequence or with inactivating mismatches.

As used herein, the term "sequence" or "nucleotide sequence" refers to a succession or order of nucleobases, nucleotides, and/or nucleosides, described with a succession of letters using the standard nucleotide nomenclature and the key for modified nucleotides described herein.

The term "acyl," as used herein alone or as part of another group, denotes the moiety formed by removal of the hydroxyl group from the group COOH of an organic carboxylic acid, e.g., RC(O)—, wherein R is $R^1$, $R^1O$—, $R^1R^2N$—, or $R^1S$—, $R^1$ is hydrocarbyl, heterosubstituted hydrocarbyl, or heterocyclo, and $R^2$ is hydrogen, hydrocarbyl, or substituted hydrocarbyl.

The term "acyloxy," as used herein alone or as part of another group, denotes an acyl group as described above bonded through an oxygen linkage (O), e.g., RC(O)O— wherein R is as defined in connection with the term "acyl."

The term "allyl," as used herein not only refers to compound containing the simple allyl group ($CH_2$=CH—$CH_2$—), but also to compounds that contain substituted allyl groups or allyl groups forming part of a ring system.

The term "alkyl" or "alkyl group" as used herein describes a univalent group derived from alkanes by removal of a hydrogen atom from any carbon atom —$C_nH_{2n+1}$. An alkyl group can be straight or branched chain or cyclic and include methyl, ethyl, propyl, isopropyl, butyl, hexyl and the like. As used herein, a lower alkyl group contains from one to eight carbon atoms in the principal chain and up to 20 carbon atoms.

The term "alkenyl" as used herein are acyclic branched or unbranched hydrocarbons having one carbon-carbon double bond and the general formula —$C_nH_{2n-1}$. One or more of the hydrogen atoms can be substituted. An alkyl group can be straight or branched chain and include ethenyl, propenyl, isopropenyl, butenyl, isobutenyl, hexenyl, and the like. As used herein, an alkenyl contains from two to eight carbon atoms in the principal chain and up to 20 carbon atoms.

The term "alkoxide" or "alkoxy" as used herein is the conjugate base of an alcohol. The alcohol can be straight chain, branched, cyclic, and includes aryloxy compounds.

The term "alkynyl" as used herein are acyclic branched or unbranched hydrocarbons having a carbon-carbon triple bond and the general formula —$C_nH_{2n-3}$. They can be straight or branched chain and include ethynyl, propynyl, butynyl, isobutynyl, hexynyl, and the like. As used herein a lower alkynyl containing from two to eight carbon atoms in the principal chain and up to 20 carbon atoms.

The term "aromatic" as used herein alone or as part of another group denotes optionally substituted homo- or heterocyclic conjugated planar ring or ring system comprising delocalized electrons. Aromatic groups can be monocyclic (e.g., furan or benzene), bicyclic, or tricyclic groups containing from 5 to 14 atoms in the ring portion. The term "aromatic" encompasses "aryl" groups defined below.

The terms "aryl" or "Ar" as used herein alone or as part of another group denote optionally substituted homocyclic aromatic groups. Aryl groups can be monocyclic or bicyclic groups containing from 6 to 10 carbons in the ring portion, such as phenyl, biphenyl, naphthyl, substituted phenyl, substituted biphenyl, or substituted naphthyl.

The terms "carbocyclo" or "carbocyclic" as used herein alone or as part of another group denote optionally substituted, aromatic or non-aromatic, homocyclic ring or ring system in which all of the atoms in the ring are carbon. In some embodiments, the carbocyclo" or "carbocyclic" group contains 5 or 6 carbon atoms in each ring. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phosphor, nitro, and thio.

The terms "halogen" or "halo" as used herein alone or as part of another group refer to chlorine, bromine, fluorine, and iodine.

The term "heteroatom" refers to atoms other than carbon and hydrogen.

The term "heteroaromatic" as used herein alone or as part of another group denotes optionally substituted aromatic groups having at least one heteroatom in at least one ring. In some embodiments, heteroaromatic group contains 5 or 6 atoms in each ring. In some embodiments, a heteroaromatic group contains 1 or 2 oxygen atoms and/or 1 to 4 nitrogen atoms in the ring, and is bonded to the remainder of the molecule through a carbon. Exemplary groups include furyl, benzofuryl, oxazolyl, isoxazolyl, oxadiazolyl, benzoxazolyl, benzoxadiazolyl, pyrrolyl, pyrazolyl, imidazolyl, triazolyl, tetrazolyl, pyridyl, pyrimidyl, pyrazinyl, pyridazinyl, indolyl, isoindolyl, indolizinyl, benzimidazolyl, indazolyl, benzotriazolyl, tetrazolopyridazinyl, carbazolyl, purinyl, quinolinyl, isoquinolinyl, imidazopyridyl, and the like. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phosphor, nitro, and thio.

The terms "heterocyclo" or "heterocyclic" as used herein alone or as part of another group denote optionally substituted, fully saturated or unsaturated, monocyclic or bicyclic, aromatic or non-aromatic groups having at least one heteroatom in at least one ring. In some embodiments, the heterocyclo or heterocyclic group contains 5 or 6 atoms in each ring. In some embodiments, a heterocyclo group has 1 or 2 oxygen atoms and/or 1 to 4 nitrogen atoms in the ring, and is bonded to the remainder of the molecule through a carbon or heteroatom. Exemplary heterocyclo groups include heteroaromatics as described above. Exemplary substituents include one or more of the following groups: hydrocarbyl, substituted hydrocarbyl, alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phosphor, nitro, and thio.

The terms "hydrocarbon" and "hydrocarbyl" as used herein describe organic compounds or radicals consisting exclusively of the elements carbon and hydrogen. These moieties include alkyl, alkenyl, alkynyl, and aryl moieties. These moieties also include alkyl, alkenyl, alkynyl, and aryl moieties substituted with other aliphatic or cyclic hydrocarbon groups, such as alkaryl, alkenaryl and alkynaryl. Unless otherwise indicated, these moieties comprise 1 to 20 carbon atoms.

The "substituted hydrocarbyl" moieties described herein are hydrocarbyl moieties which are substituted with at least one atom other than carbon, including moieties in which a carbon chain atom is substituted with a heteroatom such as nitrogen, oxygen, silicon, phosphorous, boron, or a halogen atom, and moieties in which the carbon chain comprises additional substituents. These substituents include alkyl, alkoxy, acyl, acyloxy, alkenyl, alkenoxy, aryl, aryloxy, amino, amido, acetal, carbamyl, carbocyclo, cyano, ester, ether, halogen, heterocyclo, hydroxyl, keto, ketal, phospho, nitro, and thio.

EXAMPLES

Example 1. Preparation of 2'-OH Substituted Adenosine 3',5'-Cyclic Monophosphate (cAMP)

A simple surrogate substrate, adenosine 3',5'-cyclic monophosphate (cAMP), was used to identify and quantify the products obtained from reaction with NMIA using HPLC/MS. cAMP was reacted with NMIA under the same reaction conditions used for dsRNA, as described in Example 3. About 75% conversion was observed. A single product peak of the expected parent ion (462 Da) was observed by HPLC/MS.

The product was then subjected to a mild basic hydrolysis. Under these conditions this product peak was no longer observed and another peak identified as the corresponding nucleoside was observed. The amount of the nucleoside formed was measured as approximately the same amount as the nucleotides present before hydrolysis, showing that NMIA reacted exclusively with the 2'-OH of the ribose.

Example 2. Preparation of UdsRNAs

UdsRNAs of known sequences were prepared for testing the described methods in subsequent reactions for chemical modification. CPB_β-A_ds (SEQ ID NO. 3), comprising a bacteriophage SP6 promoter on the 5' end, sense and antisense strands corresponding to a 297 bp fragment of beta actin (SEQ ID NO. 13) from Colorado potato beetle (*Leptinotarsa decemlineata* strain Freeville actin mRNA, GenBank sequence ID: gb|KJ577616.1, nucleotides 1-297), and an NcoI restriction site on the 3' end was cloned by PCR amplification of the region of interest and subsequently ligated into a pMA plasmid from GeneArt™/Thermo Fisher Scientific (Waltham, Mass.) containing a colE1 origin, a multi-cloning site, and ampicillin resistance gene (SEQ ID NO. 1), oriented such that bacteriophage SP6 polymerase transcribed the cloned fragment inserted into the plasmid. One Shot BL21(DE3) Chemically Competent *E. coli* (Thermo Fisher Scientific, Waltham, Mass.) cells were transformed using the plasmid. BL21(DE3) containing the plasmid was grown in LB medium containing ampicillin at 37° C., to OD(600 nm) equal to 0.8. Plasmid was isolated using QIAprep® Spin Miniprep Kit (Qiagen, Hilden, Germany) following manufacturer's instructions. NcoI (New England Biolabs, Ipswich, Mass.) was used to cut the isolated plasmid at the restriction site introduced into the construct. After digestion, the template was purified by electrophoresis on 1.5% agarose gels and isolated using PureLink™ Quick Gel Extraction Kit (Life Technologies, Carlsbad, Calif.) following manufacturer's instructions. Transcriptions were done using MAXIscript® SP6 Kit (Thermo Fisher Scientific, Waltham, Mass.) following manufacturer's instructions. Briefly, following RNA transcription the DNA template was removed by incubation with DNAse and then purified by extraction with phenol:chloroform and purification by Sephadex G100 chromatography in 10 mM Tris-HCl, pH 7, 0.1% SDS. NaCl was added to reach 0.3M. Single stranded RNA was digested by incubation at 37° C. for 30 minutes with 0.1 ng of RNase A (ThermoFisher Scientific, Waltham, Mass.) per μg of RNA. RNase A was removed by incubation at 37° C. for 1 hour with 200 ng of Proteinase K (ThermoFisher Scientific, Waltham, Mass.), per ng RNAse A). The RNA product, named RNA_CPB_β-A_ds_ds, was recovered by precipitation with 2.5 volumes of ethanol. The pellet obtained by centrifugation was allowed to dry in air, dissolved in water, and stored at −20° C. until use. All other DNA constructs described are cloned and transcribed in similar manner, and resulting RNA constructs are isolated in similar manner.

DNA constructs CPB_β-A_1-14_mut (SEQ ID NO. 25), CPB_β-A_1-22_mut (SEQ ID NO. 26), CPB_β-A_1-33_mut (SEQ ID NO. 27), RIFA_A_1-5_mut (SEQ ID NO. 28), RIFA_A_1-7_del (SEQ ID NO. 29), RIFA_A_1-7_mut (SEQ ID NO. 30), RIFA_A_1-7_ins (SEQ ID NO. 31), RIFA_A_1-10 (SEQ ID NO. 32), RIFA_A_2-7_mut (SEQ ID NO. 33), RIFA_A_2-7_ins (SEQ ID NO. 34), DBM_AChE2_dsDNA (SEQ ID NO. 35), and RIFA_A_ds_ds (SEQ ID NO. 36) were prepared separately using RNA transcripts in a similar manner as that described for the RNA transcript prepared using the DNA construct CPB_β-A_ds_ds (SEQ ID NO. 3). The RNA products obtained were named according to the DNA constructs from which they were derived, namely RNA_CPB_β-A_1-14_mut, RNA_CPB_β-A_1-22_mut, RNA_CPB_β-A_1-33_mut, RNA_RIFA_A_1-5_mut, RNA_RIFA_A_1-7_del, RNA_RIFA_A_1-7_mut, RNA_RIFA_A_1-7_ins, RNA_RIFA_A_1-10, RNA_RIFA_A_2-7_mut, RNA_RIFA_A_2-7_ins, RNA_DBM_AChE2_dsDNA, and RNA_RIFA_A_ds_ds.

DNA constructs CPB_β-A_1-5_mut (SEQ ID NO. 4), CPB_β-A_1-7_del (SEQ ID NO. 5), CPB_β-A_1-7_mut (SEQ ID NO. 6), CPB_β-A_1-7_ins (SEQ ID NO. 7), CPB_β-A_1-10_mut (SEQ ID NO. 8), CPB_β-A_2-7_mut (SEQ ID NO. 11), and CPB_β-A_2-7_ins (SEQ ID NO. 12)

can be used to separately prepare RNA transcripts in a similar manner as that described for the RNA transcript prepared using the DNA construct CPB_β-A_ds_ds (SEQ ID NO. 3). The RNA products obtained are named according to the DNA constructs from which they are derived, namely RNA_CPB_β-A_1-7_del, RNA_CPB_β-A_1-7_mut, RNA_CPB_β-A_1-7_ins, RNA_CPB_β-A_1-10_mut, RNA_CPB_β-A_2-7_mut, RNA_CPB_β-A_2-7_ins. Similar UdsRNAs can be made to other genes in other hosts.

Example 3. Preparation of 2'-N-methylanthranoate MdsRNAs

The described methods, which enable efficient reaction between NMIA and dsRNA, were tested by reacting UdsRNA prepared in Example 2 with NMIA as described here to prepare MdsRNAs.

12.5 μL of 3.2 g/L aqueous solution of RIFA-A_ds_ds (SEQ ID NO. 16) was added to 17.5 μL of dimethyl sulfoxide (DMSO, Sigma Aldrich, St. Louis, Mo.), warmed to 67° C., and kept at this temperature. After 15 min at 67° C., 40 μL of 97 g/L DMSO solution of NMIA (Thermo Fisher Scientific, Waltham, Mass.) pre-heated to 67° C. was added and mixed. Immediately afterwards, 10 μL of 40.3 g/L DMSO solution of 4-(Dimethylamino)pyridine (DMAP, Sigma-Aldrich, St. Louis, Mo.) pre-heated to 67° C. was added and mixed. Thus, the solvent in which the reaction was conducted consisted of 84% DMSO and 16% water, by volume. The mixture was kept at the same temperature for 30 min and then allowed to cool to room temperature over about one hour. The solution was mixed with 440 μL of water, and 24 μL of 5M aqueous NaCl was added and mixed. Crude product was separated by centrifugation. The pellet was dissolved in 6 mL of water and filtered through a regenerated cellulose membrane with a nominal molecular weight limit of 3,000 Daltons Louis, Mo.) to further purify the product, until obtaining 0.5 mL of retentate. 12 additional filtrations were conducted in which 1.5 mL of water was added to each retentate obtained. 500 μL of aqueous product was obtained after the last ultrafiltration.

Product derivatization extent was estimated after complete hydrolysis of 40 μL of aqueous purified product obtained above treated with 10 μL of 5M NaOH aqueous solution. UV absorbance at 254 nm of the resulting N-methylanthranoic acid and of RNA nucleotides were quantified using HPLC coupled to a Photo Diode Array (PDA) detector. It was found that about 93% of the nucleotides of UdsRNA had reacted. Lower concentrations of NMIA in the reaction mixture were used to obtain lower derivatization extents, namely between 13% and 56%. Reactions were also conducted at reaction temperatures as low as 47° C. and DMSO as low as 69%.

Figure 2:
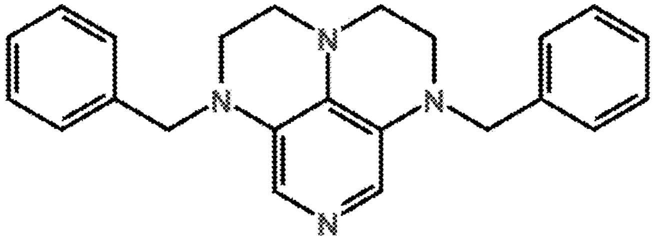
FIG. 2. Chemical structures representing three superDMAP nucleophiles.
Figure 2:
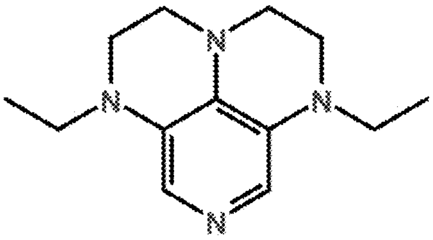
Figure 2:
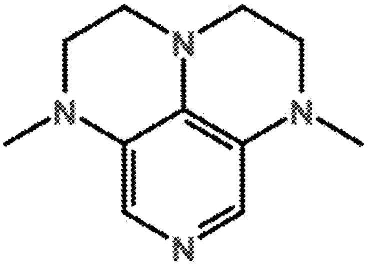

Reaction between UdsRNA and NMIA can also be conducted at different conditions. Reactions can be conducted lasting between 5 min and 30 minutes, at temperatures between 37° C. and 95° C., in solvents comprising between 10% DMSO and 64% DMSO, and between 11% water and 75% water, and between 11% ethyl acetate and 33% ethyl acetate, and having NaCl concentrations between 0.04M and 0.09M, and using a combination of BnsDMAP, EtsDMAP and MesDMAP (as shown in FIG. 2) instead of or in combination with DMAP. High temperature, high % DMSO but lower than 100%, and low NaCl concentration are found to be conducive to higher derivatization extents than low temperature, low % DMSO or close to 100% DMSO, or high NaCl concentration.

The following UdsRNA constructs prepared in Example 2 can also be separately reacted with NMIA: including, but not limited to, RNA_CPB_β-A_ds_ds, RNA_CPB_β-A_1-5_mut, RNA_CPB_β-A_1-7_del, RNA_CPB_β-A_1-7_mut, RNA_CPB_β-A_1-7_ins, RNA_CPB_β-A_1-10_mut, RNA_CPB_β-A_2-7_mut, RNA_CPB_β-A_2-7_ins. Derivatized RNA constructs obtained are named adding the prefix NMIA_to the originating RNA, namely NMIA_RNA_CPB_β-A_ds_ds, NMIA_RNA_CPB_β-A_1-7_del, NMIA_RNA_CPB_β-A_1-7_mut, NMIA_RNA_CPB_β-A_1-7_ins, NMIA_RNA_CPB_β-A_1-10_mut, NMIA_RNA_CPB_β-A_2-7_mut, NMIA_RNA_CPB_β-A_2-7_ins.

Example 4. Preparation of 2'-benzoate MdsRNA 12.5 μL of 3.2 g/L aqueous solution of RIFA_A_ds_ds (SEQ ID NO. 16) was added to 37.5 μL of dimethyl sulfoxide (DMSO, Sigma Aldrich, St. Louis, Mo., warmed to 67° C., and kept at this temperature. After 15 min at 67° C., 10 μL of 40.3 g/L DMSO solution of 4-(Dimethylamino) pyridine (DMAP, Sigma Aldrich, St. Louis, Mo.) pre-heated to 67° C. was added and mixed. Immediately afterwards, 20 μL of 218 g/L DMSO solution of BzCN (BOC Sciences, Shirley, N.Y.) pre-heated to 67° C. was added and mixed. The mixture was kept at the same temperature for 30 min and then allowed to cool to room temperature over about one hour. Isolation of MdsRNA was conducted similarly as described in Example 3.

Product derivatization extent was estimated similarly as described in Example 3. About 40% of the UdsRNA nucleotides were chemically modified. Lower concentrations of BzCN in the reaction mixture were used to obtain lower derivatization extents, namely 26% and 17%.

Example 5. Preparation of 2'-(2,4-dinitrophenoxy) MdsRNA 12.5 μL of 3.2 g/L aqueous solution of RIFA_A_ds_ds (SEQ ID NO. 16) was added to 45.5 μL of dimethyl sulfoxide (DMSO, Sigma Aldrich, St. Louis, Mo.), warmed to 67° C., and kept at this temperature. After 15 min at 67° C., 20 μL of 118 g/L DMSO solution of FDNB (Sigma Aldrich, St. Louis, Mo.) pre-heated to 67° C. was added and mixed. Immediately afterwards, 2 μL of 20.7 g/L aqueous solution of potassium carbonate (Sigma Aldrich, St. Louis, Mo.) pre-heated to 67° C. was added and mixed. The mixture was kept at the same temperature for 30 min and then allowed to cool to room temperature over about one hour. Isolation of MdsRNA was conducted similarly as described in Example 3. Product derivatization extent was estimated similarly as described in Example 3 and was found that about 23% of the nucleotides of substrate dsRNA had reacted. Lower concentrations of FDNB in the reaction mixture were used to obtain lower derivatization extents, namely 6% and 2%.

Example 6. Comparison of Properties of MdsRNA with Those of UdsRNA

MdsRNA in which about 40% of its nucleotides were reacted with BzCN as described in Example 4 was further characterized by testing its stability against digestion by RNase III. MdsRNA was found to have significantly improved stability against digestion by RNase III than UdsRNA.

For example, samples of about 600 ng of RNA before and after chemical modification using BzCN as described in Example 4 were incubated in separate experiments with 1 unit of RNase III (New England BioLabs, Ipswich, Mass.) in buffer recommended by supplier (50 mM Tris, 1 mM DTT, 50 mM NaCl, 20 mM $MnCl_2$) for 20 min at 37° C., then EDTA was added to final concentration of 50 mM. About 300 ng of RNA obtained after digestion with RNase III was denatured by heating for 10 min at 95° C. and analyzed by electrophoresis in NOVEX® denaturing 6% polyacrylamide TBE-Urea gels (Life Technologies) at 70° C. RNA bands were visualized by ethidium bromide staining (0.2 μg/ml) (Sigma-Aldrich, St. Louis, Mo.). FIG. 1. Shows that UdsRNA was completely degraded by RNase III treatment (compare bands before (lane A) and after (lane B) incubation with RNase III). In contrast, MdsRNA showed resistance to RNase III treatment, with significant full-length RNA still present after RNase treatment (compare bands before (lane A) and after (lane B) incubation with RNase III).

Lower water solubility for MdsRNA materials prepared as in examples 3, 4, and 5 than the corresponding water solubility of UdsRNA substrates was observed during their purification. This increased hydrophobicity was advantageously used for isolation purposes, thereby allowing their precipitation from aqueous solutions by simply increasing NaCl concentration. Furthermore, water solubility decreased with increasing derivatization extent. Therefore, such MdsRNA RNAi triggers are expected to diffuse more readily through biological membranes, which are hydrophobic, than the corresponding UdsRNA substrates.

Example 7. Efficacy of MdsRNAs Against Colorado Potato Beetle Infestation

To determine whether MdsRNAs targeting the β-actin gene of Colorado potato beetle exhibit similar or higher efficacy compared with UdsRNA targeting the same gene, MdsRNAs targeting potato beetle β-actin gene are generated as described.

UdsRNA prepared in Example 2 and MdsRNAs prepared as described in Example 3 can be used to test their efficacy on Colorado potato beetle. Each treatment or control sample is applied to the surface of a potato leaf disc. Control samples include post-transcriptionally derivatized unrelated UdsRNAs (negative control). Additional control experiments such as water to the surface of a potato leaf disc are also conducted. The treatment is allowed to dry on the leaf surface prior to test initiation. During a pretreatment period, all food is removed from beetle larval containers and larvae are starved for 4 hours before introduction to treated leaves. After the starvation period, a larva is placed on a treated potato leaf in a Petri dish, where it is allowed to feed on the disc until the leaf tissue is devoured. Larvae can be allowed multiple feedings at separate times on treated potato leaves, given a normal diet of potato leaves and then monitored for mortality daily. After the final exposure, larvae are maintained on untreated potato leaves for a period of time or until mortality, whichever occurred first. Throughout the experiment mortality assessments are conducted daily.

MdsRNAs prepared in Example 3 are expected to have similar or higher effectiveness than non-derivatized RNA constructs prepared in Example 2 in killing Colorado potato beetles by suppressing expression of the essential actin gene. The cohorts treated with water or with post-transcriptionally derivatized unrelated RNA construct (negative control) are expected to exhibit little or no mortality, indicating that such RNA constructs derivatized by reaction with NMIA are not inherently toxic to the beetles. A high degree of mortality of beetles in the cohorts consuming the MdsRNAs comprising the β-actin RNA post-transcriptionally derivatized with NMIA indicates that RNA constructs post-transcriptionally derivatized with NMIA constitute gene expression inhibitors. Similar or higher degree of mortality of beetles in the cohorts consuming the MdsRNAs comprising the beta actin RNA post-transcriptionally derivatized with NMIA than the mortality rate of non-derivatized RNA constructs indicates the improvement elicited by the post-transcriptional derivatization with NMIA.

Similar experiments can be carried out using MdsRNAs having other target genes in Colorado potato beetle or other target hosts.

Example 8. Field Efficacy of MdsRNAs

To determine whether MdsRNAs are similarly resistant or more resistant to environmental degradation than UdsRNAs, they can be applied to leaves on plants in a field, laboratory, or greenhouse. At various days after application, treated leaves are cut out of the plants and fed to target insects. The described MdsRNAs can be compared with UdsRNAs and control RNAs with respect to observed decreases in target host activity or increase target host morbidity.

MdsRNAs and control UdsRNA can also applied to plants grown in a field and allowed to dry on the leaf surface for a variable number of days to test persistence of the dsRNA. MdsRNA are expected to exhibit increased resistance to environmental degradation and to cause increased morbidity of the target host feeding on the treated plant leaf. Increased morbidity of target host in the cohorts consuming the MdsRNAs indicates the MdsRNA are effective in the treatment or control of the host Example 9. Efficacy of MdsRNAs Against Western Corn Rootworm Infestation The ability of the MdsRNAs to effectively inhibit target gene expression in host organisms can be tested by constructing DNA sequences for transcribing western corn rootworm sequence-containing RNA and transcribing and modifying the transcribed RNAs as described, followed by processing and feeding the resulting MdsRNAs. Bolognesi et al. (2012) describe a western corn rootworm sequence reported to produce RNAi precursors effective in suppressing expression of the western corn rootworm (*Diabrotica virgifera virgifera*) Snf7 ortholog, DvSnf7, when fed to the host insects. The western corn rootworm DvSnf7 gene encodes a critical component of the organism's endosomal sorting complex (ESCRT-III) and significant suppression of this essential gene results in larval death. Post-transcriptionally derivatized RNA constructs are prepared similarly as described in Example 3.

Bioassays are performed using a diet overlay methodology. Commercial western corn rootworm diet is prepared according to manufacturer's guidelines for SCR diet (Bio-Serv, Frenchtown, N.J.) with a few adjustments as described by Bolognesi et al. (2012) including the addition of Formalin at 0.06% (v/v), 10% KOH (v/v) to increase pH to 9, and lyophilized corn root tissue at 0.62% (w/v). 200 μl of molten diet is pipetted into 24 wells of 96 well plates (Falcon), and allowed to solidify at room temperature. Known amounts, ranging from 0.5 ng to 500 ng, of test sample and control samples comprising approximately 2-200 ng of non-derivatized or derivatized RNA are overlaid in each well. Non-derivatized controls include RNA_WCR_DvSnf7_ds, prepared similarly as RNA_CPB_ds as described in Example 2, described by Bolognesi et al. (2012) as effective in killing western corn rootworm by suppression of the DvSnf7 gene (positive control). Derivatized controls include a post-transcriptionally derivatized RNA entirely unrelated to western corn rootworm (negative control). Plates are air-dried and one larva is added per well. Plates are sealed with Mylar, ventilation holes added to each well with a #1 or #2 insect pin, and the plates incubated at 27° C. for 12 days. A cohort of 10 larvae are fed each individual DvSnf7 MdsRNAs or control sequence to provide ten data points for each experimental sample or control. Growth inhibition (larval size assessed from daily pictures) and mortality are determined for each cohort.

Each experimental and control cohort within the experiment is comprised of 10 individual larvae undergoing 10 identical treatments. Since the only way to ensure that an individual larva has consumed an entire dose, each larva is dosed in isolation. Any larvae that die in the course of the experimental procedure are processed to recover total mRNA and the sample preserved at −80° C. until further analysis can take place.

Once the 12-day experimental period is completed, the growth rate and overall mortality of each cohort is assessed and the remaining live larvae sacrificed and total mRNA recovered. The cohort treated with post-transcriptionally derivatized unrelated RNA construct are expected to exhibit little or no mortality, indicating that such RNA constructs derivatized by reaction with NMIA are not inherently toxic to the larvae. The cohort treated with positive controls are expected to exhibit a high degree of mortality, consistent with the observations of Bolognesi et al. (2012) that suppression of DvSnf7 gene expression by this dsRNA results in death of larvae that consume it. A high degree of mortality of larvae in the cohorts consuming the MdsRNAs comprising the RNA of Bolognesi et al. (2012) post-transcriptionally derivatized with NMIA indicates that RNA constructs post-transcriptionally derivatized with NMIA constitute effective RNAi triggers.

In all cases, the mRNA samples are analyzed by quantifying expression of the actin gene relative to standard markers and the results compared with the mortality rates exhibited by each experimental cohort. Reduced intact DvSnf7 mRNA indicates effective RNAi suppression of gene expression. Intact DvSnf7 mRNA can be measured by qPCR, qrtPCR, by differential Northern blot analysis or by similar quantitative methods.

Similar experiments can be performed using other sequences to western corn rootworm and sequences to other targets in other host organisms. The method of feeding is altered to correspond to the host organism. In some embodiments, these experiments are performed to identify the most potent RNA sequences. The MdsRNAs can also be manufactured in large scale and formulated for agricultural application.

Example 10. Efficacy of MdsRNAs Against Red Imported Fire Ant (RIFA)

The ability of the MdsRNAs to effectively inhibit gene expression in host insects was tested by producing MdsRNA targeting RIFA (*Solenopsis invicta* Buren) actin muscle (LOC105205816, GenBank: XM_011175337.1. The Red Imported Fire Ant's actin gene encodes a critical component of the organism's muscle and significant suppression of this essential gene results in insect death. RNA_RIFA_A_ds was prepared as described in Example 2. Seven aliquots of the RNA_RIFA_A_ds obtained were separately reacted with NMIA as described in Example 3, with BzCN as described in Example 4, and with FDNB as described in Example 5. The seven MdsRNAs obtained were named NMIA1_RNA_RIFA_A_ds, NMIA2_RNA_RIFA_A_ds, NMIA3_RNA_RIFA_A_ds, BzCN1_RNA_RIFA_A_ds, BzCN2_RNA_RIFA_A_ds, BzCN3_RNA_RIFA_A_ds, and FDNB_RNA_RIFA_A_ds.

A simple bioassay, similar to that described by Choi et al. (2012), was used to test the ability of MdsRNAs NMIA1_RNA_RIFA_A_ds, NMIA2_RNA_RIFA_A_ds, NMIA3_RNA_RIFA_A_ds, BzCN1_RNA_RIFA_A_ds, BzCN2_RNA_RIFA_A_ds, BzCN3_RNA_RIFA_A_ds, and FDNB_RNA_RIFA_A_ds to suppress essential gene expression and thereby kill or inhibit RIFA. This bioassay involved feeding for 4 days a group of 20 worker ants 50 μl of liquid per day containing the test substance at known concentration in 10% sucrose aqueous solution and measuring the mortality rate of worker ants. Each cohort consisted on 4 replicates of 20 ants each. Under test conditions mortality at ten days for ants fed a 10% sucrose solution with no added test RNA was 10%.

A high degree of mortality of ants was observed in the cohorts that consumed the MdsRNAs NMIA1_RNA_RIFA_A_ds, NMIA2_RNA_RIFA_A_ds, NMIA3_RNA_RIFA_A_ds, BzCN2_RNA_RIFA_A_ds, BzCN3_RNA_RIFA_A_ds, and FDNB_RNA_RIFA_A_ds. These results showed MdsRNAs were effective in killing RIFA. As shown in the table below, a similar or higher degree of mortality in cohorts that consumed the MdsRNAs was observed, compared to RIFA fed a 3-fold higher concentration of UdsRNA (RNA_RIFA_A_ds), indicating significant higher efficacy of MdsRNAs.

TABLE 1

Mortality in red imported fire ants following treatment with MdsRNA.

| Test substance | concentration ng/μl | % Mortality Day 10 | % Mortality Day 20 |
|---|---|---|---|
| BzCN1_RNA_RIFA_A_ds | 33 | 6 | 9 |
| BzCN2_RNA_RIFA_A_ds | 33 | 15 | 43 |
| BzCN3_RNA_RIFA_A_ds | 33 | 18 | 49 |
| NMIA1_RNA_RIFA_A_ds | 33 | 16 | 35 |
| NMIA2_RNA_RIFA_A_ds | 33 | 23 | 59 |
| NMIA3_RNA_RIFA_A_ds | 33 | 25 | 55 |
| FDNB_RNA_RIFA_A_ds | 33 | 33 | 75 |
| RNA_RIFA_A_ds | 99 | 21 | 30 |

Seven aliquots of the unrelated RNA_GFP_ds, can be separately reacted with NMIA as described in Example 3, with BzCN as described in Example 4, and with FDNB as described in Example 5. The seven chemically modified unrelated RNAs obtained are named NMIA1_RNA_GFP_ds, NMIA2_RNA_GFP_ds, NMIA3_RNA_GFP_ds, BzCN1_RNA_GFP_ds, BzCN2_RNA_GFP_ds, BzCN3_RNA_GFP_ds, and FDNB_RNA_GFP_ds. These chemically modified unrelated RNAs are expected to exhibit little or no mortality, indicating that such RNA constructs derivatized by reaction with NMIA, BzCN or FDNB are not inherently toxic to the ants.

In a separate experiment, RIFA_A_1-9_del (SEQ ID NO. 18), which comprises RIFA actin's sequence (SEQ ID NO. 17), can be used to prepare RNA transcript RNA_RIFA_A_1-9_del, in a similar manner as that described in Example 2 for preparing RNA_CPB_β-A_1-7_del. Post-transcriptionally derivatized RNA construct NMIA_RNA_RIFA_A_1-9_del is prepared similarly as NMIA_RNA_WCR_CPB_β-A_1-7_del as described in Example 3 and tested as described above.

Example 11. Efficacy of MdsRNAs Against *Fusarium graminearum* Infestation of Barley The ability of the materials described here to effectively trigger RNAi responses in host fungi is tested by producing MdsRNAs targeting cytochrome P450 lanosterol C-14α-demethylase (CYP51) genes of *Fusarium graminearum* (*Gibberella zeae*), delivering MdsRNAs to *Fusarium graminearum*. dsRNA with a sense strand comprising sections of CYP51A, CYP51B, and CYP51C genes, FG_CYP3 (SEQ ID NO. 19, named CYP3RNA in United States Patent Application 20160215290), and its corresponding antisense strand, FG_CYP3_antisense (SEQ ID NO. 9), are prepared as described by Koch et al. (2013). Five aliquots of the UdsRNA obtained are separately, reacted with NMIA as described in Example 3, with BzCN similarly as described in Example 4, and with FDNB similarly as described in Example 5. The five MdsRNA obtained are named NMIA1_RNA_FG_CYP3_ds, NMIA3_RNA_FG_CYP3_ds, BzCN1_RNA_FG_CYP3_ds, BzCN3_RNA_FG_CYP3_ds, and FDNB_RNA_FG_CYP3_ds.

In a separate experiment, FG_CYP3_2-10_mut (SEQ ID NO. 20), which comprises the FG_CYP3 sequence (SEQ ID NO. 19), is used to prepare RNA transcript RNA_FG_CYP3_2-10_mut, in a similar manner as that described in Example 2 for preparing RNA_CPB_β-A_2-7_mut. The CYP3 sequence comprises partial sequences of the three cytochrome P450 lanosterol C-14α-demethylase genes CYP51A, CYP51B, and CYP51C from *F. graminearum* and significant suppression of these genes results in resistance to infection on spring barley (*Hordeum vulgare*). MdsRNA NMIA_RNA_FG_CYP3_2-10_mut is prepared similarly as NMIA_RNA_WCR_CPB_β-A_2-7_mut as described in Example 3.

A simple bioassay similar to the one described by Koch et al. (2016), is used to test the ability of the materials to effectively inhibit gene expression in host fungi. The spring barley (*Hordeum vulgare*) cultivar Golden Promise is grown in a climate chamber under 16 h light photoperiod (240 μmol $m^{-2}$ $s^{-1}$ photon flux density) at 18° C./14° C. (day/night) and 65% relative humidity. Detached leaves of three-week-old barley plants are transferred into square Petri dishes (120×120×17 mm) containing 1% agar. Test and negative control (dsRNA targeting Green Fluorescent Protein) substances are diluted in 500 μL water to a known final concentration of about between 2 and 200 ng/μL, corresponding to about between 1 and 100 μg test or control substance per plate. Leaves are sprayed using a spray flask (10 mL capacity). *Fusarium graminearum* is cultured on synthetic nutrient-poor agar medium (Koch et al. 2012). Each dish containing six detached leaves is evenly sprayed with test or control substance and 48 hours later drop-inoculated with *F. graminearum* (20 μL of a solution containing $2\times10^4$ conidia/mL). Plates are incubated at room temperature under constant illumination from one near-UV tube (PhillipsTLD36W/08) and one white-light tube (PhillipsTLD 36W/830HF).

At six days after inoculation, leaves treated in different experiments with NMIA1_RNA_CYP3_ds, NMIA3_RNA_CYP3_ds, BzCN1_RNA_CYP3_ds, BzCN3_RNA_CYP3_ds, FDNB_RNA_CYP3_ds, or NMIA_RNA_FG_CYP3_2-10_mut are expected to develop brownish lesions that are substantially smaller than those treated with control-sprayed leaves. Quantitative real-time PCR analysis of fungal DNA levels can be used to confirm reduced fungal growth on leaves treated with NMIA1_RNA_CYP3_ds, NMIA3_RNA_CYP3_ds, BzCN1_RNA_CYP3_ds, BzCN3_RNA_CYP3_ds, FDNB_RNA_CYP3_ds, or NMIA_RNA_FG_CYP3_2-10_mut. These results would indicate that MdsRNA-containing compositions comprising RNA constructs post-transcriptionally derivatized with NMIA constitute effective RNAi triggers useful for controlling fungal diseases of plants.

Similar experiments can be performed using other sequences to *F. graminearum* and sequences to other targets in other host fungi. The method of feeding is altered to correspond to the host organism. In some embodiments, these experiments are performed to identify the most potent RNA sequences. The MdsRNAs can also be manufactured in large scale and formulated for agricultural application.

Example 12. Efficacy of MdsRNAs Against Diamondback Moth (*Plutella xylostella*) Infestation The ability of the MdsRNAs to inhibit gene expression in host lepidoptera can be tested by producing MdsRNAs targeting one of Acetylcholinesterase (AChE, EC3.1.1.7) genes of *Plutella xylostella*, and delivering the MdsRNAs to *Plutella xylostella*. The Diamondback moth Acetylcholinesterase gene encodes an enzyme essential for catalyzing the hydrolysis of the neurotransmitter acetylcholine to terminate neurotransmission and significant suppression of this essential gene results in death. dsRNA targeting Acetylcholinesterase (AChE, EC3.1.1.7) gene (SEQ ID NO. 21, GenBank: AY061975.1, nucleotides#512-810) was prepared using sequence DBM_AChE2_ds (SEQ ID NO. 9), similarly as described in Example 2. Five aliquots of the UdsRNA obtained, named RNA_DBM_AChE2_ds, were separately reacted, with NMIA similarly as described in Example 3, with BzCN similarly as described in Example 4, and with FDNB similarly as described in Example 5. The five MdsRNA obtained were named NMIA1_RNA_DBM_AChE2_ds, NMIA3_RNA_DBM_AChE2, BzCN1_RNA_DBM_AChE2_ds, BzCN3_RNA_DBM_AChE2_ds, and FDNB_RNA_DBM_AChE2_ds.

In a separate experiment, DBM_AChE2_2-10_mut (SEQ ID NO. 22), which comprises a section of one of *Plutella xylostella*'s Acetylcholinesterase (AChE, EC3.1.1.7) genes (GenBank: AY061975.1 nucleotides#512-810) (SEQ ID NO. 21), can be used to prepare RNA transcript RNA_DBM_AChE2_2-10_mut, in a similar manner as that described in Example 2 for preparing RNA_CPB_β-A_2-7_mut. Post-transcriptionally derivatized RNA construct (MdsRNA) NMIA_RNA_DBM_AChE2_2-10_mut can be prepared similarly as NMIA_RNA_WCR_CPB_β-A_2-7_mut as described in Example 3.

Bioassays are performed in vitro by using a leaf-spray method, as described by Gong et al. (2011). A population of *P. xylostella* is originally collected from insecticide-free cabbage field, and maintained on the cabbage leaves at 25±1° C., 16:8 h light:dark photoperiod and 60-70% relative humidity until pupation. Test and control substances are uniformly coated on each side of cabbage leaves to form sandwiches at known concentrations. Second instar larvae of *P. xylostella* are used for each treatment and the insects are starved for 12 h before testing. Known amounts, ranging from 0.03 μg/cm2 to 300 μg/cm2 of NMIA_RNA_DBM_AChE2_2-10_mut, control samples comprising a water only control, RNA sequences entirely unrelated to diamondback moth, and non-derivatized samples RNA_DBM_AChE2_2-10_mut are sprayed at concentrations ranging from 10 to 200 (μg/ml). Fresh cabbage discs (2 cm diameter) are placed on wet filter paper in a Petri dish (9 cm diameter). Ten second instar larvae of *P. xylostella* are transferred to leaf and sprayed (1 mL solution). Each concentration of MdsRNA or control is applied with four replicates. The treated larvae are allowed to feed on the treated leaves for 72 h at 26±1° C., 60-70% relative humidity and 16:8 h (light: dark) photoperiod, and the larval mortality is recorded after 72 h. The larvae are considered to be dead when they stop moving in response to touch. Growth inhibition (larval size assessed from daily pictures) and mortality are determined for each cohort. Any larvae that die in the course of the experimental procedure are processed to recover total mRNA and the sample preserved at −80° C. until further analysis can take place.

Once the 72-hour experimental period is completed, the growth rate and overall mortality of each cohort is assessed and the remaining live larvae sacrificed and total mRNA recovered. The cohort treated with unrelated RNA are expected to exhibit little or no mortality, indicating that such RNA constructs post-transcriptionally derivatized are not inherently toxic to the larvae. Increasing mortality of larvae in the cohorts consuming NMIA1_RNA_DBM_AChE2_ds, NMIA3_RNA_DBM_AChE2, BzCN1_RNA_DBM_AChE2_ds, BzCN3_RNA_DBM_AChE2_ds, FDNB_RNA_DBM_AChE2_ds, or NMIA_RNA_DBM_AChE2_2-10_mut indicates that the MdsRNAs are effective for inhibiting gene expression in the host. Similar or higher mortality of larvae in the cohorts consuming NMIA1_RNA_DBM_AChE2_ds, NMIA3_RNA_DBM_AChE2, BzCN1_RNA_DBM_AChE2_ds, BzCN3_RNA_DBM_AChE2_ds, FDNB_RNA_DBM_AChE2_ds, or NMIA_RNA_DBM_AChE2_2-10_mut than in the cohorts consuming RNA_DBM_AChE2_ds and RNA_DBM_AChE2_2-10_mut indicates that MdsRNAs have higher efficacy than UdsRNAs.

In all cases, the mRNA samples are analyzed by quantifying expression of the AChE2 gene relative to standard markers and the results compared with the mortality rates exhibited by each experimental cohort. Reduced intact AChE2 mRNA indicates effective suppression of gene expression. Intact AChE2 mRNA can be measured by qPCR, qrtPCR, by differential Northern blot analysis or by similar quantitative methods.

Similar experiments can be performed using other sequences to *P. xylostella* and sequences to other targets in other host lepidoptera. The method of feeding is altered to correspond to the host lepidoptera. In some embodiments, these experiments are performed to identify the most potent RNA sequences. The MdsRNAs can also be manufactured in large scale and formulated for agricultural application.

Example 13. Efficacy of MdsRNAs Followed by Application of a Neonicotinoid Insecticide Against Insecticide-Resistant Asian Citrus Psyllid The described MdsRNAs can be combined with known treatments, such as insecticides, to further enhance treatment or control of infestation. An MdsRNA, such as ACP_CYP4_2-10_mut (SEQ ID NO. 24), comprising sections of three of *Diaphorina citri* cytochrome P450-like genes (GenBank: XM_017448211.1 nucleotides#1357-1436, GenBank: XM_017446566.1 nucleotides#1878-1957, GenBank: XM_017443370.1 nucleotides#854-933; SEQ ID NO. 23) can be manufactured and applied topically to an insect, such as Asian citrus psyllid, or a plant on which the insect feeds. Subsequently, an insecticide, such as neonicotinoid, can be applied topically to the insect or plant. Alternatively, an insecticide can be applied first or concurrent with MdsRNAs. Asian citrus psyllid's cytochrome P450 monooxygenases genes encodes enzymes involved in the metabolism of xenobiotic compounds in insects resistant to insecticides and significant suppression of these genes results in death upon administration of insecticides. MdsRNA NMIA_RNA_ACP_CYP4_2-10_mut is prepared similarly as NMIA_RNA_WCR_CPB_β-A_2-7_mut as described in Example 3. MdsRNAs targeted to these CYP4 genes are produced and topically applied to Asian citrus psyllid adults along with experimental controls followed by application of the neonicotinoid insecticide imidacloprid.

Bioassays are performed in vitro by using a leaf-spray method, as described by Killini et al. (2014). Field populations of *D. citri* are collected from commercial citrus groves in Florida, for example from Polk County or Lake County, the great majority of which are insecticide resistant. Purified samples of NMIA_RNA_ACP_CYP4_2-10_mut, RNA sequences entirely unrelated to Asian citrus psyllid, and non-derivatized samples RNA_ACP_CYP4_2-10_mut are serially diluted using RNase-free water to obtain desired concentrations of RNAi triggers and control samples. RNAi triggers and controls at concentrations ranging from (0.5 ng/mL to 1000 ng/mL) and another negative control using just RNase-free water are used to treat *D. citri* adults. *D. citri* adults are anaesthetized under $CO_2$ within a few hours of eclosion. A 0.2 mL droplet containing between 0.1 and 200 ng of test and control samples are topically applied to the ventral side of the thorax using a 10 mL Hamilton syringe. Five (5) treated adults are placed into each 60-mm plastic disposable Petri dishes that are lined with citrus leaf disks, as a food source, over agar beds as described by Tiwari, S. et al. (2012) "Biochemical basis of organophosphate and carbamate resistance in Asian citrus psyllid" J Econ Entomol 105: 540-548. Petri dishes with Asian citrus psyllid adults are kept at 25±1° C. and 50±5% relative humidity with a 14:10 h light:dark photoperiod, in a growth chamber for 72 h.

Treated adult insects are then transferred to new Petri dishes that contain leaf discs treated with insecticide solution. Briefly, the leaf disks (60 mm diameter) are excised, dipped in the insecticide solution made in acetone for 30 s, and allowed to air dry in a fume hood for 1 h prior to placement into the Petri dishes as described by Tiwari et al. 2011. Analytical-grade imidacloprid at the $LD_{50}$ dosage (0.02 ng active ingredient/ml acetone) previously determined by Tiwari et al. 2011. The mortality of *D. citri* adults is assessed after 24 h. Five replicates (Petri dishes), with five insects each, are performed for each of the *D. citri* populations tested. Live insects are counted daily.

The cohorts pre-treated with unrelated RNA are expected to exhibit little or no mortality, indicating that such RNA constructs post-transcriptionally derivatized do not abrogate insecticide resistance. Increasing mortality of insects in the cohorts pre-treated with NMIA_RNA_ACP_CYP4_2-10_mut indicates the MdsRNAs are effective for eliciting RNAi responses. Similar or higher mortality of insects in the cohorts pre-treated with NMIA_RNA_ACP_CYP4_2-10_mut than in the cohorts pre-treated with RNA_ACP_CYP4_2-10_mut indicates MdsRNA constitute an improvement over non-derivatized RNAi triggers.

Similar experiments can be performed using other sequences to *D. citri* and sequences to other targets in other host pests. The MdsRNAs can also be combined with other pest treatments, including, but not limited to, fungicides, herbicides and other insecticides. The method of feeding is altered to correspond to the host pest. In some embodiments, these experiments are performed to identify the most potent RNA sequences. The MdsRNAs can also be manufactured in large scale and formulated for agricultural application.

Example 14. Sample Sequences

Sequences referred to in the above examples. Additional exemplary sequences are provided that can be used in the production of UdsRNA for post transcriptional modification and use in inhibiting expression of target genes in host organisms.

TABLE 2

| Plasmid pMA sequence (SEQ ID NO. 1) having a T7 promoter (nucleotides 320-342), multiple cloning site (MCS, 351-500), ColE1 origin of replication, (ori, 653-1320), and Ampicillin resistance gene (AmpR, 1468-2328). | |
|---|---|
| ctaaattgta agcgttaata ttttgttaaa attcgcgtta aatttttgtt aaatcagctc | 60 |
| atttttaac caataggccg aaatcggcaa aatcccttat aaatcaaaag aatagaccga | 120 |
| gatagggttg agtggccgct acagggcgct cccattcgcc attcaggctg cgcaactgtt | 180 |
| gggaagggcg tttcggtgcg ggcctcttcg ctattacgcc agctggcgaa agggggatgt | 240 |
| gctgcaaggc gattaagttg ggtaacgcca gggttttccc agtcacgacg ttgtaaaacg | 300 |
| acggccagtg agcgcgacgt aatacgactc actatagggc gaattggcgg aaggccgtca | 360 |
| aggcctaggc gcgccatgag ctctaaagct tcgctcgagc tgcggccgca cggatcctcg | 420 |
| aattcccaag cttatctcga gtagcggccg cttggatccc agaattctag gtacctctta | 480 |
| attaactggc ctcatgggcc ttccgctcac tgcccgcttt ccagtcggga aacctgtcgt | 540 |
| gccagctgca ttaacatggt catagctgtt tccttgcgta ttgggcgctc tccgcttcct | 600 |
| cgctcactga ctcgctgcgc tcggtcgttc gggtaaagcc tggggtgcct aatgagcaaa | 660 |
| aggccagcaa aaggccagga accgtaaaaa ggccgcgttg ctggcgtttt tccataggct | 720 |
| ccgcccccct gacgagcatc acaaaaatcg acgctcaagt cagaggtggc gaaacccgac | 780 |
| aggactataa agataccagg cgtttccccc tggaagctcc ctcgtgcgct ctcctgttcc | 840 |
| gaccctgccg cttaccggat acctgtccgc ctttctccct tcgggaagcg tggcgctttc | 900 |
| tcatagctca cgctgtaggt atctcagttc ggtgtaggtc gttcgctcca agctgggctg | 960 |
| tgtgcacgaa ccccccgttc agcccgaccg ctgcgcctta tccggtaact atcgtcttga | 1020 |
| gtccaacccg gtaagacacg acttatcgcc actggcagca gccactggta acaggattag | 1080 |
| cagagcgagg tatgtaggcg gtgctacaga gttcttgaag tggtggccta actacggcta | 1140 |
| cactagaaga acagtatttg gtatctgcgc tctgctgaag ccagttacct tcggaaaaag | 1200 |
| agttggtagc tcttgatccg gcaaacaaac caccgctggt agcggtggtt tttttgtttg | 1260 |
| caagcagcag attacgcgca gaaaaaaagg atctcaagaa gatcctttga tcttttctac | 1320 |
| ggggtctgac gctcagtgga acgaaaactc acgttaaggg attttggtca tgagattatc | 1380 |
| aaaaaggatc ttcacctaga tccttttaaa ttaaaaatga agttttaaat caatctaaag | 1440 |
| tatatatgag taaacttggt ctgacagtta ccaatgctta atcagtgagg cacctatctc | 1500 |
| agcgatctgt ctatttcgtt catccatagt tgcctgactc cccgtcgtgt agataactac | 1560 |
| gatacgggag ggcttaccat ctggccccag tgctgcaatg ataccgcgag aaccacgctc | 1620 |
| accggctcca gatttatcag caataaacca gccagccgga agggccgagc gcagaagtgg | 1680 |
| tcctgcaact ttatccgcct ccatccagtc tattaattgt tgccgggaag ctagagtaag | 1740 |
| tagttcgcca gttaatagtt tgcgcaacgt tgttgccatt gctacaggca tcgtggtgtc | 1800 |
| acgctcgtcg tttggtatgg cttcattcag ctccggttcc caacgatcaa ggcgagttac | 1860 |

TABLE 2-continued

| Plasmid pMA sequence (SEQ ID NO. 1) having a T7 promoter (nucleotides 320-342), multiple cloning site (MCS, 351-500), ColE1 origin of replication, (ori, 653-1320), and Ampicillin resistance gene (AmpR, 1468-2328). |
|---|
| atgatccccc atgttgtgca aaaaagcggt tagctccttc ggtcctccga tcgttgtcag 1920 |
| aagtaagttg gccgcagtgt tatcactcat ggttatggca gcactgcata attctcttac 1980 |
| tgtcatgcca tccgtaagat gcttttctgt gactggtgag tactcaacca agtcattctg 2040 |
| agaatagtgt atgcggcgac cgagttgctc ttgcccggcg tcaatacggg ataataccgc 2100 |
| gccacatagc agaactttaa aagtgctcat cattggaaaa cgttcttcgg ggcgaaaact 2160 |
| ctcaaggatc ttaccgctgt tgagatccag ttcgatgtaa cccactcgtg cacccaactg 2220 |
| atcttcagca tcttttactt tcaccagcgt ttctgggtga gcaaaaacag gaaggcaaaa 2280 |
| tgccgcaaaa aagggaataa gggcgacacg gaaatgttga atactcatac tcttcctttt 2340 |
| tcaatattat tgaagcattt atcagggtta ttgtctcatg agcggataca tatttgaatg 2400 |
| tatttagaaa aataaacaaa taggggttcc gcgcacattt ccccgaaaag tgccac 2456 |

TABLE 3

| Target gene sequences |
|---|
| SEQ ID NO. 13 *Leptinotarsa decemlineata* strain Freeville β-actin sequence, *Leptinotarsa decemlineata* strain Freeville actin mRNA, GenBank ID: KJ577616.1, nt #s: 1-297 |
| gcacgaggtt tttctgtcta gtgagcagtg tccaacctca aaagacaaca tgtgtgacga 60 |
| cgatgtagcg gctcttgtcg tagacaatgg atccggtatg tgcaaagccg gtttcgcagg 120 |
| agatgacgca ccccgtgccg tcttcccctc gatcgtcggt cgcccaaggc atcaaggagt 180 |
| catggtcggt atgggacaaa aggactcata cgtaggagat gaagcccaaa gcaaaagagg 240 |
| tatcctcacc ctgaaatacc ccatcgaaca cggtatcatc accaactggg atgacat 297 |
| SEQ ID NO. 14 Section of western corn rootworm's (*Diabrotica virgifera virgifera* LeConte) Snf7 ortholog, DvSnf7 (Bolognesi et al. 2012) |
| gcaaagaaaa atgcgtcgaa aaataaaaga gttgcactcc aagccctcaa aaagaagaaa 60 |
| cgattggaaa agacccaact acaaatagat ggaaccctta caactattga aatgcagagg 120 |
| gaagccctcg aaggagctag cacaaatact gctgtattag attctatgaa aaatgctgca 180 |
| gatgccctta agaaagctca taagaatttg aatgtagatg atgttcacga tatcatgga 239 |
| SEQ ID NO. 17 *Solenopsis invicta* muscle actin (LOC105205816) (GenBank: XM_011175337.1 nucleotides #465-763) |
| gatctctctc cctcgactct aacaccagcg aaagtaacag ccaatcaaga tgtgtgacga 60 |
| tgatgttgcg gcattagtcg tggacaatgg gtccggtatg tgcaaggctg gattcgcggg 120 |
| ggatgatgca ccacgcgctg tgtttcccag catcgtcggt cgtcctcgtc atcagggtgt 180 |
| gatggtcggt atgggtcaaa aagacagtta tgttggcgac gaggcgcaaa gtaagagagg 240 |
| tatattgaca ctaaagtatc ctatagaaca tggcattatt actaattggg atgacatgg 299 |
| SEQ ID NO. 19 *F. graminearum* sections of cytochrome P450 lanosterol C-14alpha-demethylase CYP51A, CYP51B, and CYP51C genes. |
| cagcaagttt gacgagtccc tggccgctct ctaccacgac ctcgatatgg gcttcacccc 60 |
| catcaacttc atgcttcact gggcccctct cccctggaac cgtaagcgcg accacgccca 120 |
| gcgcactgtt gccaagatct acatggacac tatcaaggag cgccgcgcca agggcaacaa 180 |
| cgaatccgag catgacatga tgaagcacct tatgaactct ccatggcggc cgcgggaatt 240 |

TABLE 3-continued

| Target gene sequences | |
|---|---|
| cgatatcggt ccattgacaa tccccgtctt tggtagcgat gtcgtatacg attgtcccaa | 300 |
| ctcgaagctc atggaacaaa agaagtttgt caagtttggc cttacgcaaa aagcactcga | 360 |
| gtcacacgtc cagttaatcg agcgagaggt tcttgactac gtcgaaactg atccatcctt | 420 |
| ttctggcaga actagcacca tcgatgtccc caaggcaatg gctgagataa caatctttac | 480 |
| tgcctcacgt tctttgcagg gtgaggaagt tcggagaaaa ctcactgccg agtttgctgc | 540 |
| cactagtatt ggaagcaccg tacaatatgg catcgacccg tacgcttttt tcttcgactg | 600 |
| cagagataaa tacggcgact gctttacctt tattctcctt ggcaaatcaa cgactgtctt | 660 |
| tcttggtccc aagggcaatg actttatcct caacggcaaa cacgccgatc tcaacgccga | 720 |
| ggacgtttat gggaaactta ccacgcccgt gtttggtgag gaggttgttt atgactgctc | 780 |
| caatg | 785 |
| SEQ ID NO. 21 *Plutella xylostella* Acetylcholinesterase (GenBank: AY061975.1 nucleotides #512-810 | |
| catatcggag gattgcctct atttgaacat atgggtgccg cagcacttgc gcgtccgtca | 60 |
| ccatcaggac aagccattaa ccgagcgacc gaaggttcca atactagtgt ggatttacgg | 120 |
| cgggggttac atgagtggca cggcgacact tgatctatat aaagccgaca taatggcgtc | 180 |
| ttcgagtgat gtgatcgtag cctcgatgca gtatagggtt ggcgcgtttg gatttttgta | 240 |
| ccttaacaaa tatttttccc ctggtagcga ggaagcggca ggaaatatgg gcttgtggg | 299 |
| SEQ ID NO. 23 Sections of *Diaphorina citri* cytochrome P450-like genes (GenBank: XM_017448211.1 nucleotides #1357-1436, GenBank: XM_017446566.1 nucleotides #1878-1957, GenBank: XM_017443370.1 nucleotides #854-933) | |
| gtcgagataa gagaagaagt tgacacgttc atgtttgagg gacacgacac aacaacagcc | 60 |
| ggaatctgct ggtctctctt cgagaacatc agggaagagg ttgacacgtt catgtttgaa | 120 |
| ggacatgaca caacatcggc agccatctgt tggacactgc atgagaacat cagggaagag | 180 |
| gtagacacgt tcatgtttga aggtcatgac acaacttcgg cagccatctg ttggactctg | 240 |
| SEQ ID NO. 9 Antisense to *F. graminearum* sections of cytochrome P450 lanosterol C-14alpha-demethylase CYP51A, CYP51B, and CYP51C genes (SEQ ID NO. 19). | |
| cattggagca gtcataaaca acctcctcac caaacacggg cgtggtaagt ttcccataaa | 60 |
| cgtcctcggc gttgagatcg gcgtgtttgc cgttgaggat aaagtcattg cccttgggac | 120 |
| caagaaagac agtcgttgat ttgccaagga gaataaaggt aaagcagtcg ccgtatttat | 180 |
| ctctgcagtc gaagaaaaaa gcgtacgggt cgatgccata ttgtacggtg cttccaatac | 240 |
| tagtggcagc aaactcggca gtgagttttc tccgaacttc ctcaccctgc aaagaacgtg | 300 |
| aggcagtaaa gattgttatc tcagccattg ccttggggac atcgatggtg ctagttctgc | 360 |
| cagaaaagga tggatcagtt tcgacgtagt caagaacctc tcgctcgatt aactggacgt | 420 |
| gtgactcgag tgctttttgc gtaaggccaa acttgacaaa cttcttttgt tccatgagct | 480 |
| tcgagttggg acaatcgtat acgacatcgc taccaaagac ggggattgtc aatggaccga | 540 |
| tatcgaattc ccgcggccgc catggagagt tcataaggtg cttcatcatg tcatgctcgg | 600 |
| attcgttgtt gcccttggcg cggcgctcct tgatagtgtc catgtagatc ttggcaacag | 660 |
| tgcgctgggc gtggtcgcgc ttacggttcc aggggagagg ggcccagtga agcatgaagt | 720 |
| tgatgggggt gaagcccata tcgaggtcgt ggtagagagc ggccagggac tcgtcaaact | 780 |
| tgctg | 785 |

TABLE 4

RNA expression vectors for expressing precursor RNA sequences effective in suppressing expression of target genes, comprising a promoter, a target gene sense sequence with inserted, deleted or mutated nucleotides, sequence generating a single strand RNA loop, a target gene antisense sequence, and a nuclease restriction site.

SEQ ID NO. 3 Comprising a section of *Leptinotarsa decemlineata* strain Freeville β-actin sense sequence (SEQ ID NO. 13).

```
atttaggtga cactatagaa gcacgaggtt tttctgtcta gtgagcagtg tccaacctca    60
aaagacaaca tgtgtgacga cgatgtagcg gctcttgtcg tagacaatgg atccggtatg   120
tgcaaagccg gtttcgcagg agatgacgca ccccgtgccg tcttcccctc gatcgtcggt   180
cgcccaaggc atcaaggagt catggtcggt atgggacaaa aggactcata cgtaggagat   240
gaagcccaaa gcaaaagagg tatcctcacc ctgaaatacc ccatcgaaca cggtatcatc   300
accaactggg atgacatttc ttgtcccttc accttatacc tcatcctact ttcattattc   360
atataaacta ttactcacac atatcacaac tctgtcctcc tattaatatc cttctgttct   420
ctataaacta ccttattcta ctgttcatcc tcctcccatc atcctcgatg tcatcccagt   480
tggtgatgat accgtgttcg atggggtatt tcagggtgag gatacctctt ttgctttggg   540
cttcatctcc tacgtatgag tccttttgtc ccataccgac catgactcct tgatgccttg   600
ggcgaccgac gatcgagggg aagacggcac ggggtgcgtc atctcctgcg aaaccggctt   660
tgcacatacc ggatccattg tctacgacaa gagccgctac atcgtcgtca cacatgttgt   720
cttttgaggt tggacactgc tcactagaca gaaaaacctc gtgcccatgg              770
```

SEQ ID NO. 4 Comprising a section of *Leptinotarsa decemlineata* strain Freeville β-actin sequence (SEQ ID NO. 13) with one nucleotide every six contiguous nucleotides of the sense strand sequence mutated to its complementary nucleotide, e.g. A was replaced by T, C was replaced by G

```
atttaggtga cactatagaa ggacgagctt tttgtgtctt gtgaggagtg tgcaaccaca    60
aaacacaact tgtgtcacga ccatgtaccg gctgttgtcc tagactatgg aaccggtttg   120
tgctaagccc gtttcccagg acatgaccca cccggtgccc tcttcgcctc gttcgtccgt   180
cgcgcaaggg atcaacgagt cttggtccgt atgcgacaat aggacacata cctaggacat   240
gaaccccaat gcaaatgagg tttcctctcc ctgtaatacg ccatccaaca ccgtatcttc   300
acctactggc atgacttttc ttgtcccttc accttatacc tcatcctact ttcattattc   360
atataaacta ttactcacac atatcacaac tctgtcctcc tattaatatc cttctgttct   420
ctataaacta ccttattcta ctgttcatcc tcctcccatc atcctcgatg tcatcccagt   480
tggtgatgat accgtgttcg atggggtatt tcagggtgag gatacctctt ttgctttggg   540
cttcatctcc tacgtatgag tccttttgtc ccataccgac catgactcct tgatgccttg   600
ggcgaccgac gatcgagggg aagacggcac ggggtgcgtc atctcctgcg aaaccggctt   660
tgcacatacc ggatccattg tctacgacaa gagccgctac atcgtcgtca cacatgttgt   720
cttttgaggt tggacactgc tcactagaca gaaaaacctc gtgcccatgg              770
```

SEQ ID NO. 5 Comprising a section of *Leptinotarsa decemlineata* strain Freeville β-actin sequence (SEQ ID NO. 13) with one nucleotide every eight contiguous nucleotides of the sense strand sequence deleted.

```
atttaggtga cactatagaa gacgaggttt tctgttagtg agagtgtcca cctcaaagac    60
aactgtgtga gacgatgagc ggctttgtcg tgacaatgat ccggttgtgc aagccggttc   120
gcaggaatga cgcccccgtg cgtcttccct cgatgtcggt ccccaaggat caagggtcat   180
ggcggtatgg acaaaagact catcgtagga atgaagccaa agcaaagagg ttcctcacct   240
```

TABLE 4-continued

RNA expression vectors for expressing precursor RNA sequences effective in suppressing expression of target genes, comprising a promoter, a target gene sense sequence with inserted, deleted or mutated nucleotides, sequence generating a single strand RNA loop, a target gene antisense sequence, and a nuclease restriction site.

| | |
|---|---|
| gaaatcccca tcaacacgga tcatcacaac tggatgacat ttcttgtccc ttcaccttat | 300 |
| acctcatcct actttcatta ttcatataaa ctattactca cacatatcac aactctgtcc | 360 |
| tcctattaat atccttctgt tctctataaa ctaccttatt ctactgttca tcctcctccc | 420 |
| atcatcctcg atgtcatccc agttggtgat gataccgtgt tcgatggggt atttcagggt | 480 |
| gaggatacct cttttgcttt gggcttcatc tcctacgtat gagtcctttt gtcccatacc | 540 |
| gaccatgact ccttgatgcc ttgggcgacc gacgatcgag gggaagacgg cacggggtgc | 600 |
| gtcatctcct gcgaaaccgg ctttgcacat accggatcca ttgtctacga caagagccgc | 660 |
| tacatcgtcg tcacacatgt tgtcttttga ggttggacac tgctcactag acagaaaaac | 720 |
| ctcgtgccca tgg | 733 |

SEQ ID NO. 6 Comprising a section of *Leptinotarsa decemlineata* strain Freeville β-actin sequence (SEQ ID NO. 13) with one nucleotide every eight contiguous nucleotides of the sense strand sequence mutated to its complementary nucleotide, e.g. A was replaced by T, C was replaced by G

| | |
|---|---|
| atttaggtga cactatagaa ggacgaggta tttctgtgta gtgaggagtg tcctacctca | 60 |
| atagacaact tgtgtgagga cgatgaagcg gctgttgtcg ttgacaatgc atccggtttg | 120 |
| tgcaatgccg gttacgcagg acatgacgct ccccgtggcg tcttcgcctc gatggtcggt | 180 |
| cccccaaggg atcaaggtgt catggacggt atgcgacaaa acgactcatt cgtaggacat | 240 |
| gaagcgcaaa gcataagagg tttcctcacg ctgaaattcc ccatccaaca cggaatcatc | 300 |
| agcaactggc atgacatttc ttgtcccttc accttatacc tcatcctact ttcattattc | 360 |
| atataaacta ttactcacac atatcacaac tctgtcctcc tattaatatc cttctgttct | 420 |
| ctataaacta ccttattcta ctgttcatcc tcctcccatc atcctcgatg tcatcccagt | 480 |
| tggtgatgat accgtgttcg atggggtatt tcagggtgag gatacctctt ttgctttggg | 540 |
| cttcatctcc tacgtatgag tccttttgtc ccataccgac catgactcct tgatgccttg | 600 |
| ggcgaccgac gatcgagggg aagacggcac ggggtgcgtc atctcctgcg aaaccggctt | 660 |
| tgcacatacc ggatccattg tctacgacaa gagccgctac atcgtcgtca cacatgttgt | 720 |
| cttttgaggt tggacactgc tcactagaca gaaaaacctc gtgcccatgg | 770 |

SEQ ID NO. 7 Comprising a section of *Leptinotarsa decemlineata* strain Freeville β-actin sequence (SEQ ID NO. 13) with one guanine nucleotide added every seven contiguous nucleotides of the sense strand sequence.

| | |
|---|---|
| atttaggtga cactatagaa ggcacgaggg tttttctggt ctagtggagc agtggtccaa | 60 |
| cgctcaaaag gacaacagtg tgtgagcgac gatggtagcg ggctcttgtg cgtagacgaa | 120 |
| tggatgccgg tatggtgcaa aggccggttg tcgcagggag atgacggcac cccggtgccg | 180 |
| tgcttccccg tcgatcggtc ggtcggccca agggcatcaa gggagtcatg ggtcggtgat | 240 |
| gggacgaaaa ggagctcata cggtaggagg atgaagcgcc aaagcgaaaa gagggtatcc | 300 |
| tgcaccctgg aaataccgcc atcgagacac ggtgatcatc agccaactgg ggatgacgat | 360 |
| ttcttgtccc ttcaccttat acctcatcct actttcatta ttcatataaa ctattactca | 420 |
| cacatatcac aactctgtcc tcctattaat atccttctgt tctctataaa ctaccttatt | 480 |
| ctactgttca tcctcctccc atcatcctcg atgtcatccc agttggtgat gataccgtgt | 540 |

TABLE 4-continued

| RNA expression vectors for expressing precursor RNA sequences effective in suppressing expression of target genes, comprising a promoter, a target gene sense sequence with inserted, deleted or mutated nucleotides, sequence generating a single strand RNA loop, a target gene antisense sequence, and a nuclease restriction site. | |
|---|---|
| tcgatggggt atttcagggt gaggatacct cttttgcttt gggcttcatc tcctacgtat | 600 |
| gagtcctttt gtcccatacc gaccatgact ccttgatgcc ttgggcgacc gacgatcgag | 660 |
| gggaagacgg cacggggtgc gtcatctcct gcgaaaccgg ctttgcacat accggatcca | 720 |
| ttgtctacga caagagccgc tacatcgtcg tcacacatgt tgtcttttga ggttggacac | 780 |
| tgctcactag acagaaaaac ctcgtgccca tgg | 813 |
| SEQ ID NO. 8 Comprising a section of *Leptinotarsa decemlineata* strain Freeville β-actin sequence (SEQ ID NO. 13) with one nucleotide every eleven contiguous nucleotides of the sense strand sequence mutated to its complementary nucleotide, e.g. A was replaced by T, C was replaced by G | |
| atttaggtga cactatagaa ggacgaggtt ttactgtcta gtgtgcagtg tccatcctca | 60 |
| aaagagaaca tgtgtgtcga cgatgtaccg gctcttgtgg tagacaatgc atccggtatg | 120 |
| agcaaagccg gattcgcagg agttgacgca cccggtgccg tcttgccctc gatcgacggt | 180 |
| cgcccatggc atcaaggtgt catggtcgct atgggacaat aggactcata ggtaggagat | 240 |
| gtagcccaaa gctaaagagg tatgctcacc ctgatatacc ccatccaaca cggtatgatc | 300 |
| accaactcgg atgacatttc ttgtcccttc accttatacc tcatcctact ttcattattc | 360 |
| atataaacta ttactcacac atatcacaac tctgtcctcc tattaatatc cttctgttct | 420 |
| ctataaacta ccttattcta ctgttcatcc tcctcccatc atcctcgatg tcatcccagt | 480 |
| tggtgatgat accgtgttcg atggggtatt tcagggtgag gatacctctt ttgctttggg | 540 |
| cttcatctcc tacgtatgag tccttttgtc ccataccgac catgactcct tgatgccttg | 600 |
| ggcgaccgac gatcgagggg aagacggcac ggggtgcgtc atctcctgcg aaaccggctt | 660 |
| tgcacatacc ggatccattg tctacgacaa gagccgctac atcgtcgtca cacatgttgt | 720 |
| cttttgaggt tggacactgc tcactagaca gaaaaacctc gtgcccatgg | 770 |
| SEQ ID NO. 11 Comprising a section of *Leptinotarsa decemlineata* strain Freeville β-actin sequence (SEQ ID NO. 13) with two nucleotides every nine contiguous nucleotides of the sense strand sequence mutated to their complementary nucleotide, e.g. A was replaced by T, C was replaced by G | |
| atttaggtga cactatagaa ggtcgaggtt aatctgtctt ctgagcagac tccaaccaga | 60 |
| aaagacttca tgtgtctcga cgatcaagcg gctgatgtcg tactcaatgg aagcggtatg | 120 |
| accaaagccc ctttcgcacc agatgaccga ccccgtcgcg tcttcggctc gatccacggt | 180 |
| cgcggaaggc atgtaggagt ctaggtcggt tagggacaat tggactcaat cgtaggactt | 240 |
| gaagccgtaa gcaaatcagg tatcgacacc ctgttatacc cctacgaaca ccctatcatc | 300 |
| tgcaactggc ttgacatttc ttgtcccttc accttatacc tcatcctact ttcattattc | 360 |
| atataaacta ttactcacac atatcacaac tctgtcctcc tattaatatc cttctgttct | 420 |
| ctataaacta ccttattcta ctgttcatcc tcctcccatc atcctcgatg tcatcccagt | 480 |
| tggtgatgat accgtgttcg atggggtatt tcagggtgag gatacctctt ttgctttggg | 540 |
| cttcatctcc tacgtatgag tccttttgtc ccataccgac catgactcct tgatgccttg | 600 |
| ggcgaccgac gatcgagggg aagacggcac ggggtgcgtc atctcctgcg aaaccggctt | 660 |
| tgcacatacc ggatccattg tctacgacaa gagccgctac atcgtcgtca cacatgttgt | 720 |
| cttttgaggt tggacactgc tcactagaca gaaaaacctc gtgcccatgg | 770 |

TABLE 4-continued

RNA expression vectors for expressing precursor RNA sequences effective in suppressing expression of target genes, comprising a promoter, a target gene sense sequence with inserted, deleted or mutated nucleotides, sequence generating a single strand RNA loop, a target gene antisense sequence, and a nuclease restriction site.

SEQ ID NO. 12 Comprising a section of *Leptinotarsa decemlineata* strain Freeville β-actin sequence (SEQ ID NO. 13) with CT dinucleotide added every seven contiguous nucleotides of the sense sequence.

```
atttaggtga cactatagaa gctcacgagg ctttttctc tgtctagtct gagcagtctg   60

tccaacctct caaaactgac aacacttgtg tgactcgacg atctgtagcg gctctcttgt  120

ctcgtagacc taatggatct ccggtatctg tgcaaactgc cggttcttcg caggctagat  180

gacctgcacc ccctgtgccg tctcttcccc cttcgatcgc ttcggtcgct cccaaggctc  240

atcaagctga gtcatctggt cggtctatgg gacctaaaag gactctcata cctgtaggag  300

ctatgaagcc tccaaagcct aaaagagctg tatcctctca ccctgctaaa taccctccat  360

cgactacacg gtctatcatc actccaactg ctggatgacc tatttcttgt cccttcacct  420

tatacctcat cctactttca ttattcatat aaactattac tcacacatat cacaactctg  480

tcctcctatt aatatccttc tgttctctat aaactacctt attctactgt tcatcctcct  540

cccatcatcc tcgatgtcat cccagttggt gatgataccg tgttcgatgg ggtatttcag  600

ggtgaggata cctcttttgc tttgggcttc atctcctacg tatgagtcct tttgtcccat  660

accgaccatg actccttgat gccttgggcg accgacgatc gaggggaaga cggcacgggg  720

tgcgtcatct cctgcgaaac cggctttgca cataccggat ccattgtcta cgacaagagc  780

cgctacatcg tcgtcacaca tgttgtcttt tgaggttgga cactgctcac tagacagaaa  840

aacctcgtgc ccatgg                                                  856
```

SEQ ID NO. 18 Comprising a section of *Solenopsis Invicta* Buren β actin sequence (SEQ ID NO. 17) with one nucleotide every ten contiguous nucleotides of the sense strand sequence deleted.

```
atttaggtga cactatagaa gtctctctcc tcgactctac accagcgaag taacagcaat   60

caagattgtg acgatatgtt gcggattagt cgtgacaatg ggccggtatg tcaaggctgg  120

ttcgcgggga tgatgcacac gcgctgtttt cccagctcgt cggtctcctc gtcacagggt  180

gtgtggtcgg tagggtcaaa agacagttat ttggcgacgg gcgcaaagaa gagaggttat  240

tgacacaaag tatccataga acatgcatta ttataattgg gagacatggt tcttgtccct  300

tcaccttata cctcatccta ctttcattat tcatataaac tattactcac acatatcaca  360

actctgtcct cctattaata tccttctgtt ctctataaac taccttattc tactgttcat  420

cctcctccca tcatcctcgc catgtcatcc caattagtaa taatgccatg ttctatagga  480

tactttagtg tcaatatacc tctcttactt tgcgcctcgt cgccaacata actgtctttt  540

tgacccatac cgaccatcac accctgatga cgaggacgac cgacgatgct gggaaacaca  600

gcgcgtggtg catcatcccc cgcgaatcca gccttgcaca taccggaccc attgtccacg  660

actaatgccg caacatcatc gtcacacatc ttgattggct gttactttcg ctggtgttag  720

agtcgaggga gagagatccc atgg                                         744
```

TABLE 4-continued

| RNA expression vectors for expressing precursor RNA sequences effective in suppressing expression of target genes, comprising a promoter, a target gene sense sequence with inserted, deleted or mutated nucleotides, sequence generating a single strand RNA loop, a target gene antisense sequence, and a nuclease restriction site. |
|---|
| SEQ ID NO. 20 Comprising sections of *F. graminearum* cytochrome p540 lanosterol genes (SEQ ID NO. 19) with two contiguous nucleotides every twelve contiguous nucleotides of the sense strand sequence mutated to their complementary nucleotides, e.g. A was replaced by T, C was replaced by G |

```
atttaggtga cactatagaa ctccaagttt gacctgtccc tggcccgtct ctaccacctc    60

ctcgatatgc ccttcacccc ctacaacttc atggatcact gggccggtct cccctggttc   120

cgtaagcgcc tccacgccca ggccactgtt gccttgatct acatgctcac tatcaagctg   180

cgccgcgcct tgggcaacaa cctatccgag catctcatga tgaaggtcct tatgaacagt   240

ccatggcggg ggcgggaatt ccttatcggt ccaaagacaa tcccccactt tggtagcctt   300

gtcgtatacc tttgtcccaa caggaagctc atgctacaaa agaagaatgt caagtttccc   360

cttacgcaat tagcactcga gagacacgtc cagaaaatcg agcgactggt tcttgacatc   420

gtcgaaactc ttccatcctt tagtggcaga acttccacca tcgatcaccc caaggcatag   480

gctgagatat gaatctttac tcgctcacgt tctaagcagg gtgagctagt tcggagatta   540

ctcactgccc tgtttgctgc ctgtagtatt ggatccaccg tacaaattgg catcgacggg   600

tacgctttta acttcgactg ctcagataaa taccccgact gcttttgctt tattctcgat   660

ggcaaatcat ggactgtctt tgatggtccc aagcccaatg acttttacct caacggctta   720

cacgccgatg acaacgccga gctcgtttat gggttactta ccacgggcgt gtttggtctg   780

gaggttgtta ttgactgctc ctttgttctt gtcccttcac cttatacctc atcctacttt   840

cattattcat ataaactatt actcacacat atcacaactc tgtcctccta ttaatatcct   900

tctgttctct ataaactacc ttattctact gttcatcctc ctcccatcat cctcgcattg   960

gagcagtcat aaacaacctc ctcaccaaac acgggcgtgg taagtttccc ataaacgtcc  1020

tcggcgttga gatcggcgtg tttgccgttg aggataaagt cattgccctt gggaccaaga  1080

aagacagtcg ttgatttgcc aaggagaata aaggtaaagc agtcgccgta tttatctctg  1140

cagtcgaaga aaaaagcgta cgggtcgatg ccatattgta cggtgcttcc aatactagtg  1200

gcagcaaact cggcagtgag ttttctccga acttcctcac cctgcaaaga acgtgaggca  1260

gtaaagattg ttatctcagc cattgccttg gggacatcga tggtgctagt tctgccagaa  1320

aaggatggat cagtttcgac gtagtcaaga acctctcgct cgattaactg gacgtgtgac  1380

tcgagtgctt tttgcgtaag gccaaacttg acaaacttct tttgttccat gagcttcgag  1440

ttgggacaat cgtatacgac atcgctacca aagacgggga ttgtcaatgg accgatatcg  1500

aattcccgcg gccgccatgg agagttcata aggtgcttca tcatgtcatg ctcggattcg  1560

ttgttgccct tggcgcggcg ctccttgata gtgtccatgt agatcttggc aacagtgcgc  1620

tgggcgtggt cgcgcttacg gttccagggg agaggggccc agtgaagcat gaagttgatg  1680

ggggtgaagc ccatatcgag gtcgtggtag agagcggcca gggactcgtc aaacttgctg  1740

ccatgg                                                             1746
```

TABLE 4-continued

| RNA expression vectors for expressing precursor RNA sequences effective in suppressing expression of target genes, comprising a promoter, a target gene sense sequence with inserted, deleted or mutated nucleotides, sequence generating a single strand RNA loop, a target gene antisense sequence, and a nuclease restriction site. |
|---|
| SEQ ID NO. 22 Comprising a section of *Plutella xylostella* Acetylcholinesterase sequence (SEQ ID NO. 21) with two contiguous nucleotides every twelve contiguous nucleotides of the sense strand sequence mutated to their complementary nucleotides, e.g. A was replaced by T, C was replaced by G |
| atttaggtga cactatagaa tccgtgccgc agctgttgcg cgtcccacac catcaggtga 60 |
| agccattaag ggagcgaccg atcgttccaa tacatgtgtg gattttgggc gggggtttga 120 |
| tgagtggcag cgcgacactt gtactatata aaggggacat aatgggctct tcgagtgtag 180 |
| tgatcgtagg gtcgatgcag ttaagggttg gcggctttgg attttactac cttaacattt 240 |
| atttttcccg aggtagcgag ttcttgtccc ttcaccttat acctcatcct actttcatta 300 |
| ttcatataaa ctattactca cacatatcac aactctgtcc tcctattaat atccttctgt 360 |
| tctctataaa ctaccttatt ctactgttca tcctcctccc atcatcctcg ctcgctacca 420 |
| ggggaaaaat atttgttaag gtacaaaaat ccaaacgcgc caaccctata ctgcatcgag 480 |
| gctacgatca catcactcga agacgccatt atgtcggctt tatatagatc aagtgtcgcc 540 |
| gtgccactca tgtaaccccc gccgtaaatc cacactagta ttggaacctt cggtcgctcg 600 |
| gttaatggct tgtcctgatg gtgacggacg cgcaagtgct gcggcaccca ccatgg 656 |
| SEQ ID NO. 24 Comprising sections of *Diaphorina citri* cytochrome P450-like genes (SEQ ID NO. 23) with two contiguous nucleotides every twelve contiguous nucleotides of the sense strand sequence mutated to their complementary nucleotides, e.g. A was replaced by T, C was replaced by G |
| atttaggtga cactatagaa gaggagataa gagttgaagt tgacagcttc atgtttgtcg 60 |
| gacacgacag tacaacagcc gctatctgct ggtgactctt cgagatgatc agggaagtcg 120 |
| ttgacacgta gatgtttgaa gctcatgaca caagttcggc agccaagtgt tggacacacc 180 |
| atgagaacaa gagggaagag gatgacacgt tcaactttga aggtctagac acaacttgcg 240 |
| cagccatctc atggactctg ttcttgtccc ttcaccttat acctcatcct actttcatta 300 |
| ttcatataaa ctattactca cacatatcac aactctgtcc tcctattaat atccttctgt 360 |
| tctctataaa ctaccttatt ctactgttca tcctcctccc atcatcctcg cagagtccaa 420 |
| cagatggctg ccgaagttgt gtcatgacct tcaaacatga acgtgtctac ctcttccctg 480 |
| atgttctcat gcagtgtcca acagatggct gccgatgttg tgtcatgtcc ttcaaacatg 540 |
| aacgtgtcaa cctcttccct gatgttctcg aagagagacc agcagattcc ggctgttgtt 600 |
| gtgtcgtgtc cctcaaacat gaacgtgtca acttcttctc ttatctcgac ccatgg 656 |
| SEQ ID NO. 25 Comprising a section of *Leptinotarsa decemlineata* strain Freeville β-actin sequence (SEQ ID NO. 13) with one nucleotide every fifteen contiguous nucleotides of the sense strand sequence mutated to its complementary nucleotide, e.g. A was replaced by T, C was replaced by G |
| atttaggtga cactatagaa gcacgacgtt tttctgtcta gagagcagtg tccaacgtca 60 |
| aaagacaaca tctgtgacga cgatgttgcg gctcttgtcg ttgacaatgg atccggaatg 120 |
| tgcaaagccg gattcgcagg agatgaggca ccccgtgccg tgttcccctc gatcgtgggt 180 |
| cgcccaaggc aacaaggagt catggtgggt atgggacaaa acgactcata cgtaggtgat 240 |
| gaagcccaaa ggaaaagagg tatcctgacc ctgaaatacc cgatcgaaca cggtatgatc 300 |
| accaactggg aagacatttc ttgtcccttc accttatacc tcatcctact ttcattattc 360 |

TABLE 4-continued

RNA expression vectors for expressing precursor RNA sequences effective in suppressing expression of target genes, comprising a promoter, a target gene sense sequence with inserted, deleted or mutated nucleotides, sequence generating a single strand RNA loop, a target gene antisense sequence, and a nuclease restriction site.

```
atataaacta ttactcacac atatcacaac tctgtcctcc tattaatatc cttctgttct   420

ctataaacta ccttattcta ctgttcatcc tcctcccatc atcctcgatg tcatcccagt   480

tggtgatgat accgtgttcg atggggtatt tcagggtgag gatacctctt ttgctttggg   540

cttcatctcc tacgtatgag tccttttgtc ccataccgac catgactcct tgatgccttg   600

ggcgaccgac gatcgagggg aagacggcac ggggtgcgtc atctcctgcg aaaccggctt   660

tgcacatacc ggatccattg tctacgacaa gagccgctac atcgtcgtca cacatgttgt   720

cttttgaggt tggacactgc tcactagaca gaaaaacctc gtgcgcggcc gc           772
```

SEQ ID NO. 26 Comprising a section of *Leptinotarsa decemlineata* strain Freeville β-actin sequence (SEQ ID NO. 13) with one nucleotide every 23 contiguous nucleotides of the sense strand sequence mutated to its complementary nucleotide, e.g. A was replaced by T, C was replaced by G

```
atttaggtga cactatagaa gcacgaggtt attctgtcta gtgagcagtg tcctacctca    60

aaagacaaca tgtgtgtcga cgatgtagcg gctcttgtcc tagacaatgg atccggtatg   120

tggaaagccg gtttcgcagg agatgtcgca ccccgtgccg tcttccccac gatcgtcggt   180

cgcccaaggc aacaaggagt catggtcggt atggcacaaa aggactcata cgtaggacat   240

gaagcccaaa gcaaaagagg aatcctcacc ctgaaatacc ccaacgaaca cggtatcatc   300

accaacaggg atgacatttc ttgtcccttc accttatacc tcatcctact ttcattattc   360

atataaacta ttactcacac atatcacaac tctgtcctcc tattaatatc cttctgttct   420

ctataaacta ccttattcta ctgttcatcc tcctcccatc atcctcgatg tcatcccagt   480

tggtgatgat accgtgttcg atggggtatt tcagggtgag gatacctctt ttgctttggg   540

cttcatctcc tacgtatgag tccttttgtc ccataccgac catgactcct tgatgccttg   600

ggcgaccgac gatcgagggg aagacggcac ggggtgcgtc atctcctgcg aaaccggctt   660

tgcacatacc ggatccattg tctacgacaa gagccgctac atcgtcgtca cacatgttgt   720

cttttgaggt tggacactgc tcactagaca gaaaaacctc gtgcgcggcc gc           772
```

SEQ ID NO. 27 Comprising a section of *Leptinotarsa decemlineata* strain Freeville β-actin sequence (SEQ ID NO. 13) with one nucleotide every 34 contiguous nucleotides of the sense strand sequence mutated to its complementary nucleotide, e.g. A was replaced by T, C was replaced by G

```
atttaggtga cactatagaa gcacgaggtt tttctgtcta gtgagcagtc tccaacctca    60

aaagacaaca tgtgtgacga cgaagtagcg gctcttgtcg tagacaatgg atccggtttg   120

tgcaaagccg gtttcgcagg agatgacgca cgccgtgccg tcttcccctc gatcgtcggt   180

cgccctaggc atcaaggagt catggtcggt atgggacaat aggactcata cgtaggagat   240

gaagcccaaa gcataagagg tatcctcacc ctgaaatacc ccatcgatca cggtatcatc   300

accaactggg atgacatttc ttgtcccttc accttatacc tcatcctact ttcattattc   360

atataaacta ttactcacac atatcacaac tctgtcctcc tattaatatc cttctgttct   420

ctataaacta ccttattcta ctgttcatcc tcctcccatc atcctcgatg tcatcccagt   480

tggtgatgat accgtgttcg atggggtatt tcagggtgag gatacctctt ttgctttggg   540
```

TABLE 4-continued

RNA expression vectors for expressing precursor RNA sequences effective in suppressing expression of target genes, comprising a promoter, a target gene sense sequence with inserted, deleted or mutated nucleotides, sequence generating a single strand RNA loop, a target gene antisense sequence, and a nuclease restriction site.

```
cttcatctcc tacgtatgag tccttttgtc ccataccgac catgactcct tgatgccttg   600

ggcgaccgac gatcgagggg aagacggcac ggggtgcgtc atctcctgcg aaaccggctt   660

tgcacatacc ggatccattg tctacgacaa gagccgctac atcgtcgtca cacatgttgt   720

cttttgaggt tggacactgc tcactagaca gaaaaacctc gtgcnanacc atgg         774
```

SEQ ID NO. 28 Comprising a section of *Solenopsis invicta* muscle actin sequence (SEQ ID NO. 17) with one nucleotide every six contiguous nucleotides of the sense strand sequence mutated to its complementary nucleotide, e.g. A was replaced by T, C was replaced by G

```
atttaggtga cactatagaa gttctctgtc cctggactca aacacgagcg atagtaagag    60

ccattcaagt tgtgtcacga tcatgttccg gcaatagtcc tggactatgg gaccggtttg   120

tgctaggctc gattcccggg gcatgatcca ccaggcgctc tgtttgccag cttcgtccgt   180

cgtgctcgtg atcagcgtgt gttggtccgt atgcgtcaat aagactgtta tcttggccac   240

gagccgcaat gtaagtgagg tttattgtca ctatagtatg ctatacaaca tcgcattttt   300

acttattggc atgacttggt tcttgtccct tcaccttata cctcatccta ctttcattat   360

tcatataaac tattactcac acatatcaca actctgtcct cctattaata tccttctgtt   420

ctctataaac taccttattc tactgttcat cctcctccca tcatcctcgc catgtcatcc   480

caattagtaa taatgccatg ttctatagga tactttagtg tcaatatacc tctcttactt   540

tgcgcctcgt cgccaacata actgtctttt tgacccatac cgaccatcac accctgatga   600

cgaggacgac cgacgatgct gggaaacaca gcgcgtggtg catcatcccc cgcgaatcca   660

gccttgcaca taccggaccc attgtccacg actaatgccg caacatcatc gtcacacatc   720

ttgattggct gttactttcg ctggtgttag agtcgaggga gagagatccc atgg         774
```

SEQ ID NO. 29 Comprising a section of *Solenopsis invicta* muscle actin sequence (SEQ ID NO. 17) with one nucleotide every eight contiguous nucleotides of the sense strand sequence deleted.

```
atttaggtga cactatagaa gtctctctcc tcgacctaac acagcgaaat aacagcaatc    60

aagtgtgtga gatgatgtgc ggcatagtcg tgacaatggt ccggttgtgc aagctggatc   120

gcggggatga tgcccacgcg tgtgtttcca gcatgtcggt ctcctcgtat caggggtgat   180

ggcggtatgg tcaaaagaca gtttgttggc acgaggccaa agtagagagg ttattgacct   240

aaagttccta taaacatgga ttattataat tggatgacat gttcttgtcc cttcacctta   300

tacctcatcc tactttcatt attcatataa actattactc acacatatca caactctgtc   360

ctcctattaa tatccttctg ttctctataa actaccttat tctactgttc atcctcctcc   420

catcatcctc gccatgtcat cccaattagt aataatgcca tgttctatag gatactttag   480

tgtcaatata cctctcttac tttgcgcctc gtcgccaaca taactgtctt tttgacccat   540

accgaccatc acaccctgat gacgaggacg accgacgatg ctgggaaaca cagcgcgtgg   600

tgcatcatcc cccgcgaatc cagccttgca cataccggac ccattgtcca cgactaatgc   660

cgcaacatca tcgtcacaca tcttgattgg ctgttacttt cgctggtgtt agagtcgagg   720

gagagagatc gcggccgc                                                 738
```

TABLE 4-continued

RNA expression vectors for expressing precursor RNA sequences effective in suppressing expression of target genes, comprising a promoter, a target gene sense sequence with inserted, deleted or mutated nucleotides, sequence generating a single strand RNA loop, a target gene antisense sequence, and a nuclease restriction site.

SEQ ID NO. 30 Comprising a section of *Solenopsis invicta* muscle actin sequence (SEQ ID NO. 17) with one nucleotide every eight contiguous nucleotides of the sense strand sequence mutated to its complementary nucleotide, e.g. A was replaced by T, C was replaced by G

```
atttaggtga cactatagaa gttctctctg cctcgacact aacacgagcg aaactaacag   60
cgaatcaagt tgtgtgagga tgatgatgcg gcaatagtcg tcgacaatgc gtccggtttg  120
tgcaacgctg gatacgcggg gcatgatgct ccacgcggtg tgtttgccag catggtcggt  180
cctcctcgtg atcagggagt gatggacggt atgcgtcaaa atgacagttt tgttggccac  240
gaggcccaaa gtatgagagg tttattgact ctaaagtttc ctatacaaca tgggattatt  300
agtaattggc atgacatcgt tcttgtccct tcaccttata cctcatccta ctttcattat  360
tcatataaac tattactcac acatatcaca actctgtcct cctattaata tccttctgtt  420
ctctataaac taccttattc tactgttcat cctcctccca tcatcctcgc catgtcatcc  480
caattagtaa taatgccatg ttctatagga tactttagtg tcaatatacc tctcttactt  540
tgcgcctcgt cgccaacata actgtctttt tgacccatac cgaccatcac accctgatga  600
cgaggacgac cgacgatgct gggaaacaca gcgcgtggtg catcatcccc cgcgaatcca  660
gccttgcaca taccggaccc attgtccacg actaatgccg caacatcatc gtcacacatc  720
ttgattggct gttactttcg ctggtgttag agtcgaggga gagagatccc atgg         774
```

SEQ ID NO. 31 Comprising a section of *Solenopsis invicta* muscle actin sequence (SEQ ID NO. 17) with one guanine nucleotide added every seven contiguous nucleotides of the sense strand sequence

```
atttaggtga cactatagaa ggatctctcg tccctcggac tctaagcacc agcggaaagt   60
agacagccag atcaagagtg tgtgagcgat gatggttgcg ggcattagtg cgtggacgaa  120
tgggtgccgg tatggtgcaa gggctggatg tcgcgggggg atgatggcac cacggcgctg  180
tggtttcccg agcatcggtc ggtcggtcct cgtgcatcag gggtgtgatg ggtcggtgat  240
gggtcgaaaa agagcagtta tggttggcgg acgaggcggc aaagtgaaga gagggtatat  300
tggacactag aagtatcgct atagagacat ggcgattatt agctaattgg ggatgacgat  360
ggttcttgtc ccttcacctt atacctcatc ctactttcat tattcatata aactattact  420
cacacatatc acaactctgt cctcctatta atatccttct gttctctata aactacctta  480
ttctactgtt catcctcctc ccatcatcct cgccatgtca tcccaattag taataatgcc  540
atgttctata ggatacttta gtgtcaatat acctctctta ctttgcgcct cgtcgccaac  600
ataactgtct ttttgaccca taccgaccat cacaccctga tgacgaggac gaccgacgat  660
gctgggaaac acagcgcgtg gtgcatcatc ccccgcgaat ccagccttgc acataccgga  720
cccattgtcc acgactaatg ccgcaacatc atcgtcacac atcttgattg gctgttactt  780
tcgctggtgt tagagtcgag ggagagagat cgcggccgc                          819
```

SEQ ID NO. 32 Comprising a section of *Solenopsis invicta* muscle actin sequence (SEQ ID NO. 17) with one nucleotide every six contiguous nucleotides of the sense strand sequence mutated to its complementary nucleotide, e.g. A was replaced by T, C was replaced by G

```
atttaggtga cactatagaa gttctctctc ccacgactct aactccagcg aaagaaacag   60
ccaatgaaga tgtgtgtcga tgatgttccg gcattagtgg tggacaatgc gtccggtatg  120
```

TABLE 4-continued

| RNA expression vectors for expressing precursor RNA sequences effective in suppressing expression of target genes, comprising a promoter, a target gene sense sequence with inserted, deleted or mutated nucleotides, sequence generating a single strand RNA loop, a target gene antisense sequence, and a nuclease restriction site. | |
|---|---|
| agcaaggctg gtttcgcggg ggttgatgca ccaggcgctg tgttacccag catcgacggt | 180 |
| cgtcctggtc atcagggagt gatggtcgct atgggtcaat aagacagtta agttggcgac | 240 |
| gtggcgcaaa gttagagagg tattttgaca ctaatgtatc ctatacaaca tggcataatt | 300 |
| actaattcgg atgacatgct tcttgtccct tcaccttata cctcatccta ctttcattat | 360 |
| tcatataaac tattactcac acatatcaca actctgtcct cctattaata tccttctgtt | 420 |
| ctctataaac taccttattc tactgttcat cctcctccca tcatcctcgc catgtcatcc | 480 |
| caattagtaa taatgccatg ttctatagga tactttagtg tcaatatacc tctcttactt | 540 |
| tgcgcctcgt cgccaacata actgtctttt tgacccatac cgaccatcac accctgatga | 600 |
| cgaggacgac cgacgatgct gggaaacaca gcgcgtggtg catcatcccc cgcgaatcca | 660 |
| gccttgcaca taccggaccc attgtccacg actaatgccg caacatcatc gtcacacatc | 720 |
| ttgattggct gttactttcg ctggtgttag agtcgaggga gagagatccc atgg | 774 |
| SEQ ID NO. 2 Comprising a section of *Solenopsis invicta* muscle actin sequence (SEQ ID NO. 17) with two continguous nucleotides every nine contiguous nucleotides of the sense strand sequence mutated to their complementary nucleotides, e.g. A was replaced by T, C was replaced by G | |
| atttaggtga cactatagaa gtactctctc ggtcgactca tacaccaggc aaagtaagtg | 60 |
| ccaatcttga tgtgtctcga tgatcatgcg gcaaaagtcg tgctcaatgg gagcggtatg | 120 |
| accaaggctc cattcgcgcc ggatgatcga ccacgccgtg tgtttggcag catccacggt | 180 |
| cgtggtcgtc atgtgggtgt gtaggtcggt tagggtcaat tagacagtat tgttggcctc | 240 |
| gaggcggtaa gtaagtcagg tataaagaca ctattgtatc cttaagaaca tcccattatt | 300 |
| tgtaattggc ttgacatgct tcttgtccct tcaccttata cctcatccta ctttcattat | 360 |
| tcatataaac tattactcac acatatcaca actctgtcct cctattaata tccttctgtt | 420 |
| ctctataaac taccttattc tactgttcat cctcctccca tcatcctcgc catgtcatcc | 480 |
| caattagtaa taatgccatg ttctatagga tactttagtg tcaatatacc tctcttactt | 540 |
| tgcgcctcgt cgccaacata actgtctttt tgacccatac cgaccatcac accctgatga | 600 |
| cgaggacgac cgacgatgct gggaaacaca gcgcgtggtg catcatcccc cgcgaatcca | 660 |
| gccttgcaca taccggaccc attgtccacg actaatgccg caacatcatc gtcacacatc | 720 |
| ttgattggct gttactttcg ctggtgttag agtcgaggga gagagatccc atgg | 774 |
| SEQ ID NO. 10 Comprising a section of *Solenopsis invicta* muscle actin sequence (SEQ ID NO. 17) with one CT dinucleotide added every seven contiguous nucleotides of the sense strand sequence. | |
| atttaggtga cactatagaa gctatctctc cttccctcgc tactctaact caccagcctg | 60 |
| aaagtactac agccactatc aagacttgtg tgactcgatg atctgttgcg gctcattagt | 120 |
| ctcgtggacc taatgggtct ccggtatctg tgcaagctgc tggatcttcg cgggctggat | 180 |
| gatctgcacc acctgcgctg tctgtttccc ctagcatcgc ttcggtcgct tcctcgtctc | 240 |
| atcaggctgt gtgatctggt cggtctatgg gtcctaaaaa gactcagtta tctgttggcg | 300 |
| ctacgaggcc tgcaaagtct aagagagctg tatattctga cactactaag tatcctctat | 360 |
| agactacatg gcctattatt actctaattg ctggatgacc tatttcttgt cccttcacct | 420 |
| tatacctcat cctactttca ttattcatat aaactattac tcacacatat cacaactctg | 480 |

TABLE 4-continued

RNA expression vectors for expressing precursor RNA sequences effective in suppressing expression of target genes, comprising a promoter, a target gene sense sequence with inserted, deleted or mutated nucleotides, sequence generating a single strand RNA loop, a target gene antisense sequence, and a nuclease restriction site.

| | |
|---|---|
| tcctcctatt aatatccttc tgttctctat aaactacctt attctactgt tcatcctcct | 540 |
| cccatcatcc tcgccatgtc atcccaatta gtaataatgc catgttctat aggatacttt | 600 |
| agtgtcaata tacctctctt actttgcgcc tcgtcgccaa cataactgtc tttttgaccc | 660 |
| ataccgacca tcacaccctg atgacgagga cgaccgacga tgctgggaaa cacagcgcgt | 720 |
| ggtgcatcat cccccgcgaa tccagccttg cacataccgg acccattgtc cacgactaat | 780 |
| gccgcaacat catcgtcaca catcttgatt ggctgttact ttcgctggtg ttagagtcga | 840 |
| gggagagaga tcccatgg | 858 |

SEQ ID NO. 15 Comprising a section of *Plutella xylostella* Acetylcholinesterase sequence (SEQ ID NO. 21)

| | |
|---|---|
| atttaggtga cactatagaa tgggtgccgc agcacttgcg cgtccgtcac catcag-gaca | 60 |
| agccattaac cgagcgaccg aaggttccaa tactagtgtg gatttacggc gggggttaca | 120 |
| tgagtggcac ggcgacactt gatctatata aagccgacat aatggcgtct tcgagtgatg | 180 |
| tgatcgtagc ctcgatgcag tatagggttg gcgcgtttgg atttttgtac cttaacaaat | 240 |
| atttttcccc tggtagcgag ttcttgtccc ttcaccttat acctcatcct actttcatta | 300 |
| ttcatataaa ctattactca cacatatcac aactctgtcc tcctattaat atccttctgt | 360 |
| tctctataaa ctaccttatt ctactgttca tcctcctccc atcatcctcg ctcgctacca | 420 |
| ggggaaaaat atttgttaag gtacaaaaat ccaaacgcgc caaccctata ctgcatcgag | 480 |
| gctacgatca catcactcga agacgccatt atgtcggctt tatatagatc aagtgtcgcc | 540 |
| gtgccactca tgtaaccccc gccgtaaatc cacactagta ttggaacctt cggtcgctcg | 600 |
| gttaatggct tgtcctgatg gtgacggacg cgcaagtgct gcggcaccca ccatgg | 656 |

SEQ ID NO. 16 Comprising a section of *Solenopsis Invicta* Buren's actin sequence (SEQ ID NO. 17)

| | |
|---|---|
| atttaggtga cactatagaa gatctctctc cctcgactct aacaccagcg aaagtaacag | 60 |
| ccaatcaaga tgtgtgacga tgatgttgcg gcattagtcg tggacaatgg gtccggtatg | 120 |
| tgcaaggctg gattcgcggg ggatgatgca ccacgcgctg tgtttcccag catcgtcggt | 180 |
| cgtcctcgtc atcagggtgt gatggtcggt atgggtcaaa aagacagtta tgttggcgac | 240 |
| gaggcgcaaa gtaagagagg tatattgaca ctaaagtatc ctatagaaca tggcattatt | 300 |
| actaattggg atgacatggt tcttgtccct tcaccttata cctcatccta ctttcattat | 360 |
| tcatataaac tattactcac acatatcaca actctgtcct cctattaata tccttctgtt | 420 |
| ctctataaac taccttattc tactgttcat cctcctccca tcatcctcgc catgtcatcc | 480 |
| caattagtaa taatgccatg ttctatagga tactttagtg tcaatatacc tctcttactt | 540 |
| tgcgcctcgt cgccaacata actgtctttt tgacccatac cgaccatcac accctgatga | 600 |
| cgaggacgac cgacgatgct gggaaacaca gcgcgtggtg catcatcccc cgcgaatcca | 660 |
| gccttgcaca taccggaccc attgtccacg actaatgccg caacatcatc gtcacacatc | 720 |
| ttgattggct gttactttcg ctggtgttag agtcgaggga gagagatcgc ggccgc | 776 |

What is claimed is:

1. A composition comprising a post-transcriptionally modified double strand RNA (MdsRNA) wherein the MdsRNA comprises a double strand RNA having more than 30 nucleotide base pairs wherein at least 5% of the nucleotides independently comprise Formula (I):

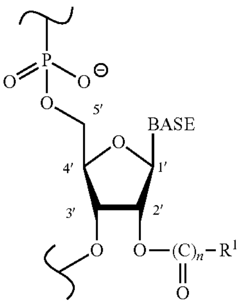

wherein n is 0 or 1, $R^1$ is or comprises a hydrocarbyl or substituted hydrocarbyl, and BASE is or comprises, independently, a nucleobase, wherein $(CO)_n$—$R^1$ is 2,4-dinitrophenyl, benzoyl, or N-methylanthranoyl.

2. The composition of claim 1 wherein $R^1$ is alkyl; substituted alkyl; alkenyl; substituted alkenyl; alkynyl; substituted alkynyl; aryl; substituted aryl; C1-C10 alkyl, C1-C10 alkenyl, or C1-C10 alkynyl wherein alkyl and alkenyl can be linear, branched or cyclic; hydrogen if n=1; methyl; ethyl; propyl; isopropyl; butyl; isobutyl; tert-butyl; pentyl; hexyl; cyclohexyl; heptyl; octyl; nonyl; decyl; vinyl; allyl; ethynyl; benzyl; cinnamyl; C6-C14 aryl; C6-C14 substituted aryl; heterocyclyl; C5-C14 heterocyclyl; phenyl; mono or disubstituted phenyl wherein the substituents are selected from C1-C10 alkyl, C1-C10 alkenyl, C1-C6 alkoxy, halogen, nitro, methylsulfonyl, and trifluoromethyl; 2-nitrophenyl; 4-nitrophenyl; 2,4-dinitrophenyl; 2-trifluromethylphenyl; 4-triflouromethylphenyl; styryl; C8-C16 substituted styryl; 2-aminophenyl; mono or disubstituted 2-aminophenyl wherein the substituents are selected from C1-C10 alkyl, C1-C10 alkenyl, C1-C6 alkoxy, halogen, nitro, methyl sulfonyl, and trifluoromethyl; N-alkyl-2-aminophenyl or N-aryl-2-aminophenyl wherein alkyl has the formula —$C_mH_{2m+1}$ (wherein m is an integer less than or equal to 12) and aryl is an aromatic moiety; 2-amino-3-methyl-phenyl; 2-amino-5-chlorophenyl; 2-methyl-5-chlorophenyl; N-methyla-2-minophenyl; N-ethyl-2-aminophenyl; N-propyl-2-aminophenyl; N-butyl-2-aminophenyl; N-pentyl-2-aminophenyl; N-methyl-2-amino-4-nitrophenyl; 2-methyl-3-furyl; 2-methylnicotyl or N-trifluoromethyl-2-aminophenyl; silanyl; substituted silanyl; C1-C10 alkylsilanyl; C3-C12 trialkylsilanyl; C2-C12 alkoxyalkyl; C2-C12 alkoxyalkenyl; C2-C12 alkylthioalkyl; alkylsulfonyl; C1-C10 alkylsulfonyl; C1-C10 haloalkyl; C1-C10 haloalkenyl or C1-C10 aminoalkyl; —$(CH_2CH_2O)_pCH_3$, —$(CH_2CH_2O)_pH$, or —$(CH_2CH_2O)_pCOOR^4$ wherein p is an integer from 2 to 8 and $R^4$ is H, alkyl, substituted alkyl, aryl, or substituted aryl; —$(CH_2CH_2O)_8COOH$; —$CH_2CH_2OH$; —$(CH_2CH_2O)_4OH$; —$(CH_2CH_2O)_6OH$; —$(CH_2CH_2O)_8OH$; —$(CH_2CH_2O)_8COOMe$; —$(CH_2CH_2O)_4OMe$; —$(CH_2CH_2O)_6OMe$; —$(CH_2CH_2O)_8OMe$; —$CH_2OCH_3$; —$CH_2OCH_2CH_3$; or —$CH_2OCH_2CH_2OCH_3$.

3. The composition of claim 1 wherein at least 10%, at least 25%, at least 60%, or at least 90% of the ribonucleotides independently comprise Formula (I).

4. The composition of claim 1 wherein the MdsRNA comprises a sequence having homology and/or complementarity to an expressed RNA in a target host.

5. The composition of claim 4 wherein the target host is an animal, insect, fungus, plant, protozoan, or weed.

6. The composition of claim 5 wherein the insect, fungus, or weed is selected from the group consisting of: Coleopteran, Lepidopteran, Dipteran, Hemipteran, Hymenopteran, Colorado potato beetle, corn root worm, red imported fire ant, *Aedes aegypti*, diamondback moth, Asian citrus psyllid, Hypocreales, *Fusarium graminearum, Fusarium avenacea, Fusarium culmorum, Fusarium oxysporum, Fusarium sporotrichioides*, Palmer Amaranth, Common Lambsquarters, Horseweed, Morning Glory, Waterhemp, Nutsedge, *Kochia*, Common Ragweed, Giant Ragweed, and Nightshade.

7. The composition of claim 4 wherein the MdsRNA reduces expression of a gene in a target host.

8. The composition of claim 1 further comprising at least one agent selected from the group consisting of: excipient, carrier, herbicide, fungicide, insecticide, and fertilizer.

9. The composition of claim 8 where the MdsRNA is present in an amount of less than 5% by weight, less than about 1% by weight, less than about 0.9% by weight, less than about 0.8% by weight, less than about 0.7% by weight, less than about 0.6% by weight, less than about 0.5% by weight, less than about 0.4% by weight, less than about 0.3% by weight, less than about 0.2% by weight, less than about 0.1% by weight, less than about 0.05% by weight, less than about 0.01% by weight, or less than about 0.001% by weight.

* * * * *

SEQUENCE LISTING

<160> NUMBER OF SEQ ID NOS: 32

<210> SEQ ID NO 1
<211> LENGTH: 2456
<212> TYPE: DNA
<213> ORGANISM: Artificial Sequence
<220> FEATURE:
<223> OTHER INFORMATION: pMA plasmid from GeneArt

<400> SEQUENCE: 1

```
ctaaattgta agcgttaata ttttgttaaa attcgcgtta aatttttgtt aaatcagctc     60

atttttttaac caataggccg aaatcggcaa aatcccttat aaatcaaaag aatagaccga    120

gatagggttg agtggccgct acagggcgct cccattcgcc attcaggctg cgcaactgtt    180

gggaagggcg tttcggtgcg ggcctcttcg ctattacgcc agctggcgaa agggggatgt    240

gctgcaaggc gattaagttg ggtaacgcca gggttttccc agtcacgacg ttgtaaaacg    300

acggccagtg agcgcgacgt aatacgactc actatagggc gaattggcgg aaggccgtca    360

aggcctaggc gcgccatgag ctctaaagct tcgctcgagc tgcggccgca cggatcctcg    420

aattcccaag cttatctcga gtagcggccg cttggatccc agaattctag gtacctctta    480

attaactggc ctcatgggcc ttccgctcac tgcccgcttt ccagtcggga aacctgtcgt    540

gccagctgca ttaacatggt catagctgtt tccttgcgta ttgggcgctc tccgcttcct    600

cgctcactga ctcgctgcgc tcggtcgttc gggtaaagcc tggggtgcct aatgagcaaa    660

aggccagcaa aaggccagga accgtaaaaa ggccgcgttg ctggcgtttt tccataggct    720

ccgcccccct gacgagcatc acaaaaatcg acgctcaagt cagaggtggc gaaacccgac    780

aggactataa agataccagg cgtttccccc tggaagctcc ctcgtgcgct ctcctgttcc    840

gaccctgccg cttaccggat acctgtccgc ctttctccct tcgggaagcg tggcgctttc    900

tcatagctca cgctgtaggt atctcagttc ggtgtaggtc gttcgctcca agctgggctg    960

tgtgcacgaa ccccccgttc agcccgaccg ctgcgcctta tccggtaact atcgtcttga   1020

gtccaacccg gtaagacacg acttatcgcc actggcagca gccactggta acaggattag   1080

cagagcgagg tatgtaggcg gtgctacaga gttcttgaag tggtggccta actacggcta   1140

cactagaaga acagtatttg gtatctgcgc tctgctgaag ccagttacct tcggaaaaag   1200

agttggtagc tcttgatccg gcaaacaaac caccgctggt agcggtggtt tttttgtttg   1260

caagcagcag attacgcgca gaaaaaaagg atctcaagaa gatcctttga tcttttctac   1320

ggggtctgac gctcagtgga acgaaaactc acgttaaggg attttggtca tgagattatc   1380

aaaaaggatc ttcacctaga tccttttaaa ttaaaaatga agttttaaat caatctaaag   1440

tatatatgag taaacttggt ctgacagtta ccaatgctta atcagtgagg cacctatctc   1500

agcgatctgt ctatttcgtt catccatagt tgcctgactc cccgtcgtgt agataactac   1560

gatacgggag ggcttaccat ctggccccag tgctgcaatg ataccgcgag aaccacgctc   1620

accggctcca gatttatcag caataaacca gccagccgga agggccgagc gcagaagtgg   1680

tcctgcaact ttatccgcct ccatccagtc tattaattgt tgccgggaag ctagagtaag   1740

tagttcgcca gttaatagtt tgcgcaacgt tgttgccatt gctacaggca tcgtggtgtc   1800

acgctcgtcg tttggtatgg cttcattcag ctccggttcc caacgatcaa ggcgagttac   1860

atgatccccc atgttgtgca aaaaagcggt tagctccttc ggtcctccga tcgttgtcag   1920

aagtaagttg gccgcagtgt tatcactcat ggttatggca gcactgcata attctcttac   1980

tgtcatgcca tccgtaagat gcttttctgt gactggtgag tactcaacca agtcattctg   2040
```

```
agaatagtgt atgcggcgac cgagttgctc ttgcccggcg tcaatacggg ataataccgc   2100

gccacatagc agaactttaa aagtgctcat cattggaaaa cgttcttcgg ggcgaaaact   2160

ctcaaggatc ttaccgctgt tgagatccag ttcgatgtaa cccactcgtg cacccaactg   2220

atcttcagca tcttttactt tcaccagcgt ttctgggtga gcaaaaacag gaaggcaaaa   2280

tgccgcaaaa aagggaataa gggcgacacg gaaatgttga atactcatac tcttcctttt   2340

tcaatattat tgaagcattt atcagggtta ttgtctcatg agcggataca tatttgaatg   2400

tatttagaaa aataaacaaa taggggttcc gcgcacattt ccccgaaaag tgccac       2456


<210> SEQ ID NO 2
<211> LENGTH: 774
<212> TYPE: DNA
<213> ORGANISM: Artificial Sequence
<220> FEATURE:
<223> OTHER INFORMATION: Solenopsis invicta muscle actin RNA expression
      sequence

<400> SEQUENCE: 2

atttaggtga cactatagaa gtactctctc ggtcgactca tacaccaggc aaagtaagtg     60

ccaatcttga tgtgtctcga tgatcatgcg gcaaaagtcg tgctcaatgg gagcggtatg    120

accaaggctc cattcgcgcc ggatgatcga ccacgccgtg tgtttggcag catccacggt    180

cgtggtcgtc atgtgggtgt gtaggtcggt tagggtcaat tagacagtat tgttggcctc    240

gaggcggtaa gtaagtcagg tataaagaca ctattgtatc cttaagaaca tcccattatt    300

tgtaattggc ttgacatgct tcttgtccct tcaccttata cctcatccta ctttcattat    360

tcatataaac tattactcac acatatcaca actctgtcct cctattaata tccttctgtt    420

ctctataaac taccttattc tactgttcat cctcctccca tcatcctcgc catgtcatcc    480

caattagtaa taatgccatg ttctatagga tactttagtg tcaatatacc tctcttactt    540

tgcgcctcgt cgccaacata actgtctttt tgacccatac cgaccatcac accctgatga    600

cgaggacgac cgacgatgct gggaaacaca gcgcgtggtg catcatcccc cgcgaatcca    660

gccttgcaca taccggaccc attgtccacg actaatgccg caacatcatc gtcacacatc    720

ttgattggct gttactttcg ctggtgttag agtcgaggga gagagatccc atgg          774


<210> SEQ ID NO 3
<211> LENGTH: 770
<212> TYPE: DNA
<213> ORGANISM: Artificial Sequence
<220> FEATURE:
<223> OTHER INFORMATION: Leptinotarsa decemlineata beta-actin RNA
      expression sequence

<400> SEQUENCE: 3

atttaggtga cactatagaa gcacgaggtt tttctgtcta gtgagcagtg tccaacctca     60

aaagacaaca tgtgtgacga cgatgtagcg gctcttgtcg tagacaatgg atccggtatg    120

tgcaaagccg gtttcgcagg agatgacgca ccccgtgccg tcttcccctc gatcgtcggt    180

cgcccaaggc atcaaggagt catggtcggt atgggacaaa aggactcata cgtaggagat    240

gaagcccaaa gcaaaagagg tatcctcacc ctgaaatacc ccatcgaaca cggtatcatc    300

accaactggg atgacatttc ttgtcccttc accttatacc tcatcctact ttcattattc    360

atataaacta ttactcacac atatcacaac tctgtcctcc tattaatatc cttctgttct    420

ctataaacta ccttattcta ctgttcatcc tcctcccatc atcctcgatg tcatcccagt    480

tggtgatgat accgtgttcg atggggtatt tcagggtgag gatacctctt ttgctttggg    540
```

-continued

```
cttcatctcc tacgtatgag tccttttgtc ccataccgac catgactcct tgatgccttg    600

ggcgaccgac gatcgagggg aagacggcac ggggtgcgtc atctcctgcg aaaccggctt    660

tgcacatacc ggatccattg tctacgacaa gagccgctac atcgtcgtca cacatgttgt    720

cttttgaggt tggacactgc tcactagaca gaaaaacctc gtgcccatgg               770


<210> SEQ ID NO 4
<211> LENGTH: 770
<212> TYPE: DNA
<213> ORGANISM: Artificial Sequence
<220> FEATURE:
<223> OTHER INFORMATION: Leptinotarsa decemlineata beta-actin RNA
      expression sequence
<400> SEQUENCE: 4

atttaggtga cactatagaa ggacgagctt tttgtgtctt gtgaggagtg tgcaaccaca     60

aaacacaact tgtgtcacga ccatgtaccg gctgttgtcc tagactatgg aaccggtttg    120

tgctaagccc gtttcccagg acatgaccca cccggtgccc tcttcgcctc gttcgtccgt    180

cgcgcaaggg atcaacgagt cttggtccgt atgcgacaat aggacacata cctaggacat    240

gaaccccaat gcaaatgagg tttcctctcc ctgtaatacg ccatccaaca ccgtatcttc    300

acctactggc atgacttttc ttgtcccttc accttatacc tcatcctact ttcattattc    360

atataaacta ttactcacac atatcacaac tctgtcctcc tattaatatc cttctgttct    420

ctataaacta ccttattcta ctgttcatcc tcctcccatc atcctcgatg tcatcccagt    480

tggtgatgat accgtgttcg atggggtatt tcagggtgag gatacctctt ttgctttggg    540

cttcatctcc tacgtatgag tccttttgtc ccataccgac catgactcct tgatgccttg    600

ggcgaccgac gatcgagggg aagacggcac ggggtgcgtc atctcctgcg aaaccggctt    660

tgcacatacc ggatccattg tctacgacaa gagccgctac atcgtcgtca cacatgttgt    720

cttttgaggt tggacactgc tcactagaca gaaaaacctc gtgcccatgg               770


<210> SEQ ID NO 5
<211> LENGTH: 733
<212> TYPE: DNA
<213> ORGANISM: Artificial Sequence
<220> FEATURE:
<223> OTHER INFORMATION: Leptinotarsa decemlineata beta-actin RNA
      expression sequence

<400> SEQUENCE: 5

atttaggtga cactatagaa gacgaggttt tctgttagtg agagtgtcca cctcaaagac     60

aactgtgtga gacgatgagc ggctttgtcg tgacaatgat ccggttgtgc aagccggttc    120

gcaggaatga cgcccccgtg cgtcttccct cgatgtcggt ccccaaggat caagggtcat    180

ggcggtatgg acaaaagact catcgtagga atgaagccaa agcaaagagg ttcctcacct    240

gaaatcccca tcaacacgga tcatcacaac tggatgacat ttcttgtccc ttcaccttat    300

acctcatcct actttcatta ttcatataaa ctattactca cacatatcac aactctgtcc    360

tcctattaat atccttctgt tctctataaa ctaccttatt ctactgttca tcctcctccc    420

atcatcctcg atgtcatccc agttggtgat gataccgtgt tcgatggggt atttcagggt    480

gaggatacct cttttgcttt gggcttcatc tcctacgtat gagtcctttt gtcccatacc    540

gaccatgact ccttgatgcc ttgggcgacc gacgatcgag ggaagacgg cacggggtgc    600

gtcatctcct gcgaaaccgg ctttgcacat accggatcca ttgtctacga caagagccgc    660
```

tacatcgtcg tcacacatgt tgtcttttga ggttggacac tgctcactag acagaaaaac 720
ctcgtgccca tgg 733

<210> SEQ ID NO 6
<211> LENGTH: 770
<212> TYPE: DNA
<213> ORGANISM: Artificial Sequence
<220> FEATURE:
<223> OTHER INFORMATION: Leptinotarsa decemlineata beta-actin RNA
expression sequence

<400> SEQUENCE: 6
atttaggtga cactatagaa ggacgaggta tttctgtgta gtgaggagtg tcctacctca 60
atagacaact tgtgtgagga cgatgaagcg gctgttgtcg ttgacaatgc atccggtttg 120
tgcaatgccg gttacgcagg acatgacgct ccccgtggcg tcttcgcctc gatggtcggt 180
cccccaaggg atcaaggtgt catggacggt atgcgacaaa acgactcatt cgtaggacat 240
gaagcgcaaa gcataagagg tttcctcacg ctgaaattcc ccatccaaca cggaatcatc 300
agcaactggc atgacatttc ttgtcccttc accttatacc tcatcctact ttcattattc 360
atataaacta ttactcacac atatcacaac tctgtcctcc tattaatatc cttctgttct 420
ctataaacta ccttattcta ctgttcatcc tcctcccatc atcctcgatg tcatcccagt 480
tggtgatgat accgtgttcg atggggtatt tcagggtgag gatacctctt ttgctttggg 540
cttcatctcc tacgtatgag tccttttgtc ccataccgac catgactcct tgatgccttg 600
ggcgaccgac gatcgagggg aagacggcac ggggtgcgtc atctcctgcg aaaccggctt 660
tgcacatacc ggatccattg tctacgacaa gagccgctac atcgtcgtca cacatgttgt 720
cttttgaggt tggacactgc tcactagaca gaaaaacctc gtgcccatgg 770

<210> SEQ ID NO 7
<211> LENGTH: 813
<212> TYPE: DNA
<213> ORGANISM: Artificial Sequence
<220> FEATURE:
<223> OTHER INFORMATION: Leptinotarsa decemlineata beta-actin RNA
expression sequence

<400> SEQUENCE: 7
atttaggtga cactatagaa ggcacgaggg tttttctggt ctagtggagc agtggtccaa 60
cgctcaaaag gacaacagtg tgtgagcgac gatggtagcg ggctcttgtg cgtagacgaa 120
tggatgccgg tatggtgcaa aggccggttg tcgcagggag atgacggcac cccggtgccg 180
tgcttccccg tcgatcggtc ggtcggccca agggcatcaa gggagtcatg ggtcggtgat 240
gggacgaaaa ggagctcata cggtaggagg atgaagcgcc aaagcgaaaa gagggtatcc 300
tgcaccctgg aaataccgcc atcgagacac ggtgatcatc agccaactgg ggatgacgat 360
ttcttgtccc ttcaccttat acctcatcct actttcatta ttcatataaa ctattactca 420
cacatatcac aactctgtcc tcctattaat atccttctgt tctctataaa ctaccttatt 480
ctactgttca tcctcctccc atcatcctcg atgtcatccc agttggtgat gataccgtgt 540
tcgatggggt atttcagggt gaggatacct cttttgcttt gggcttcatc tcctacgtat 600
gagtcctttt gtcccatacc gaccatgact ccttgatgcc ttgggcgacc gacgatcgag 660
gggaagacgg cacggggtgc gtcatctcct gcgaaaccgg ctttgcacat accggatcca 720
ttgtctacga caagagccgc tacatcgtcg tcacacatgt tgtcttttga ggttggacac 780
tgctcactag acagaaaaac ctcgtgccca tgg 813

<210> SEQ ID NO 8
<211> LENGTH: 770
<212> TYPE: DNA
<213> ORGANISM: Artificial Sequence
<220> FEATURE:
<223> OTHER INFORMATION: Leptinotarsa decemlineata beta-actin RNA expression sequence

<400> SEQUENCE: 8
atttaggtga cactatagaa ggacgaggtt ttactgtcta gtgtgcagtg tccatcctca 60
aaagagaaca tgtgtgtcga cgatgtaccg gctcttgtgg tagacaatgc atccggtatg 120
agcaaagccg gattcgcagg agttgacgca cccggtgccg tcttgccctc gatcgacggt 180
cgcccatggc atcaaggtgt catggtcgct atgggacaat aggactcata ggtaggagat 240
gtagcccaaa gctaaagagg tatgctcacc ctgatatacc ccatccaaca cggtatgatc 300
accaactcgg atgacatttc ttgtcccttc accttatacc tcatcctact ttcattattc 360
atataaacta ttactcacac atatcacaac tctgtcctcc tattaatatc cttctgttct 420
ctataaacta ccttattcta ctgttcatcc tcctcccatc atcctcgatg tcatcccagt 480
tggtgatgat accgtgttcg atggggtatt tcagggtgag gatacctctt ttgctttggg 540
cttcatctcc tacgtatgag tccttttgtc ccataccgac catgactcct tgatgccttg 600
ggcgaccgac gatcgagggg aagacggcac ggggtgcgtc atctcctgcg aaaccggctt 660
tgcacatacc ggatccattg tctacgacaa gagccgctac atcgtcgtca cacatgttgt 720
cttttgaggt tggacactgc tcactagaca gaaaaacctc gtgcccatgg 770

<210> SEQ ID NO 9
<211> LENGTH: 785
<212> TYPE: DNA
<213> ORGANISM: Artificial Sequence
<220> FEATURE:
<223> OTHER INFORMATION: F. graminearum cytochrome P450 lanosterol C-14alpha-demethylase genes CYP51A, CYP51B, and CYP51C-containing antisense sequence

<400> SEQUENCE: 9
cattggagca gtcataaaca acctcctcac caaacacggg cgtggtaagt ttcccataaa 60
cgtcctcggc gttgagatcg gcgtgtttgc cgttgaggat aaagtcattg cccttgggac 120
caagaaagac agtcgttgat ttgccaagga gaataaaggt aaagcagtcg ccgtatttat 180
ctctgcagtc gaagaaaaaa gcgtacgggt cgatgccata ttgtacggtg cttccaatac 240
tagtggcagc aaactcggca gtgagttttc tccgaacttc ctcaccctgc aaagaacgtg 300
aggcagtaaa gattgttatc tcagccattg ccttggggac atcgatggtg ctagttctgc 360
cagaaaagga tggatcagtt tcgacgtagt caagaacctc tcgctcgatt aactggacgt 420
gtgactcgag tgctttttgc gtaaggccaa acttgacaaa cttcttttgt tccatgagct 480
tcgagttggg acaatcgtat acgacatcgc taccaaagac ggggattgtc aatggaccga 540
tatcgaattc ccgcggccgc catggagagt tcataaggtg cttcatcatg tcatgctcgg 600
attcgttgtt gcccttggcg cggcgctcct tgatagtgtc catgtagatc ttggcaacag 660
tgcgctgggc gtggtcgcgc ttacggttcc aggggagagg ggcccagtga agcatgaagt 720
tgatgggggt gaagcccata tcgaggtcgt ggtagagagc ggccagggac tcgtcaaact 780
tgctg 785

-continued

<210> SEQ ID NO 10
<211> LENGTH: 858
<212> TYPE: DNA
<213> ORGANISM: Artificial Sequence
<220> FEATURE:
<223> OTHER INFORMATION: Solenopsis invicta muscle actin RNA expression sequence

<400> SEQUENCE: 10

```
atttaggtga cactatagaa gctatctctc cttccctcgc tactctaact caccagcctg     60

aaagtactac agccactatc aagacttgtg tgactcgatg atctgttgcg gctcattagt    120

ctcgtggacc taatgggtct ccggtatctg tgcaagctgc tggatcttcg cgggctggat    180

gatctgcacc acctgcgctg tctgtttccc ctagcatcgc ttcggtcgct tcctcgtctc    240

atcaggctgt gtgatctggt cggtctatgg gtcctaaaaa gactcagtta tctgttggcg    300

ctacgaggcc tgcaaagtct aagagagctg tatattctga cactactaag tatcctctat    360

agactacatg gcctattatt actctaattg ctggatgacc tatttcttgt cccttcacct    420

tatacctcat cctactttca ttattcatat aaactattac tcacacatat cacaactctg    480

tcctcctatt aatatccttc tgttctctat aaactacctt attctactgt tcatcctcct    540

cccatcatcc tcgccatgtc atcccaatta gtaataatgc catgttctat aggatacttt    600

agtgtcaata tacctctctt actttgcgcc tcgtcgccaa cataactgtc tttttgaccc    660

ataccgacca tcacaccctg atgacgagga cgaccgacga tgctgggaaa cacagcgcgt    720

ggtgcatcat cccccgcgaa tccagccttg cacataccgg acccattgtc cacgactaat    780

gccgcaacat catcgtcaca catcttgatt ggctgttact ttcgctggtg ttagagtcga    840

gggagagaga tcccatgg                                                  858
```

<210> SEQ ID NO 11
<211> LENGTH: 770
<212> TYPE: DNA
<213> ORGANISM: Artificial Sequence
<220> FEATURE:
<223> OTHER INFORMATION: Leptinotarsa decemlineata beta-actin RNA expression sequence

<400> SEQUENCE: 11

```
atttaggtga cactatagaa ggtcgaggtt aatctgtctt ctgagcagac tccaaccaga     60

aaagacttca tgtgtctcga cgatcaagcg gctgatgtcg tactcaatgg aagcggtatg    120

accaaagccc ctttcgcacc agatgaccga ccccgtcgcg tcttcggctc gatccacggt    180

cgcggaaggc atgtaggagt ctaggtcggt tagggacaat tggactcaat cgtaggactt    240

gaagccgtaa gcaaatcagg tatcgacacc ctgttatacc cctacgaaca ccctatcatc    300

tgcaactggc ttgacatttc ttgtcccttc accttatacc tcatcctact ttcattattc    360

atataaacta ttactcacac atatcacaac tctgtcctcc tattaatatc cttctgttct    420

ctataaacta ccttattcta ctgttcatcc tcctcccatc atcctcgatg tcatcccagt    480

tggtgatgat accgtgttcg atggggtatt tcagggtgag gatacctctt ttgctttggg    540

cttcatctcc tacgtatgag tccttttgtc ccataccgac catgactcct tgatgccttg    600

ggcgaccgac gatcgagggg aagacggcac ggggtgcgtc atctcctgcg aaaccggctt    660

tgcacatacc ggatccattg tctacgacaa gagccgctac atcgtcgtca cacatgttgt    720

cttttgaggt tggacactgc tcactagaca gaaaaacctc gtgcccatgg               770
```

-continued

<210> SEQ ID NO 12
<211> LENGTH: 856
<212> TYPE: DNA
<213> ORGANISM: Artificial Sequence
<220> FEATURE:
<223> OTHER INFORMATION: Leptinotarsa decemlineata beta-actin RNA expression sequence

<400> SEQUENCE: 12

```
atttaggtga cactatagaa gctcacgagg ctttttctc tgtctagtct gagcagtctg     60
tccaacctct caaaactgac aacacttgtg tgactcgacg atctgtagcg gctctcttgt   120
ctcgtagacc taatggatct ccggtatctg tgcaaactgc cggttcttcg caggctagat   180
gacctgcacc ccctgtgccg tctcttcccc cttcgatcgc ttcggtcgct cccaaggctc   240
atcaagctga gtcatctggt cggtctatgg gacctaaaag gactctcata cctgtaggag   300
ctatgaagcc tccaaagcct aaaagagctg tatcctctca ccctgctaaa taccctccat   360
cgactacacg gtctatcatc actccaactg ctggatgacc tatttcttgt cccttcacct   420
tatacctcat cctactttca ttattcatat aaactattac tcacacatat cacaactctg   480
tcctcctatt aatatccttc tgttctctat aaactacctt attctactgt tcatcctcct   540
cccatcatcc tcgatgtcat cccagttggt gatgataccg tgttcgatgg ggtatttcag   600
ggtgaggata cctcttttgc tttgggcttc atctcctacg tatgagtcct tttgtcccat   660
accgaccatg actccttgat gccttgggcg accgacgatc gaggggaaga cggcacgggg   720
tgcgtcatct cctgcgaaac cggctttgca cataccggat ccattgtcta cgacaagagc   780
cgctacatcg tcgtcacaca tgttgtcttt tgaggttgga cactgctcac tagacagaaa   840
aacctcgtgc ccatgg                                                     856
```

<210> SEQ ID NO 13
<211> LENGTH: 297
<212> TYPE: DNA
<213> ORGANISM: Leptinotarsa decemlineata

<400> SEQUENCE: 13

```
gcacgaggtt tttctgtcta gtgagcagtg tccaacctca aaagacaaca tgtgtgacga     60
cgatgtagcg gctcttgtcg tagacaatgg atccggtatg tgcaaagccg gtttcgcagg   120
agatgacgca ccccgtgccg tcttcccctc gatcgtcggt cgcccaaggc atcaaggagt   180
catggtcggt atgggacaaa aggactcata cgtaggagat gaagcccaaa gcaaaagagg   240
tatcctcacc ctgaaatacc ccatcgaaca cggtatcatc accaactggg atgacat       297
```

<210> SEQ ID NO 14
<211> LENGTH: 239
<212> TYPE: DNA
<213> ORGANISM: Diabrotica virgifera

<400> SEQUENCE: 14

```
gcaaagaaaa atgcgtcgaa aaataaaaga gttgcactcc aagccctcaa aaagaagaaa     60
cgattggaaa agacccaact acaaatagat ggaaccctta caactattga aatgcagagg   120
gaagccctcg aaggagctag cacaaatact gctgtattag attctatgaa aaatgctgca   180
gatgccctta agaaagctca taagaatttg aatgtagatg atgttcacga tatcatgga     239
```

<210> SEQ ID NO 15
<211> LENGTH: 656
<212> TYPE: DNA
<213> ORGANISM: Artificial Sequence -continued
<220> FEATURE:
<223> OTHER INFORMATION: Plutella xylostella Acetylcholinesterase RNA expression sequence

<400> SEQUENCE: 15

```
atttaggtga cactatagaa tgggtgccgc agcacttgcg cgtccgtcac catcaggaca     60
agccattaac cgagcgaccg aaggttccaa tactagtgtg gatttacggc gggggttaca    120
tgagtggcac ggcgacactt gatctatata aagccgacat aatggcgtct tcgagtgatg    180
tgatcgtagc ctcgatgcag tatagggttg gcgcgtttgg atttttgtac cttaacaaat    240
atttttcccc tggtagcgag ttcttgtccc ttcaccttat acctcatcct actttcatta    300
ttcatataaa ctattactca cacatatcac aactctgtcc tcctattaat atccttctgt    360
tctctataaa ctaccttatt ctactgttca tcctcctccc atcatcctcg ctcgctacca    420
ggggaaaaat atttgttaag gtacaaaaat ccaaacgcgc caaccctata ctgcatcgag    480
gctacgatca catcactcga agacgccatt atgtcggctt tatatagatc aagtgtcgcc    540
gtgccactca tgtaaccccc gccgtaaatc cacactagta ttggaacctt cggtcgctcg    600
gttaatggct tgtcctgatg gtgacggacg cgcaagtgct gcggcaccca ccatgg        656
```

<210> SEQ ID NO 16
<211> LENGTH: 776
<212> TYPE: DNA
<213> ORGANISM: Artificial Sequence
<220> FEATURE:
<223> OTHER INFORMATION: Solenopsis Invicta Buren actin RNA expression sequence

<400> SEQUENCE: 16

```
atttaggtga cactatagaa gatctctctc cctcgactct aacaccagcg aaagtaacag     60
ccaatcaaga tgtgtgacga tgatgttgcg gcattagtcg tggacaatgg gtccggtatg    120
tgcaaggctg gattcgcggg ggatgatgca ccacgcgctg tgtttcccag catcgtcggt    180
cgtcctcgtc atcagggtgt gatggtcggt atgggtcaaa aagacagtta tgttggcgac    240
gaggcgcaaa gtaagagagg tatattgaca ctaaagtatc ctatagaaca tggcattatt    300
actaattggg atgacatggt tcttgtccct tcaccttata cctcatccta ctttcattat    360
tcatataaac tattactcac acatatcaca actctgtcct cctattaata tccttctgtt    420
ctctataaac taccttattc tactgttcat cctcctccca tcatcctcgc catgtcatcc    480
caattagtaa taatgccatg ttctatagga tactttagtg tcaatatacc tctcttactt    540
tgcgcctcgt cgccaacata actgtctttt tgacccatac cgaccatcac accctgatga    600
cgaggacgac cgacgatgct gggaaacaca gcgcgtggtg catcatcccc cgcgaatcca    660
gccttgcaca taccggaccc attgtccacg actaatgccg caacatcatc gtcacacatc    720
ttgattggct gttactttcg ctggtgttag agtcgaggga gagagatcgc ggccgc        776
```

<210> SEQ ID NO 17
<211> LENGTH: 299
<212> TYPE: DNA
<213> ORGANISM: Solenopsis invicta

<400> SEQUENCE: 17

```
gatctctctc cctcgactct aacaccagcg aaagtaacag ccaatcaaga tgtgtgacga     60
tgatgttgcg gcattagtcg tggacaatgg gtccggtatg tgcaaggctg gattcgcggg    120
ggatgatgca ccacgcgctg tgtttcccag catcgtcggt cgtcctcgtc atcagggtgt    180
```

```
gatggtcggt atgggtcaaa aagacagtta tgttggcgac gaggcgcaaa gtaagagagg    240

tatattgaca ctaaagtatc ctatagaaca tggcattatt actaattggg atgacatgg     299


<210> SEQ ID NO 18
<211> LENGTH: 744
<212> TYPE: DNA
<213> ORGANISM: Artificial Sequence
<220> FEATURE:
<223> OTHER INFORMATION: Solenopsis Invicta Buren actin RNA expression
      sequence

<400> SEQUENCE: 18

atttaggtga cactatagaa gtctctctcc tcgactctac accagcgaag taacagcaat     60

caagattgtg acgatatgtt gcggattagt cgtgacaatg ggccggtatg tcaaggctgg    120

ttcgcgggga tgatgcacac gcgctgtttt cccagctcgt cggtctcctc gtcacagggt    180

gtgtggtcgg tagggtcaaa agacagttat ttggcgacgg gcgcaaagaa gagaggttat    240

tgacacaaag tatccataga acatgcatta ttataattgg gagacatggt tcttgtccct    300

tcaccttata cctcatccta ctttcattat tcatataaac tattactcac acatatcaca    360

actctgtcct cctattaata tccttctgtt ctctataaac taccttattc tactgttcat    420

cctcctccca tcatcctcgc catgtcatcc caattagtaa taatgccatg ttctatagga    480

tactttagtg tcaatatacc tctcttactt tgcgcctcgt cgccaacata actgtctttt    540

tgacccatac cgaccatcac accctgatga cgaggacgac cgacgatgct gggaaacaca    600

gcgcgtggtg catcatcccc cgcgaatcca gccttgcaca taccggaccc attgtccacg    660

actaatgccg caacatcatc gtcacacatc ttgattggct gttactttcg ctggtgttag    720

agtcgaggga gagagatccc atgg                                           744


<210> SEQ ID NO 19
<211> LENGTH: 785
<212> TYPE: DNA
<213> ORGANISM: Artificial Sequence
<220> FEATURE:
<223> OTHER INFORMATION: F. graminearum cytochrome P450 lanosterol
      C-14alpha-demethylase CYP51A, CYP51B, and CYP51C-containing
      sequence

<400> SEQUENCE: 19

cagcaagttt gacgagtccc tggccgctct ctaccacgac ctcgatatgg gcttcacccc     60

catcaacttc atgcttcact gggcccctct cccctggaac cgtaagcgcg accacgccca    120

gcgcactgtt gccaagatct acatggacac tatcaaggag cgccgcgcca agggcaacaa    180

cgaatccgag catgacatga tgaagcacct tatgaactct ccatggcggc cgcgggaatt    240

cgatatcggt ccattgacaa tccccgtctt tggtagcgat gtcgtatacg attgtcccaa    300

ctcgaagctc atggaacaaa agaagtttgt caagtttggc cttacgcaaa aagcactcga    360

gtcacacgtc cagttaatcg agcgagaggt tcttgactac gtcgaaactg atccatcctt    420

ttctggcaga actagcacca tcgatgtccc caaggcaatg gctgagataa caatctttac    480

tgcctcacgt tctttgcagg gtgaggaagt tcggagaaaa ctcactgccg agtttgctgc    540

cactagtatt ggaagcaccg tacaatatgg catcgacccg tacgcttttt tcttcgactg    600

cagagataaa tacggcgact gctttacctt tattctcctt ggcaaatcaa cgactgtctt    660

tcttggtccc aagggcaatg actttatcct caacggcaaa cacgccgatc tcaacgccga    720
```

-continued ggacgtttat gggaaactta ccacgcccgt gtttggtgag gaggttgttt atgactgctc 780
caatg 785

<210> SEQ ID NO 20
<211> LENGTH: 1746
<212> TYPE: DNA
<213> ORGANISM: Artificial Sequence
<220> FEATURE:
<223> OTHER INFORMATION: F. graminearum cytochrome p540 RNA expression sequence

<400> SEQUENCE: 20
atttaggtga cactatagaa ctccaagttt gacctgtccc tggcccgtct ctaccacctc 60
ctcgatatgc ccttcacccc ctacaacttc atggatcact gggccggtct cccctggttc 120
cgtaagcgcc tccacgccca ggccactgtt gccttgatct acatgctcac tatcaagctg 180
cgccgcgcct tgggcaacaa cctatccgag catctcatga tgaaggtcct tatgaacagt 240
ccatggcggg ggcgggaatt ccttatcggt ccaaagacaa tcccccactt tggtagcctt 300
gtcgtatacc tttgtcccaa caggaagctc atgctacaaa agaagaatgt caagtttccc 360
cttacgcaat tagcactcga gagacacgtc cagaaaatcg agcgactggt tcttgacatc 420
gtcgaaactc ttccatcctt tagtggcaga acttccacca tcgatcaccc caaggcatag 480
gctgagatat gaatctttac tcgctcacgt tctaagcagg gtgagctagt tcggagatta 540
ctcactgccc tgtttgctgc ctgtagtatt ggatccaccg tacaaattgg catcgacggg 600
tacgctttta acttcgactg ctcagataaa taccccgact gcttttgctt tattctcgat 660
ggcaaatcat ggactgtctt tgatggtccc aagcccaatg acttttacct caacggctta 720
cacgccgatg acaacgccga gctcgtttat gggttactta ccacgggcgt gtttggtctg 780
gaggttgtta ttgactgctc ctttgttctt gtcccttcac cttatacctc atcctacttt 840
cattattcat ataaactatt actcacacat atcacaactc tgtcctccta ttaatatcct 900
tctgttctct ataaactacc ttattctact gttcatcctc ctcccatcat cctcgcattg 960
gagcagtcat aaacaacctc ctcaccaaac acgggcgtgg taagtttccc ataaacgtcc 1020
tcggcgttga gatcggcgtg tttgccgttg aggataaagt cattgccctt gggaccaaga 1080
aagacagtcg ttgatttgcc aaggagaata aaggtaaagc agtcgccgta tttatctctg 1140
cagtcgaaga aaaaagcgta cgggtcgatg ccatattgta cggtgcttcc aatactagtg 1200
gcagcaaact cggcagtgag ttttctccga acttcctcac cctgcaaaga acgtgaggca 1260
gtaaagattg ttatctcagc cattgccttg gggacatcga tggtgctagt tctgccagaa 1320
aaggatggat cagtttcgac gtagtcaaga acctctcgct cgattaactg gacgtgtgac 1380
tcgagtgctt tttgcgtaag gccaaacttg acaaacttct tttgttccat gagcttcgag 1440
ttgggacaat cgtatacgac atcgctacca aagacgggga ttgtcaatgg accgatatcg 1500
aattcccgcg gccgccatgg agagttcata aggtgcttca tcatgtcatg ctcggattcg 1560
ttgttgccct tggcgcggcg ctccttgata gtgtccatgt agatcttggc aacagtgcgc 1620
tgggcgtggt cgcgcttacg gttccagggg agaggggccc agtgaagcat gaagttgatg 1680
ggggtgaagc ccatatcgag gtcgtggtag agagcggcca gggactcgtc aaacttgctg 1740
ccatgg 1746

-continued

<210> SEQ ID NO 21
<211> LENGTH: 299
<212> TYPE: DNA
<213> ORGANISM: Plutella xylostella

<400> SEQUENCE: 21
catatcggag gattgcctct atttgaacat atgggtgccg cagcacttgc gcgtccgtca 60
ccatcaggac aagccattaa ccgagcgacc gaaggttcca atactagtgt ggatttacgg 120
cgggggttac atgagtggca cggcgacact tgatctatat aaagccgaca taatggcgtc 180
ttcgagtgat gtgatcgtag cctcgatgca gtatagggtt ggcgcgtttg gatttttgta 240
ccttaacaaa tatttttccc ctggtagcga ggaagcggca ggaaatatgg gcttgtggg 299

<210> SEQ ID NO 22
<211> LENGTH: 656
<212> TYPE: DNA
<213> ORGANISM: Artificial Sequence
<220> FEATURE:
<223> OTHER INFORMATION: R. Plutella xylostella Acetylcholinesterase gene RNA expression sequence

<400> SEQUENCE: 22
atttaggtga cactatagaa tccgtgccgc agctgttgcg cgtcccacac catcaggtga 60
agccattaag ggagcgaccg atcgttccaa tacatgtgtg gattttgggc gggggtttga 120
tgagtggcag cgcgacactt gtactatata aaggggacat aatgggctct tcgagtgtag 180
tgatcgtagg gtcgatgcag ttaagggttg gcggctttgg attttactac cttaacattt 240
atttttcccg aggtagcgag ttcttgtccc ttcaccttat acctcatcct actttcatta 300
ttcatataaa ctattactca cacatatcac aactctgtcc tcctattaat atccttctgt 360
tctctataaa ctaccttatt ctactgttca tcctcctccc atcatcctcg ctcgctacca 420
ggggaaaaat atttgttaag gtacaaaaat ccaaacgcgc caaccctata ctgcatcgag 480
gctacgatca catcactcga agacgccatt atgtcggctt tatatagatc aagtgtcgcc 540
gtgccactca tgtaaccccc gccgtaaatc cacactagta ttggaacctt cggtcgctcg 600
gttaatggct tgtcctgatg gtgacggacg cgcaagtgct gcggcaccca ccatgg 656

<210> SEQ ID NO 23
<211> LENGTH: 240
<212> TYPE: DNA
<213> ORGANISM: Artificial Sequence
<220> FEATURE:
<223> OTHER INFORMATION: Diaphorina citri

<400> SEQUENCE: 23
gtcgagataa gagaagaagt tgacacgttc atgtttgagg gacacgacac aacaacagcc 60
ggaatctgct ggtctctctt cgagaacatc agggaagagg ttgacacgtt catgtttgaa 120
ggacatgaca caacatcggc agccatctgt tggacactgc atgagaacat cagggaagag 180
gtagacacgt tcatgtttga aggtcatgac acaacttcgg cagccatctg ttggactctg 240

<210> SEQ ID NO 24
<211> LENGTH: 656
<212> TYPE: DNA
<213> ORGANISM: Artificial Sequence
<220> FEATURE:
<223> OTHER INFORMATION: Diaphorina citri cytochrome P450-like RNA expression sequence

<400> SEQUENCE: 24
atttaggtga cactatagaa gaggagataa gagttgaagt tgacagcttc atgtttgtcg 60
gacacgacag tacaacagcc gctatctgct ggtgactctt cgagatgatc agggaagtcg 120
ttgacacgta gatgtttgaa gctcatgaca caagttcggc agccaagtgt tggacacacc 180
atgagaacaa gagggaagag gatgacacgt tcaactttga aggtctagac acaacttgcg 240
cagccatctc atggactctg ttcttgtccc ttcaccttat acctcatcct actttcatta 300
ttcatataaa ctattactca cacatatcac aactctgtcc tcctattaat atccttctgt 360
tctctataaa ctaccttatt ctactgttca tcctcctccc atcatcctcg cagagtccaa 420
cagatggctg ccgaagttgt gtcatgacct tcaaacatga acgtgtctac ctcttccctg 480
atgttctcat gcagtgtcca acagatggct gccgatgttg tgtcatgtcc ttcaaacatg 540
aacgtgtcaa cctcttccct gatgttctcg aagagagacc agcagattcc ggctgttgtt 600
gtgtcgtgtc cctcaaacat gaacgtgtca acttcttctc ttatctcgac ccatgg 656

<210> SEQ ID NO 25
<211> LENGTH: 772
<212> TYPE: DNA
<213> ORGANISM: Artificial Sequence
<220> FEATURE:
<223> OTHER INFORMATION: Leptinotarsa decemlineata beta-actin RNA
expression sequence

<400> SEQUENCE: 25
atttaggtga cactatagaa gcacgacgtt tttctgtcta gagagcagtg tccaacgtca 60
aaagacaaca tctgtgacga cgatgttgcg gctcttgtcg ttgacaatgg atccggaatg 120
tgcaaagccg gattcgcagg agatgaggca ccccgtgccg tgttcccctc gatcgtgggt 180
cgcccaaggc aacaaggagt catggtgggt atgggacaaa acgactcata cgtaggtgat 240
gaagcccaaa ggaaaagagg tatcctgacc ctgaaatacc cgatcgaaca cggtatgatc 300
accaactggg aagacatttc ttgtcccttc accttatacc tcatcctact ttcattattc 360
atataaacta ttactcacac atatcacaac tctgtcctcc tattaatatc cttctgttct 420
ctataaacta ccttattcta ctgttcatcc tcctcccatc atcctcgatg tcatcccagt 480
tggtgatgat accgtgttcg atggggtatt tcagggtgag gatacctctt ttgctttggg 540
cttcatctcc tacgtatgag tccttttgtc ccataccgac catgactcct tgatgccttg 600
ggcgaccgac gatcgagggg aagacggcac ggggtgcgtc atctcctgcg aaaccggctt 660
tgcacatacc ggatccattg tctacgacaa gagccgctac atcgtcgtca cacatgttgt 720
cttttgaggt tggacactgc tcactagaca gaaaaacctc gtgcgcggcc gc 772

<210> SEQ ID NO 26
<211> LENGTH: 772
<212> TYPE: DNA
<213> ORGANISM: Artificial Sequence
<220> FEATURE:
<223> OTHER INFORMATION: Leptinotarsa decemlineata beta-actin RNA
expression sequence

<400> SEQUENCE: 26
atttaggtga cactatagaa gcacgaggtt attctgtcta gtgagcagtg tcctacctca 60
aaagacaaca tgtgtgtcga cgatgtagcg gctcttgtcc tagacaatgg atccggtatg 120
tggaaagccg gtttcgcagg agatgtcgca ccccgtgccg tcttccccac gatcgtcggt 180
cgcccaaggc aacaaggagt catggtcggt atggcacaaa aggactcata cgtaggacat 240
gaagcccaaa gcaaaagagg aatcctcacc ctgaaatacc ccaacgaaca cggtatcatc 300
accaacaggg atgacatttc ttgtcccttc accttatacc tcatcctact ttcattattc 360
atataaacta ttactcacac atatcacaac tctgtcctcc tattaatatc cttctgttct 420
ctataaacta ccttattcta ctgttcatcc tcctcccatc atcctcgatg tcatcccagt 480
tggtgatgat accgtgttcg atggggtatt tcagggtgag gatacctctt ttgctttggg 540
cttcatctcc tacgtatgag tccttttgtc ccataccgac catgactcct tgatgccttg 600
ggcgaccgac gatcgagggg aagacggcac ggggtgcgtc atctcctgcg aaaccggctt 660
tgcacatacc ggatccattg tctacgacaa gagccgctac atcgtcgtca cacatgttgt 720
cttttgaggt tggacactgc tcactagaca gaaaaacctc gtgcgcggcc gc 772

<210> SEQ ID NO 27
<211> LENGTH: 774
<212> TYPE: DNA
<213> ORGANISM: Artificial Sequence
<220> FEATURE:
<223> OTHER INFORMATION: Leptinotarsa decemlineata beta-actin RNA expression sequence
<220> FEATURE:
<221> NAME/KEY: misc_feature
<222> LOCATION: (765)..(765)
<223> OTHER INFORMATION: n is a, c, g, or t
<220> FEATURE:
<221> NAME/KEY: misc_feature
<222> LOCATION: (767)..(767)
<223> OTHER INFORMATION: n is a, c, g, or t

<400> SEQUENCE: 27
atttaggtga cactatagaa gcacgaggtt tttctgtcta gtgagcagtc tccaacctca 60
aaagacaaca tgtgtgacga cgaagtagcg gctcttgtcg tagacaatgg atccggtttg 120
tgcaaagccg gtttcgcagg agatgacgca cgccgtgccg tcttcccctc gatcgtcggt 180
cgccctaggc atcaaggagt catggtcggt atgggacaat aggactcata cgtaggagat 240
gaagcccaaa gcataagagg tatcctcacc ctgaaatacc ccatcgatca cggtatcatc 300
accaactggg atgacatttc ttgtcccttc accttatacc tcatcctact ttcattattc 360
atataaacta ttactcacac atatcacaac tctgtcctcc tattaatatc cttctgttct 420
ctataaacta ccttattcta ctgttcatcc tcctcccatc atcctcgatg tcatcccagt 480
tggtgatgat accgtgttcg atggggtatt tcagggtgag gatacctctt ttgctttggg 540
cttcatctcc tacgtatgag tccttttgtc ccataccgac catgactcct tgatgccttg 600
ggcgaccgac gatcgagggg aagacggcac ggggtgcgtc atctcctgcg aaaccggctt 660
tgcacatacc ggatccattg tctacgacaa gagccgctac atcgtcgtca cacatgttgt 720
cttttgaggt tggacactgc tcactagaca gaaaaacctc gtgcnanacc atgg 774

<210> SEQ ID NO 28
<211> LENGTH: 774
<212> TYPE: DNA
<213> ORGANISM: Artificial Sequence
<220> FEATURE:
<223> OTHER INFORMATION: Solenopsis invicta muscle actin RNA expression sequence

<400> SEQUENCE: 28
atttaggtga cactatagaa gttctctgtc cctggactca aacacgagcg atagtaagag 60
ccattcaagt tgtgtcacga tcatgttccg gcaatagtcc tggactatgg gaccggtttg 120
tgctaggctc gattcccggg gcatgatcca ccaggcgctc tgtttgccag cttcgtccgt 180

```
cgtgctcgtg atcagcgtgt gttggtccgt atgcgtcaat aagactgtta tcttggccac    240

gagccgcaat gtaagtgagg tttattgtca ctatagtatg ctatacaaca tcgcattttt    300

acttattggc atgacttggt tcttgtccct tcaccttata cctcatccta ctttcattat    360

tcatataaac tattactcac acatatcaca actctgtcct cctattaata tccttctgtt    420

ctctataaac taccttattc tactgttcat cctcctccca tcatcctcgc catgtcatcc    480

caattagtaa taatgccatg ttctatagga tactttagtg tcaatatacc tctcttactt    540

tgcgcctcgt cgccaacata actgtctttt tgacccatac cgaccatcac accctgatga    600

cgaggacgac cgacgatgct gggaaacaca gcgcgtggtg catcatcccc cgcgaatcca    660

gccttgcaca taccggaccc attgtccacg actaatgccg caacatcatc gtcacacatc    720

ttgattggct gttactttcg ctggtgttag agtcgaggga gagagatccc atgg          774
```

<210> SEQ ID NO 29
<211> LENGTH: 738
<212> TYPE: DNA
<213> ORGANISM: Artificial Sequence
<220> FEATURE:
<223> OTHER INFORMATION: Solenopsis invicta muscle actin RNA expression sequence

<400> SEQUENCE: 29

```
atttaggtga cactatagaa gtctctctcc tcgacctaac acagcgaaat aacagcaatc     60

aagtgtgtga gatgatgtgc ggcatagtcg tgacaatggt ccggttgtgc aagctggatc    120

gcggggatga tgcccacgcg tgtgtttcca gcatgtcggt ctcctcgtat caggggtgat    180

ggcggtatgg tcaaaagaca gtttgttggc acgaggccaa agtagagagg ttattgacct    240

aaagttccta taaacatgga ttattataat tggatgacat gttcttgtcc cttcacctta    300

tacctcatcc tactttcatt attcatataa actattactc acacatatca caactctgtc    360

ctcctattaa tatccttctg ttctctataa actaccttat tctactgttc atcctcctcc    420

catcatcctc gccatgtcat cccaattagt aataatgcca tgttctatag gatactttag    480

tgtcaatata cctctcttac tttgcgcctc gtcgccaaca taactgtctt tttgacccat    540

accgaccatc acaccctgat gacgaggacg accgacgatg ctgggaaaca cagcgcgtgg    600

tgcatcatcc cccgcgaatc cagccttgca cataccggac ccattgtcca cgactaatgc    660

cgcaacatca tcgtcacaca tcttgattgg ctgttacttt cgctggtgtt agagtcgagg    720

gagagagatc gcggccgc                                                  738
```

<210> SEQ ID NO 30
<211> LENGTH: 774
<212> TYPE: DNA
<213> ORGANISM: Artificial Sequence
<220> FEATURE:
<223> OTHER INFORMATION: Solenopsis invicta muscle actin RNA expression sequence

<400> SEQUENCE: 30

```
atttaggtga cactatagaa gttctctctg cctcgacact aacacgagcg aaactaacag     60

cgaatcaagt tgtgtgagga tgatgatgcg gcaatagtcg tcgacaatgc gtccggtttg    120

tgcaacgctg gatacgcggg gcatgatgct ccacgcggtg tgtttgccag catggtcggt    180

cctcctcgtg atcagggagt gatggacggt atgcgtcaaa atgacagttt tgttggccac    240

gaggcccaaa gtatgagagg tttattgact ctaaagtttc ctatacaaca tgggattatt    300

agtaattggc atgacatcgt tcttgtccct tcaccttata cctcatccta ctttcattat    360
```

-continued

```
tcatataaac tattactcac acatatcaca actctgtcct cctattaata tccttctgtt    420

ctctataaac taccttattc tactgttcat cctcctccca tcatcctcgc catgtcatcc    480

caattagtaa taatgccatg ttctatagga tactttagtg tcaatatacc tctcttactt    540

tgcgcctcgt cgccaacata actgtctttt tgacccatac cgaccatcac accctgatga    600

cgaggacgac cgacgatgct gggaaacaca gcgcgtggtg catcatcccc cgcgaatcca    660

gccttgcaca taccggaccc attgtccacg actaatgccg caacatcatc gtcacacatc    720

ttgattggct gttactttcg ctggtgttag agtcgaggga gagagatccc atgg          774


<210> SEQ ID NO 31
<211> LENGTH: 819
<212> TYPE: DNA
<213> ORGANISM: Artificial Sequence
<220> FEATURE:
<223> OTHER INFORMATION: Solenopsis invicta muscle actin RNA expression
      sequence

<400> SEQUENCE: 31

atttaggtga cactatagaa ggatctctcg tccctcggac tctaagcacc agcggaaagt     60

agacagccag atcaagagtg tgtgagcgat gatggttgcg ggcattagtg cgtggacgaa    120

tgggtgccgg tatggtgcaa gggctggatg tcgcgggggg atgatggcac cacggcgctg    180

tggtttcccg agcatcggtc ggtcggtcct cgtgcatcag ggtgtgatgg ggtcggtgat    240

gggtcgaaaa agagcagtta tggttggcgg acgaggcggc aaagtgaaga gagggtatat    300

tggacactag aagtatcgct atagagacat ggcgattatt agctaattgg ggatgacgat    360

ggttcttgtc ccttcacctt atacctcatc ctactttcat tattcatata aactattact    420

cacacatatc acaactctgt cctcctatta atatccttct gttctctata aactacctta    480

ttctactgtt catcctcctc ccatcatcct cgccatgtca tcccaattag taataatgcc    540

atgttctata ggatacttta gtgtcaatat acctctctta ctttgcgcct cgtcgccaac    600

ataactgtct ttttgaccca taccgaccat cacaccctga tgacgaggac gaccgacgat    660

gctgggaaac acagcgcgtg gtgcatcatc ccccgcgaat ccagccttgc acataccgga    720

cccattgtcc acgactaatg ccgcaacatc atcgtcacac atcttgattg gctgttactt    780

tcgctggtgt tagagtcgag ggagagagat cgcggccgc                           819


<210> SEQ ID NO 32
<211> LENGTH: 774
<212> TYPE: DNA
<213> ORGANISM: Artificial Sequence
<220> FEATURE:
<223> OTHER INFORMATION: Solenopsis invicta muscle actin RNA expression
      sequence

<400> SEQUENCE: 32

atttaggtga cactatagaa gttctctctc ccacgactct aactccagcg aaagaaacag     60

ccaatgaaga tgtgtgtcga tgatgttccg gcattagtgg tggacaatgc gtccggtatg    120

agcaaggctg gtttcgcggg ggttgatgca ccaggcgctg tgttacccag catcgacggt    180

cgtcctggtc atcagggagt gatggtcgct atgggtcaat aagacagtta agttggcgac    240

gtggcgcaaa gttagagagg tattttgaca ctaatgtatc ctatacaaca tggcataatt    300

actaattcgg atgacatgct tcttgtccct tcaccttata cctcatccta ctttcattat    360

tcatataaac tattactcac acatatcaca actctgtcct cctattaata tccttctgtt    420

ctctataaac taccttattc tactgttcat cctcctccca tcatcctcgc catgtcatcc    480
```

-continued

| | | | | | | |
|---|---|---|---|---|---|---|
| caattagtaa | taatgccatg | ttctatagga | tactttagtg | tcaatatacc | tctcttactt | 540 |
| tgcgcctcgt | cgccaacata | actgtctttt | tgacccatac | cgaccatcac | accctgatga | 600 |
| cgaggacgac | cgacgatgct | gggaaacaca | gcgcgtggtg | catcatcccc | cgcgaatcca | 660 |
| gccttgcaca | taccggaccc | attgtccacg | actaatgccg | caacatcatc | gtcacacatc | 720 |
| ttgattggct | gttactttcg | ctggtgttag | agtcgaggga | gagagatccc | atgg | 774 |